United States Patent [19]
Bitler et al.

[11] Patent Number: 6,140,484
[45] Date of Patent: Oct. 31, 2000

[54] BAX ω PROTEIN AND METHODS

[75] Inventors: Catherine Mastroni Bitler; Stephen Scott Bowersox, both of Menlo Park; Roberto Crea, San Mateo; Susan Dunham Demo, San Francisco; William A. Horne, San Diego; Mei Zhou, Palo Alto, all of Calif.

[73] Assignee: Elan Pharmaceuticals, Inc., South San Francisco, Calif.

[21] Appl. No.: 09/037,742

[22] Filed: Mar. 10, 1998

Related U.S. Application Data

[60] Division of application No. 08/616,732, Mar. 15, 1996, Pat. No. 5,770,690, which is a continuation-in-part of application No. 08/495,042, Jun. 27, 1995, abandoned.

[51] Int. Cl.$^7$ .................................................. C07H 21/02
[52] U.S. Cl. ........................................ 536/23.1; 435/320.1
[58] Field of Search ........................... 435/6, 320.1, 69.1; 536/23.1

[56] References Cited

FOREIGN PATENT DOCUMENTS

| | | |
|---|---|---|
| WO92/06200 | 4/1992 | WIPO . |
| WO92/07942 | 5/1992 | WIPO . |
| WO95/05750 | 3/1995 | WIPO . |
| WO95/13292 | 5/1995 | WIPO . |
| WO95/28497 | 10/1995 | WIPO . |

OTHER PUBLICATIONS

Matsubara et al. 1995. WPI data base, abstract, Derwent Publications, Ltd. London.
Barr, P.J., and L.D. Tomei, "Apoptosis and Its Role in Human Disease," Bio/Technology 12: 487–493 (1994).
Boel, E., et al., "Calcium Binding in α–Amylases: An X–ray Diffraction Study at 2.1–Å Resolution of Two Enzymes from Aspergillus" Biochemistry 29:6244–6249 (1990).
Boise, Lawrence H., et al., "bcl–x, a bcl–2–Related Gene That Functions as a Dominary Regulator of Apoptotic Cell Death" Cell 74:597–608 (Aug. 27, 1993).
Chittenden, T., et al., "Induction of apoptosis by the Bcl–2 homologue Bak," Nature 374: 733–736 (1995).
Cory, S., "Regulation of Lymphocyte Survival By the BCL–2 Gene Family," Annu. Rev. Immunol. 13: 513–543 (1995).
Farrow, S.N., et al., "Cloning of a bcl–2 homologue by interaction with adenovirus E1B 19K," Nature 374: 731–733 (1995).
Fisher, D.E., "Apoptosis in Cancer Therapy: Crossing the Threshold," Cell 78: 539–542 (1994).
Gagliardini, V., et al., "Prevention of Vertebrate Neuronal Death by the crmA Gene," Science 263: 826–828 (1994).
Garcia, I., et al., "Prevention of Programmed Cell Death of Sympathetic Neurons by the bcl–2 Proto–Oncogene," Science 258: 302–304 (1992).
Hockenbery, D., et al., "Bcl–2 is an inner mitochondrial membrane protein that blocks programmed cell death," Nature 348: 334–336 (1990).
Jacobson, M.D., and M.C. Raff, "Programmed cell death and Bcl–2 protection in very low oxygen," Nature 374: 814–816 (1995).
Kiefer, M.C., et al., "Modulation of apoptosis by the widely distributed Bcl–2 homologue Bak," Nature 374: 736–739 (1995).
Matsubara, K. and Okubo, K., "Identifying Gene Signatures in 3"–Directed Human cDNA Library, e.g. for Diagnosis of Abnormal Cell Function, by Preparing cDNA That Reflects Relative Abundance of Corresponding mRNA Specific Human Tissue", Database WPI, Section Ch, Week 9527, Derwent Publications Ltd., London, GB (abstract), 1995.
Oltvai, Z.N., et al., "Bcl–2 Heterodimerizes In Vivo with a Conserved Homolog, Bax, That Accelerates Programed Cell Death," Cell 74: 609–619 (1993).
Raff, Martin C., et al., "Programmed Cell Death and the Control of Cell Survival: Lessons from the Nervous System," Science 262: 695–700 (1993).
Sedlak, T.W., et al., "Multiple Bcl–2 family members demonstrate selective dimerizations with Bax," Proc. Natl. Acad. Sci. USA 92: 7834–7838 (1995).
Shimizu, S., et al., "Prevention of hypoxia–induced cell death by Bcl–2 and Bcl–xL," Nature 374: 811–813 (1995).
Yin, X–M., et al., "BH1 and BH2 domains of Bcl–2 are required for inhibition of apoptosis and heterodimerization with Bax," Nature 369: 321–323. (1994).

Primary Examiner—James Ketter
Assistant Examiner—Iram Yucel
Attorney, Agent, or Firm—Peter J. Dehlinger; LeeAnn Gorthey

[57] ABSTRACT

Bax-ω polynucleotides and polypeptides, and compositions effective to hybridize to Bax-ω polynucleotides are disclosed. Also disclosed are methods for altering apoptosis in cells, for promoting cell survival and for identifying compounds capable of affecting the binding of Bax-ω to other proteins involved in apoptosis.

10 Claims, 9 Drawing Sheets

```
1/1                                            31/11
ATG GAC GGG TCC GGG GAG CAG CCC AGA GGC GGG GGG CCC ACC AGC TCT GAG CAG ATC ATG
 M   D   G   S   G   E   Q   P   R   G   G   G   P   T   S   S   E   Q   I   M

61/21                                          91/31
AAG ACA GGG GCC CTT TTG CTT CAG GGT TTC ATC CAG GAT CGA GCA GGG CGA ATG GGG GGG
 K   T   G   A   L   L   L   Q   G   F   I   Q   D   R   A   G   R   M   G   G

121/41                                         151/51
GAG GCA CCC GAG CTG GCC CTG GAC CCG GTG CCT CAG GAT GCG TCC ACC AAG AAG CTG AGC
 E   A   P   E   L   A   L   D   P   V   P   Q   D   A   S   T   K   K   L   S

181/61                                         211/71
GAG TGT CTC AAG CGC ATC GGG GAC GAA CTG GAC AGT AAC ATG GAG CTG CAG AGG ATG ATT
 E   C   L   K   R   I   G   D   E   L   D   S   N   M   E   L   Q   R   M   I

241/81                                         271/91
GCC GCC GTG GAC ACA GAC TCC CCC CGA GAG GTC TTT TTC CGA GTG GCA GCT GAC ATG TTT
 A   A   V   D   T   D   S   P   R   E   V   F   F   R   V   A   A   D   M   F

301/101                                        331/111
TCT GAC GGC AAC TTC AAC TGG GGC CGG GTT GTC GCC CTT TTC TAC TTT GCC AGC AAA CTG
 S   D   G   N   F   N   W   G   R   V   V   A   L   F   Y   F   A   S   K   L

361/121                                        391/131
GTG CTC AAG GCC CTG TGC ACC AAG GTG CCG GAA CTG ATC AGA ACC ATC ATG GGC TGG ACA
 V   L   K   A   L   C   T   K   V   P   E   L   I   R   T   I   M   G   W   T

421/141                   ____Bax 462 F____   451/151 ----------Jnct-------------
TTG GAC TTC CTC CGG GAG CGG CTG TTG GGC TGG ATC CAA GAC CAG GGT GGT TGG GGG CTG
 L   D   F   L   R   E   R   L   L   G   W   I   Q   D   Q   G   G   W   G   L 481/161        Bax 487 F                       511/171
CCC CTG GCC GAG TCA CTG AAG CGA CTG ATG TCC CTG CCT CCA GGA CGG CCT CCT CTC CTA
 P   L   A   E   S   L   K   R   L   M   S   L   P   P   G   R   P   P   L   L 541/181      Bax 590 R                         571/191
CTT TGG GAC GCC CAC GTG GCA GAC CGT GAC CAT CTT TGT GGC GGG AGT GCT CAC CGC CTC
 L   W   D   A   H   V   A   D   R   D   H   L   C   G   G   S   A   H   R   L 601/201          _____Bax R_____             631/211
ACT CAC CAT CTG GAA GAA GAT GGG CTG AGG CCC CCA GCT GCC TTG GAC TGT GTT TTT CCT
 T   H   H   L   E   E   D   G   L   R   P   P   A   A   L   D   C   V   F   P
                 epitope
661/221                                        691
CCA TAA ATT ATG GCA TTT TTC TGG GAG GGG TGG GGA TTG GGG GAC GTG GGC ATT TTT CTT
 P   Z 721                                            751
ACT TTT GTA ATT AAT GGG GGG TGT GGG GAA GAG TGG TCT TGA GGG GGT AAT AAA CCT CCT 781              "AP" Primer        811
TCG GGA CAC AAA AAA AAA AAA TGT CGA CAT CGA TCA GAT CTG
```

Fig. 1

```
1/1                                    31/11
GGG CTG CCC CTG GCC GAG TCA CTG AAG CGA CTG ATG TCC CTG CCT CCA GGA CGG CCT CCT
 G   L   P   L   A   E   S   L   K   R   L   M   S   L   P   P   G   R   P   P
  G   C   P   W   P   S   H   *   S   D   *   C   P   C   L   Q   D   G   L   L
   A   A   P   G   R   V   T   E   A   T   D   V   P   A   S   R   T   A   S   S

61/21                                  91/31
CTC CTA CTT TGG GAC GCC CAC GTG GCA GAC CGT GAC CAT CTT TGT GGC GGG AGT GCT CAC
 L   L   L   W   D   A   H   V   A   D   R   D   H   L   C   G   G   S   A   H
  S   Y   F   G   T   P   T   W   Q   T   V   T   I   F   V   A   G   V   L   T
   P   T   L   G   R   P   R   G   R   P   *   P   S   L   W   R   E   C   S   P

121/41                                 151/51
CGC CTC ACT CAC CAT CTG GAA GAA GAT GGG CTG AGG CCC CCA GCT GCC TTG GAC TGT GTT
 R   L   T   H   H   L   E   E   D   G   L   R   P   P   A   A   L   D   C   V
  A   S   L   T   I   W   K   K   M   G   *   G   P   Q   L   P   W   T   V   F
   P   H   S   P   S   G   R   R   W   A   E   A   P   S   C   L   G   L   C   F

181/61
TTT CCT CCA TAA
 F   P   P   *
  F   L   H
   S   S   I
```

Fig. 2

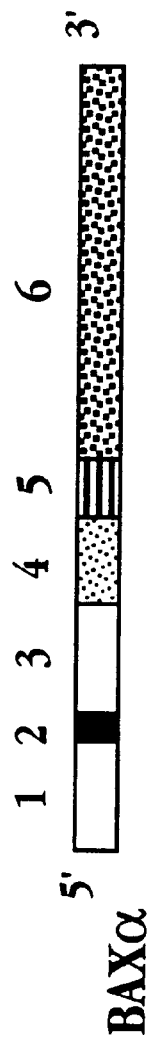
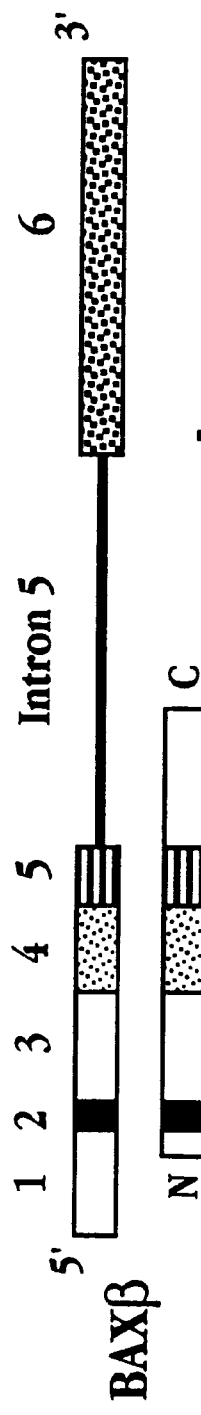
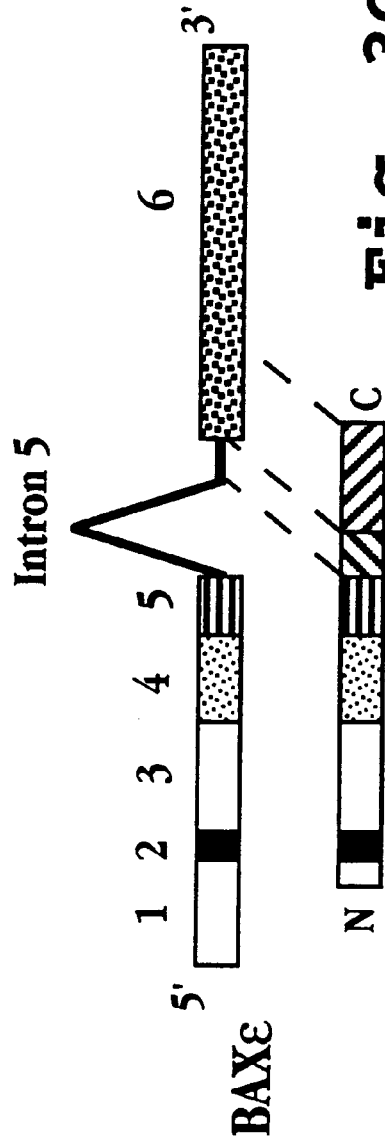
Fig. 3A
Fig. 3B
Fig. 3C

```
                 158 159                                                          192
BAXα ...WIQDQGGW|DG  LLSYFGIPIW  QTVTIFVAGV  LTASLTIWKK  MG
                                                                                  218
BAXβ ...WIQDQGGW|VR  LLKPPHPHHR  ALTTAPAPPS  LPPATPLGPW  AFWSRSQMCP  LPIFRSSDVV  YNAFSLRV
                                                                                                          221
BAXε ...WIQDQGGW|GL  PLAESLKRLM  SLPPGRPPLL  LWDAHVADRD  HLCGGSAHRL  THHLEEDGLR  PPAALDCVFP  P
```

Fig. 4

BAX ω PROTEIN AND METHODS

This application is a divisional of U.S. patent application Ser. No. 08/616,732, filed Mar. 15, 1996, now U.S. Pat. No. 5,770,690, which is a continuation-in-part of patent application Ser. No. 08/495,042, filed Jun. 27, 1995, now abandoned.

FIELD OF THE INVENTION

The present invention relates to Bax-ω polynucleotides, polypeptides, antibodies and their uses in affecting apoptosis and cell survival.

REFERENCES

Akao, Y., et al., *Can. Res.* 54:2468–2471 (1994).
Anderson, R. C., *Science* 256:808–813 (1992).
Apte, S. S., et al., *Genomics* 26:592–594 (1995).
Ausubel, F. M., et al., in *CURRENT PROTOCOLS IN MOLECULAR BIOLOGY* (John Wiley and Sons, Inc., Media, Pa.) (1988).
Barbas, C. F., et al., *Proc. Natl. Acad. Sci. USA* 89(10): 4457 (1992).
Bartel, P., et al., *BioTechniques* 14:920–924 (1993).
Beames, et al., *Biotechniques* 11:378 (1991).
Berkner, K. L., *BioTechniques* 6:616 (1988).
Breakefield, X. O., and DeLuca, N. A., *New Biol.* 3:230 (1992).
Boise, L. H., et al., *Cell* 74:597–608 (1993).
Borner, C., et al., *J. Cell. Biol.* 126:1059–1068 (1994).
Bradford, M. M., *Analytical Biochem.* 72:248–254 (1976).
Brent, R., et al., *Cell* 43:729–736 (1985).
Buchan, A. M., et al., *Stroke* 23:273–279 (1992).
Bunin, B. A. and Ellman, J. A., *J. Am. Chem. Soc.* 114:10997 (1992).
Bunin, B. A., et al., *Proc. Natl. Acad. Sci. USA* 91:4708 (1994).
Chatterjee, J., et al., *Science* 258:1485 (1992).
Chen-Levy, S., and Cleary, M. L., *J. Biol. Chem.* 265:4929–4933 (1990).
Chien, C.-t, et al., *Proc. Natl. Acad. Sci. U.S.A.* 88:9578 (1991).
Chomcyznski, P., and Sacchi, N., *Anal. Biochem.* 162:156–159 (1987).
Christiano, R. J., et al., *Proc. Natl. Acad. Sci. U.S.A.* 90:212 (1993).
Davies, A. M., *TINS* 18:355–358 (1995).
Dooley, C. T., et al., *Proc. Natl. Acad. Sci. USA* 90(22): 10822 (1993a).
Dooley, C. T., et al., *Life Sci.* 52(18):1509 (1993b).
Duke, R. C., et al., *Proc. Natl. Acad. Sci. U.S.A.* 80:6361 (1983).
Durfee, T., et al., *Genes & Development* 7:555 (1993).
Ecker, D. J., et al., *Nuc. Acids. Res.* 21(8):1853 (1993).
Eichler, J., et al., *Biochemistry* 32(41):11035 (1993).
Ellis, H. M., et al., *Cell* 44:817 (1986).
Fields, S., and Song, O., *Nature* 340:245 (1989).
Freese, A., et al., *Biochem. Pharm.* 40:2189 (1990).
Frohman, M. A., et al., *Proc. Natl. Acad. Sci. USA* 85:8998 (1988).
Frohman, M. A., in *PCR PROTOCOLS* (Innis, M. A., et al., Eds.) Academic Press, San Diego, Calif., pp. 28–38 (1990).
Furka, A., et al., *Int. J. Pept. Protein Res.* 37:487–493 (1991).
Garcia, et al., *Science* 258:302 (1992).
Ginsberg, M. D., and Busto, R., *Stroke* 20:1627–1642 (1989).
Graham, F. L., and Prevea, L., in *METHODS IN MOLECULAR BIOLOGY*, Vol. 7 (Murray, E. J., Ed.) (Humana, Clifton, N.J.) pp. 109–127 (1991).
Grunhaus, A. and Horowitz, M. S., *Semin. Virol.*, 3:237–252 (1992).
Guan, K. L. and Dixon, J. E., *Anal. Biochem.* 192:262 (1991).
Gyuris J., et al., *Cell* 75:791–803 (1993).
Hanada, M., et al., *J. Biol. Chem.* 270:11962–11969 (1995).
Harlow, E., et al., *ANTIBODIES: A LABORATORY MANUAL*, Cold Spring Harbor Laboratory Press (1988).
Heidenreich, O., et al., *Mol. Med. Today* pp. 128–133 (1995).
Hertz, J., and Gerard, R. D., *Proc. Natl. Acad. Sci. U.S.A.*, 90:2812–2816 (1993).
Hockenbery, D. M., et al., *Nature* 348:334–336 (1990).
Hockenbery, D. M., et al., *Cell* 75:241 (1993).
Hope, T. J., et al., *J. Virol.* 66:1849 (1992).
Houghten, R. A., *Proc. Natl. Acad. Sci. USA* 85:5131–5135 (1985).
Houghten, R. A., *Current Biology* 4:564 (1994).
Houghten, R. A., et al., *BioTechniques* 4:522–528 (1986).
Houghten, R. A., et al., *Nature* 354:84–86 (1991).
Houghten, R. A., et al., *BioTechniques* 13:412–421 (1992).
Jaffe, H. A., et al., *Nat. Genet.* 1:374 (1992).
Jones, N., and Shenk, T., *Cell* 16:683 (1979).
Kasahara, N., et al., *Science* 266:1373 (1994).
Kennedy, P. G. and Steiner, I. Q. *J. Med.* 86:697–702 (1993).
Kerr, J. F., et al., *Br. J. Canc.* 26:239–257 (1972).
Korsmeyer, S. J., et al., *Sem. Can. Biol.* 4:327–332 (1993).
Krajewski, S., et al., *Can Res.* 53:4701–4714 (1993).
Kramer, A., et al., *Pept. Res.* 6(6):314 (1993).
Kyte, J. and Doolittle, R. F., *J. Mol. Biol.* 157:105–132 (1982).
Lam, K. S., et al., *Nature (London)* 354:82–84 (1991).
Lam, K. S., et al., *Bioorg. Med. Chem. Lett.* 3:419–424 (1993).
Lathe, R., *J. Mol. Biol.* 183:1–12 (1985).
Larrick and Wright, *FASEB J.* 4:3215–23 (1990).
Malin, M. H., et al., *J. Exp. Med.* 176:1197 (1992).
Malin, M. H., et al., *Cell* 58:205 (1989).
Maniatis, T., et al., in *MOLECULAR CLONING: A LABORATORY MANUAL*, Cold Spring Harbor Laboratory (1982).
Miller, A. D., *Hum. Gene Ther.* 1:5 (1990).
Miller, A. D., *Nature* 357:455–460 (1992).
Mulligan, R. C., *Science* 260:926–932 (1993).
Mullis, K. B., U.S. Pat. No. 4,683,202, issued Jul. 28, 1987.

Mullis, K. B., et al., U.S. Pat. No. 4,683,195, issued Jul. 28, 1987.

Nguyen, M., et al., *J. Biol. Chem.* 269:16521–16524 (1994).

Ohlmayer, M. H., et al., *Proc Nat Acad Sci, USA*, 90(23): 10922 (1993).

Oltvai, Z. N., et al., *Cell* 74:609–619 (1993).

Pearson, W. R. and Lipman, D. J., *PNAS* 85:2444–2448 (1988).

Pearson, W. R., *Methods in Enzymology* 183:63–98 (1990).

Pinilla, C., et al., *Biotechniques* 13(6):901 (1992).

Pinilla, C., et al., *Gene* 128(1):71 (1993).

Pittman, R. N., et al., *J. Neurosci.* 13:3669–3680 (1993).

Pulsinelli, W. A., and Brierley, J. B., *Stroke* 10:267–272 (1979).

Pulsinelli, W. A., et al., *Ann. Neurol.* 11:491–498 (1982).

Quantin, B., et al., *Proc. Natl. Acad. Sci. U.S.A.* 89:2581 (1992).

Raff, et al., *Science* 262:695 (1993).

Reed, J. C., et al., *Nature* 336:259–261 (1988).

Reed, J. C., et al., *Mol. Cell Biol.* 10:4370–4374 (1990).

Reilly, P. R., et al., in *BACULOVIRUS EXPRESSION VECTORS: A LABORATORY MANUAL* (1992).

Rosenfeld, M. A., et al., *Cell,* 68:143–155 (1992).

Rossi, J. J., and Sarver, N., *Adv. Exp. Med. Biol.* 312:95 (1992).

Sambrook, J., et al., in *MOLECULAR CLONING: A LABORATORY MANUAL*, Second Edition, Cold Spring Harbor Laboratory (Cold Spring Harbor, N.Y.) (1989).

Schiestl, R. H. and R. D. Geist, *Curr. Genet.* 16:339–346 (1989).

Sebestyen, F., et al., *Bioorg. Med. Chem. Lett.* 3:413–418 (1993).

Shi, Y., et al., *Science* 257:212 (1992).

Smith, D. B. and Johnson, K. S., *Gene* 67:31 (1988).

Stein, C. A., et al., *Science* 261:1004 (1993).

Stratford-Perricaudet, L. D., et al., *J. Clin. Invest.* 90:626 (1992a).

Stratford-Perricaudet, L. D., et al., *Bone Marrow Transplant* 9(suppl. 1):151 (1992b).

Sullenger, B. A., et al., *J. Virol.* 65:6811 (1991).

Svendsen, C. N., et al., *J. Neurosci.* 14:75–87 (1994).

Talley, A. K., et al., *Mol. Cell Biol.* 15:2359–66 (1995).

Tanaka, S., et al., *J. Biol. Chem.* 268:10920–10926 (1993).

Thompson, C. B., *Science* 267:1456 (1995).

Tsujimoto, Y., and Croce, C. M., *Proc. Natl. Acad. Sci. USA* 83:5214–5218 (1986).

Vaux, D., et al., *Nature* 335:440–442 (1988).

Virgilio, A. A. and Ellman, J. A., *J. Am. Chem. Soc.* 116:11580 (1994).

Wagner, E., et al., *Proc. Natl. Acad. Sci. U.S.A.* 89:6099 (1992a).

Wagner, E., et al., *Proc. Natl. Acad. Sci. U.S.A.* 89:7934 (1992b).

Williams, et al., *Cell* 74:777 (1993).

Wu, G. Y., *J. Biol. Chem.* 266:14338 (1991).

Wyllie, A. H., *Brit. J. Cancer* 67:203–8 (1993).

Wyllie, A. H., et al., *Int. Rev. Cyt.* 68:251–306 (1979).

Yang, X., et al., *Science* 257:680 (1992).

Yin, X.-M., et al., *Nature* 369:321–323 (1994).

Yung, W. K., *Curr. Opin. Oncol.* 6:235–239 (1994).

Zhang, L. X., et al., *Neuroreport,* 3:700 (1992).

Zuckermann, R. N., et al., *Int. J. Pept. Protein Res.* 40:498–507 (1992).

BACKGROUND OF THE INVENTION

The survival of multicellular organisms is dependent on the maintenance and functioning of a variety of different cell types. Many cell types proliferate in the course of development, resulting in growth of the organism. Once development is complete, a homeostasis in cell numbers is typically achieved. In some cell types, such as central nervous system neurons, this homeostasis is maintained by a complete cessation of cell proliferation, while in other cell types, such as blood cells, a balance is achieved between cell proliferation and "physiological" cell death.

Physiological cell death occurs primarily through a "cell suicide" program, termed apoptosis. It is now thought that the apoptosis program is evolutionarily conserved among virtually all multicellular organisms, as well as among all the cells in a particular organism. Further, it is believed that in many cases, apoptosis may be a "default" program that must be actively inhibited in healthy surviving cells.

The decision by a cell to submit to apoptosis may be influenced by a variety of regulatory stimuli and environmental factors (Thompson, 1995). Physiological activators of apoptosis include tumor necrosis factor (TNF), Fas ligand, transforming growth factor β, the neurotransmitters glutamate, dopamine, N-methyl-D-aspartate, withdrawal of growth factors, loss of matrix attachment, calcium and glucorticoids. Damage-related inducers of apoptosis include heat shock, viral infection, bacterial toxins, the oncogenes myc, rel and E1A, tumor suppressor p53, cytolytic T-cells, oxidants, free radicals and nutrient deprivation (antimetabolites). Therapy-associated apoptosis inducers include gamma radiation, UV radiation and a variety of chemotherapeutic drugs, including cisplatin, doxorubicin, bleomycin, cytosine arabinoside, nitrogen mustard, methotrexate and vincristine. Toxin-related inducers of apoptosis include ethanol and β-amyloid peptide.

Apoptosis can have particularly devastating consequences when it occurs pathologically in cells that do not normally regenerate, such as neurons. Because such cells are not replaced when they die, their loss can lead to debilitating and sometimes fatal dysfunction of the affected organ. Such dysfunction is evidenced in a number of neurodegenerative disorders that have been associated with increased apoptosis, including Alzheimer's disease, Parkinson's disease, amyotrophic lateral sclerosis, retinitis pigmentosa and cerebellar degeneration. Further, it is believed that apoptosis is associated ischemic injury, such as typically occurs in cases of myocardial infarction, reperfusion injury and stroke.

The present invention provides compositions and methods useful for diagnosis and therapeutic treatment of apoptosis, as well as for the isolation of novel compounds effective to alter apoptosis.

SUMMARY OF THE INVENTION

In one aspect, the present invention includes a substantially pure polynucleotide (e.g., DNA), comprising at least 14 consecutive nucleotides, which will selectively hybridize to a DNA fragment having the sequence represented as SEQ ID NO:10. The polynucleotide may be produced synthetically or recombinantly. Preferred sizes for synthetically-produced polynucleotides (oligonucleotides) are about 15–30 basepairs, but include oligonucleotides up to about 50 basepairs. Recombinantly-produced polynucleotides of the present invention may range from tens of nucleotides to several kb in length.

In a general embodiment, the polynucleotide encodes the region of Bax-ω protein represented by SEQ ID NO:11 or portion thereof which comprises at least five consecutive amino acids. For example, the polynucleotide may encode SEQ ID NO:11 and/or may contain the sequence represented as SEQ ID NO:10 or portion thereof which comprises at least 15 consecutive nucleotides. In related general embodiments, the polynucleotide encodes the portion of the Bax-ω protein represented by SEQ ID NO:13. It may encode SEQ ID NO:13, and may contain the sequence represented as SEQ ID NO:12. The polynucleotide may encode a portion of, or the entire Bax-ω protein (e.g., the protein having the sequence represented as SEQ ID NO:9). In one such embodiment, the polynucleotide contains the sequence represented as SEQ ID NO:8. Of course, the invention also includes polynucleotides having sequences that are the reverse complement of those described above.

In another general embodiment, the polynucleotide as described above is inserted into a recombinant expression vector, which also contains a promoter operably linked to the polynucleotide, where the polynucleotide is positioned in the vector such that Bax-ω polypeptide sequences are expressed under control of the promoter in a desired host cell. Such expression vectors also preferably contain other control elements, such as transcription termination sequences, polyadenylation signals, selection markers and origins of replication compatible with the desired host cell. In one embodiment, the vector is pcDNA3-baxω. In a related aspect, the invention includes the expression vector as described above.

In another aspect, the invention includes polymer antisense compositions (e.g., polynucleotide compositions) capable of specifically hybridizing with sites selectively affecting the processing and/or translation of Bax-ω transcripts. One such composition is capable of specifically hybridizing to the Bax-ω-specific splice junction in intron 5 of the Bax gene. In one embodiment, the antisense composition is capable of specifically hybridizing with the sequence represented as SEQ ID NO:17 (e.g., the composition has the sequence represented as SEQ ID NO:16). In a general embodiment, such a polynucleotide antisense composition contains phosphorothioate polynucleotides.

In a related aspect, the invention includes a method of promoting apoptosis in a cell. The method comprises administering to the cell an amount of a polymer antisense composition, such as described above, effective to selectively inhibit translation of Bax-ω mRNA in the cell. Exemplary cells amenable to this method include pathological rapidly proliferating cells, such as tumor cells and abnormally-rapidly proliferating non-malignant cells.

In another related aspect, the invention includes a method of altering the ratio of other Bax transcripts, such as Bax-α, to Bax-ω in a cell expressing a pre-spliced Bax-ω transcript. The method comprises administering to the cell a composition which affects the splicing of the transcript. In one embodiment, the composition interacts with a splicing factor. For example, the composition may be an oligonucleotide homologous to a splice site in the transcript (e.g., an oligonucleotide having the sequence represented as SEQ ID NO:17).

In another aspect, the invention includes a method of identifying a Bax-ω polynucleotide or a Bax-ω polynucleotide homolog in a polynucleotide library. The method includes screening such a library (e.g., a cDNA library) with a polynucleotide probe, such as a Bax-ω polynucleotide described above, and isolating and sequencing positive clones.

The invention also includes a method of determining the amount of Bax-ω mRNA in a polynucleotide-containing sample. A Bax-ω polynucleotide probe as described above is hybridized with the sample under conditions effective to selectively form hybrids between the probe and Bax-ω polynucleotides contained in the sample, and the hybrids are detected. The relative number of hybrids detected is proportional to the amount of Bax-ω mRNA in the sample. The sample may be obtained from, for example, a tumor or another source of rapidly proliferating cells, such as affected skin cells from an individual with psoriasis.

In still another aspect, the present invention includes a method of inhibiting apoptosis in a cell (i.e., promoting cell survival). The method includes introducing into the cell a chimeric gene containing a polynucleotide encoding a Bax-ω polypeptide operably linked to a promoter effective to cause transcription of the polynucleotide in the cell. Expression of the Bax-ω polypeptide is effective to inhibit apoptosis in the cell, i.e., promote survival of the cell. An exemplary chimeric gene suitable for this purpose is the expression vector described above.

In a related aspect, the invention includes a method of promoting apoptosis in a cell. The method includes introducing into the cell a chimeric gene containing an antisense Bax-ω polynucleotide operably linked to a promoter effective to cause transcription of the polynucleotide in the cell. Transcription of the polynucleotide is effective to promote apoptosis in the cell. As above, a recombinant expression vector encoding such an antisense polynucleotide may be employed as the chimeric gene. The method is applicable, for example, to tumor cells and other pathological rapidly-proliferating cells.

In another aspect, the present invention includes a substantially pure polypeptide containing a region of at least five consecutive amino acids, where the region is homologous with a region of SEQ ID NO:13. The polypeptide preferably contains at least 7 consecutive amino acids; more preferably, at least about 10 consecutive amino acids. In one embodiment, the polypeptide comprises a full-length Bax-ω protein (e.g., has the sequence represented as SEQ ID NO:9).

Also in the present invention is a polypeptide antigen, where an immunoreactive portion of the antigen is homologous to a polypeptide encoded by the sequence represented as SEQ ID NO:18. In one embodiment, the antigen contains the sequence represented as SEQ ID NO:18.

The invention also includes a substantially purified antibody or FAb fragment specifically immunoreactive with an epitope contained in the region of the Bax-ω protein represented by SEQ ID NO:13. In one embodiment, the epitope is contained in a polypeptide having the amino acid sequence represented as SEQ ID NO:13. In a specific embodiment, the epitope has the amino acid sequence represented as SEQ ID NO:18. The antibody may be a monoclonal antibody or a polyclonal antibody.

Also part of the invention is a method of promoting apoptosis in a cell. The method includes administering to the cell, in a therapeutically-effective dose, a substantially purified antibody or FAb fragment such as described above. The method if useful, for example, in applications where it is desired to inhibit the growth and proliferation of pathological cells, such as tumor cells.

Another aspect of the invention includes a method of inhibiting apoptosis in a cell (i.e., promoting cell survival), by administering to the cell an amount of Bax-ω polypeptide that results in a significant inhibition of apoptosis. The method is applicable to any cell in which inhibition of apoptosis is desired. For example, the method may be applied to neuronal cells in the course of treatment for a neurodegenerative disorder, such as Alzheimer's disease, as well as following ischemia or trauma. The latter application may also be useful with cardiac cell.

The invention also includes a method of altering the activity of Bcl-2-like polypeptide in a cell, comprising administering to the cell an amount of Bax-ω polypeptide effective to significantly alter the activity of the Bcl-2-like polypeptide in the cell. Exemplary Bcl-2-like polypeptides amenable to this method include Bcl-XL, splice variants of Bcl-XL, Bax-ω, splice variants of Bax-α, Bad, splice variants of Bad, Bak, splice variants of Bak, Bag and splice variants of Bag.

In another aspect, the invention includes a method of identifying a compound effective to alter apoptosis in a cell. The method includes measuring the level of Bax-ω expression by such a cell in the presence and absence of a test compound, and identifying the compound as effective to alter apoptosis if the level of Bax-ω expression in the presence of the compound is significantly different from the level of Bax-ω expression in the absence of the compound. The level of Bax-ω expression may be determined by measuring levels of Bax-ω mRNA (e.g., Northern blot or reverse transcriptase (RT) polymerase chain reaction (PCR; Mullis, 1987; Mullis, et al., 1987)) or by measuring levels of Bax-ω protein (e.g., Western blot or ELISA).

Also part of the invention is a method of identifying a polypeptide that specifically interacts with Bax-ω. The method includes incubating a lysate from cells expressing Bax-ω with an antibody selectively immunoreactive with Bax-ω to produce a complex containing the antibody, Bax-ω, and any polypeptide that may be bound to Bax-ω, immunoprecipitating the complex, and identifying the polypeptide bound to Bax-ω by, for example, microsequencing a portion of the bound polypeptide.

The invention also includes another method of identifying a polypeptide that specifically interacts with Bax-ω. This method includes screening an expression library containing a plurality of polynucleotide clones with a Bax-ω polypeptide probe, selecting a positive clone, and identifying a polypeptide that specifically interacts with Bax-ω as a polypeptide encoded by the selected clone. In one general embodiment, the selecting includes detecting clones that selectively bind the probe using an antibody specifically immunoreactive with Bax-ω. In another general embodiment, the method is performed using the yeast two-hybrid system. In this embodiment, the polypeptide probe is a fusion protein probe containing a Bax-ω polypeptide in tandem with one of (i) a DNA binding domain or (ii) a DNA activation domain. The screening includes screening an expression library of fusion protein targets, with the fusion protein probe, where each fusion protein target contains a first portion having a polypeptide encoded by one of a plurality of different polynucleotide sequences represented in the library in tandem with a second portion having the other of (i) a DNA binding domain or (ii) a DNA activation domain. The selecting includes selecting a fusion protein target that specifically interacts with the fusion protein probe, and the identifying includes identifying a polypeptide that specifically interacts with Bax-ω as the polypeptide contained in the first portion of the selected fusion protein target.

In yet another aspect, the invention includes a method of identifying a compound capable of affecting the binding of Bax-ω to a partner of Bax-ω (PBω). The method includes (i) contacting PBω with Bax-ω in the presence and absence of a test compound, (ii) measuring the effect of the test compound on the degree of binding between PBω and Bax-ω, and (iii) identifying the compound as effective if the degree of binding in the presence of the compound is significantly different from the degree of binding in the absence of the compound. In one embodiment, the test compound is effective to inhibit binding between PBω and Bax-ω. In another embodiment, the test compound is effective to enhance binding between PBω and Bax-ω. In yet another embodiment, PBω is Bax-α.

This method may be performed using any of several systems amenable to binding assays, including, e.g., a yeast two-hybrid system, an enzyme-linked immune sorbent assay (ELISA), a scintillation proximity assay, or plasmon resonance. In one embodiment, the compound is a small molecule, such as one of a plurality of such molecules in a small molecule combinatorial library. In another embodiment, the compound is a peptide, such as one of a plurality of such peptides in a peptide combinatorial library.

These and other objects and features of the invention will become more fully apparent when the following detailed description is read in conjunction with the accompanying drawings.

BRIEF DESCRIPTION OF THE FIGURES

FIG. 1 shows the nucleotide and amino acid sequences of Bax-ω.

FIG. 2 shows the 3' end nucleotide sequence of the region of Bax-ω (omega tail region) corresponding to the 3' 49 nucleotides of intron 5 and 5' end of exon 6, as well as the amino acid translations of this sequence in all three reading frames.

FIGS. 3A, 3B and 3C show schematic diagrams of the mRNAs (5' and 3' ends indicated) and polypeptides (N- and C-termini indicated) of Bax-α (FIG. 3A), Bax-β (FIG. 3B) and Bax-ω (FIG. 3C).

FIG. 4 shows the different C-terminal amino acid sequences of Bax-α, Bax-β and Bax-ω.

BRIEF DESCRIPTION OF THE SEQUENCES

Figure 5A:
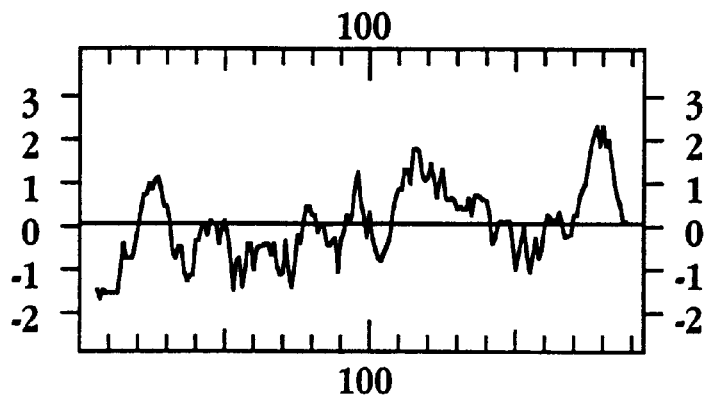
FIGS. 5A, 5B and 5C show Kyte-Doolittle hydrophobicity plots of Bax-α (FIG. 5A), Bax-β (FIG. 5B) and Bax-ω (FIG. 5C) amino acid sequences (Kyte and Doolittle, 1982).

SEQ ID NO:1 is the nucleotide sequence of PCR primer Bax F.

SEQ ID NO:2 is the nucleotide sequence of PCR primer Bax RI.

SEQ ID NO:3 is the nucleotide sequence of PCR primer Bax 487 F.

SEQ ID NO:4 is the nucleotide sequence of PCR primer Bax 462 F.

SEQ ID NO:5 is the nucleotide sequence of PCR primer Bax 590 R.

SEQ ID NO:6 is the nucleotide sequence of PCR primer 18S-F.

SEQ ID NO:7 is the nucleotide sequence of PCR primer 18S-R.

SEQ ID NO:8 is the nucleotide sequence of Bax-ω.

SEQ ID NO:9 is the predicted amino acid sequence from SEQ ID NO:8.

SEQ ID NO:10 is the nucleotide sequence of the 49 bp intron 5 fragment of Bax-ω.

SEQ ID NO:11 is the predicted amino acid sequence from SEQ ID NO:10.

SEQ ID NO:12 is the nucleotide sequence of the portion of Bax-ω between the intron 5 splice site and the 3' end of the coding sequence.

SEQ ID NO:13 is the predicted amino acid sequence from SEQ ID NO:12.

SEQ ID NO:14 is the nucleotide sequence of PCR primer AP.

SEQ ID NO:15 is the nucleotide sequence of PCR primer Jnct.

SEQ ID NO:16 is the nucleotide sequence of antisense oligonucleotide Anti-Jnct.

SEQ ID NO:17 is the nucleotide sequence of the exon 5/intron 5 junction region of Bax-ω.

SEQ ID NO:18 is the amino acid sequence of Bax-ω epitope #1 (antigen #1).

SEQ ID NO:19 is the nucleotide sequence of 3' RACE PCR primer 1.

SEQ ID NO:20 is the nucleotide sequence of 3' RACE PCR primer 2.

SEQ ID NO:21 is the nucleotide sequence of PCR primer BAX R.

DETAILED DESCRIPTION OF THE INVENTION

I. Definitions

The term "Bax-ω polynucleotide" (also referred to as "omega Bax polynucleotide") refers to (i) a polynucleotide that encodes a full-length Bax-ω polypeptide, (ii) a fragment of (i) at least 14 nucleotides long which contains an omega (ω) insert polynucleotide, or (iii) a polynucleotide at least 14 nucleotides long that selectively hybridizes with a polynucleotide having the sequence represented by the reverse complement of SEQ ID NO:10. An exemplary Bax-ω polynucleotide has the sequence presented herein as SEQ ID NO:8. A Bax-ω polynucleotide preferably contains at least about 16–18 consecutive nucleotides.

The term "Bax-ω polypeptide" (also referred to as "omega Bax polypeptide") refers to (i) a full length Bax-ω polypeptide, (ii) a fragment of (i) at least 5 amino acid residues in length containing an omega insert polypeptide, or (iii) a polypeptide containing a region of at least five consecutive amino acids, where the region has at least about an 80% homology, of conserved residues with a region of SEQ ID NO:13. It will be appreciated that various amino acid changes, insertions, deletions, etc., may be made to a Bax-ω polypeptide without substantially altering its activity, such as epitopic determinants. An exemplary Bax-ω polypeptide has the sequence presented herein as SEQ ID NO:9.

The term "omega insert polynucleotide" (also referred to as "ω insert polynucleotide") refers to (i) a polynucleotide that is co-extensive and selectively hybridizes with a polynucleotide having the sequence represented by the complement of SEQ ID NO:10 (omega insert), or (ii) a fragment of (i) at least 14 nucleotides in length. An exemplary omega insert polynucleotide has the sequence presented herein as SEQ ID NO:10.

The term "omega insert polypeptide" (also referred to as "ω insert polypeptide") refers to (i) a polypeptide that is co-extensive with and at least 80% homologous to a polypeptide having the sequence represented as SEQ ID NO:11 (omega insert), or (ii) a fragment of (i) at least 5 amino acids in length. An exemplary omega insert polypeptide has the sequence presented herein as SEQ ID NO:11.

The term "omega tail polypeptide" (also referred to as "ω tail polypeptide") refers to (i) a polypeptide that is co-extensive with and at least 80% homologous to a polypeptide having the sequence represented as SEQ ID NO:13 (omega tail), or (ii) a fragment of (i) at least 5 amino acids in length. An exemplary omega tail polypeptide has the sequence presented herein as SEQ ID NO:13.

When a first polynucleotide fragment or polypeptide fragment is said to "correspond to" a second polynucleotide fragment or polypeptide fragment, respectively, it means that the fragments or regions are essentially co-extensive with one another when the sequences representing the fragments are aligned using a sequence alignment program, such as "MACVECTOR" (IBI, New Haven, Conn.). "Corresponding" polynucleotide or polypeptide fragments typically contain a similar, if not identical, number of residues. It will be understood, however, that corresponding fragments may contain insertions or deletions of residues with respect to one another, as well as some differences in their sequences.

The BH1 domain of a Bax-ω polypeptide corresponds approximately to the region of SEQ ID NO:9 between residues 100 and 116. The BH2 domain of a Bax-ω polypeptide corresponds approximately to the region of SEQ ID NO:9 between residues 151 and 165.

The term "significant", when used with reference to "significantly different", "significantly inhibits" or "significantly stimulates", refers to a difference in a quantifiable parameter between the two groups being compared that is statistically-significant using standard statistical tests. For example, the degree of binding in a protein binding assay may be quantified using standard methods, and the degree of binding under different conditions can be compared for statistically-significant differences.

Two amino acid sequences or polypeptides that are between about five and twenty residues in length are considered homologous if they have greater than 80%, preferably greater than about 85%, of identically aligned amino acids (alignment determined, e.g., using the LALIGN program with default parameters). The LALIGN program is found in the FASTA version 1.7 suite of sequence comparison programs (Pearson, et al., 1988; Pearson, 1990; program available from William R. Pearson, Department of Biological Chemistry, Box 440, Jordan Hall, Charlottesville, Va.).

Two amino acid sequences or polypeptides that are between about 20 and 50 residues long are considered homologous if they have greater than 75%, preferably greater than about 80% of identically aligned amino acids.

Two amino acid sequences or polypeptides with an optimal alignment longer than about 50 amino acids and greater than 65%, preferably 70%, or more preferably 80% of identically aligned amino acids are considered homologous.

"Substantially isolated" typically refers to the at least partial purification of a Bax-ω polynucleotide, polypeptide, or related compound (e.g., anti-Bax-ω antibodies) away from unrelated or contaminating components (e.g., serum cells, proteins, and non-anti-Bax-ω antibodies). Methods and procedures for the isolation or purification of compounds or components of interest are described below (e.g., affinity purification of fusion proteins and recombinant production of Bax-ω polypeptides).

An antibody or antibody composition (e.g., polyclonal antibodies) is "selectively immunoreactive" with Bax-ω when the antibody or antibody composition is immunoreactive with a Bax-ω antigen but not with antigens present in other Bax transcripts (e.g., Bax-α, Bax-β, etc.).

An antibody or antibody composition (e.g., polyclonal antibodies) is "specifically immunoreactive" with Bax-ω when the antibody or antibody composition is not reactive with antigens typically present in normal sera, not exposed to Bax-ω.

A composition (e.g., antisense composition) is effective to "selectively inhibit" translation of a Bax-ω transcript if the composition inhibits translation of a Bax-ω transcript but does not significantly inhibit translation of other Bax transcripts (e.g., Bax-α, Bax-β, etc.).

II. Overview of Invention

Experiments performed in support of the present invention demonstrate the existence of a heretofore unknown transcript or group of transcripts of the Bax gene, termed Bax-ω. This group is characterized by the inclusion of a ~49 nucleotide region (omega insert polynucleotide, as exemplified by SEQ ID NO:10) derived from a region of the Bax gene (3' end of intron 5) previously thought to be spliced out of mRNAs encoding Bax polypeptides. As a result of the omega insert polynucleotide sequence, the reading frame of the Bax-ω transcripts downstream of the insertion (i.e., in exon 6) is shifted relative to that of Bax-α transcripts. A consequence of this reading frame shift is that Bax-ω transcripts encode a Bax polypeptide with a novel C-terminal end (e.g., SEQ ID NO:13) relative to the C-terminal ends of previously-characterized Bax polypeptides.

As described herein, these novel Bax-ω "omega tail" polypeptides may be used to generate antibodies specifically immunoreactive with Bax-ω polypeptides. Such antibodies may be used, for example, in therapeutic application where it is desired to affect Bax-ω-mediated apoptotic processes. It is also contemplated that the novel splice junction between exon 5 and intron 5 of Bax-ω, corresponding to the 5' end of the omega insert polynucleotide sequence, comprises an exemplary target for antisense-based compositions effective to specifically inhibit the translation of Bax-ω transcripts. Polymer compositions directed specifically against this region (i.e., polymer compositions which bind Bax-ω polynucleotides in the region of the exon 5/intron 5 splice) may be employed in therapeutic application, as the antibodies above, to promote apoptotic process which involve Bax-ω.

Further experiments performed in support of the present invention demonstrate that Bax-ω transcripts are expressed in mammalian brain. According to the teachings herein, therapeutically-administered Bax-ω polypeptides may promote cell survival under conditions which trigger programmed cell death.

As is described below, the elucidation of Bax-ω and its pattern of expression provides a basis for the development of drugs and methods for treatment of acute and chronic diseases and conditions characterized by cell death, such as stroke, consequences of cardiac arrest (i.e., hypoxia), traumatic head injury, neurodegenerative diseases, aging, and viral and other types of infections. The discovery also provides a basis for the identification of drugs and methods for inducing or promoting apoptosis in medical conditions involving the abnormal proliferation of cells, such as tumors and non-malignant cells proliferating at an abnormally-rapid rate (e.g., skin cells in a psoriasis lesion).

III. Apoptosis, Bcl-2 and Bax

Programmed cell death (apoptosis) is a normal physiological process that results from a complex cascade of cellular events that occur at specific stages of differentiation (reviewed in Raff, et al., 1993; Wyllie, 1993; Wyllie, et al., 1979; Kerr, et al., 1972). For example, in the developing vertebrate nervous system, approximately half the neurons generated in most neuronal populations die during the period when synapses are being formed between neurons and their targets. The mechanism by which death occurs is thought to be related to competition among neurons for limited access to target-derived trophic factors. In support of this view, at least some trophic factors appear to enhance survival by inhibiting an endogenous cell suicide program.

It is now widely accepted that apoptosis is a gene-directed process that co-exists with the processes of cell differentiation (reviewed in Williams, et al., 1993). In fact, the number of cells in a growing or proliferating tissue can be thought of as reflecting the balance between cell division and cell death. In particular, tumor growth may not necessarily be simply a result of uncontrolled cell division, but also the result of inadequate cell death.

Until recently, most of the information available on the genetics of cell death was derived from studies in the nematode *C. elegans* (Ellis, et al., 1986). As the focus has shifted to studies in mammalian cells, it appears that genes coding for intracellular inducers and suppressors of apoptosis have been well conserved throughout evolution.

Apoptosis appears to occur in different cell types as the result of three distinct pathways: (i) release, (ii) induction, and (iii) transduction. These can be distinguished from one another by their response to protein synthesis inhibitors. The release pathway has been described in undifferentiated PC-12 cells (Pittman, et al., 1993). Protein synthesis inhibitors stimulate apoptosis in these cells, suggesting that PC-12 cells constitutively express a protein that inhibits or blocks the apoptotic cascade. When this protein is removed (by adding cycloheximide), apoptosis is thought to occur through signalling pathways that are already in place. The molecular components of this pathway remain to be determined.

The induction pathway has been described in sympathetic neurons, septal cortical neurons, and a pheochromocytoma cell line, PC-12 (Garcia, et al., 1992; Svendsen, et al., 1994; Pittman, et al.). Protein synthesis inhibitors block apoptosis in these cells. For example, cell death in sympathetic neurons can be triggered by removal of nerve growth factor (NGF). If these cells are pretreated with cycloheximide, the effect of NGF withdrawal is already attenuated. This suggests that NGF withdrawal initiates "killer" gene expression and eventual production of "suicide proteins".

The transduction pathway has been described in killer T cells (Duke, et al., 1983). Here protein synthesis inhibitors have no effect. This suggests that apoptosis is stimulated and carried out by pathways that are already in place, e.g., by activation of specific protein kinases.

Bcl-2 is an integral inner mitochondrial membrane protein of relative molecular mass ~25 kDa and has been shown to protect certain cells against apoptosis (Hockenbery, et al., 1990) by acting as an antioxidant (Hockenbery, et al., 1993) (Bcl-2 functions as a repressor of cell death (Vaux, et al., 1988)). Studies have shown that Bcl-2 inhibits apoptosis initiated by cytokine withdrawal, and that Bax acts to override this action of Bcl-2 (Oltvai, et al., 1993).

It is now recognized that there exists a family of Bcl2-related proteins that have the effect of potentiating or attenuating apoptotic cell death (reviewed by J. C. Reed and by A. M. Davies). This family is specifically defined by two regions that share homology designated BH1, BH2, which participate in dimerization of the family members (Yin, et al., 1994 and Hanada, et al., 1995). Bcl-2 and Bax are the best understood members of this protein family. Bax (Oltvai, et al.), the prototypical family member involved in potentiating apoptotic cell death, heterodimerizes with two other members of the Bcl2-related protein family (Bcl2 and BclXL), and when overexpresses, counters the protective effect of these two family members (Oltvai, et al.; Boise, et al., 1993). Other members of the Bcl2-related protein family include Bad, Bak and Bag, as well as splice variants of all of the above.

Many of the family members, including Bcl2 and Bax, have a putative transmembrane domain at their carboxyl terminus that anchors the proteins to intracellular membranes, including mitochondrial, ER and nuclear membranes (Chen-Levy and Cleary, 1990; Krajewski, et al., 1993; Akao, et al., 1994). The bcl-2 gene encodes two proteins (26 kd and 22 kd) that differ in their carboxyl termini as a result of alternative splicing mechanisms (Tsujimotor and Croce, 1986; Tanaka, et al., 1993). The smaller form, designated Bcl2-β lacks the carboxyl terminus transmembrane domain and thus represents a soluble form of Bcl2 (Tanaka, et al.). Both the Bcl2-α and Bcl2-β proteins enhance tumorigenicity of fibroblast NIH-3T3 cells (Reed, et al., 1988) and both are able to malignantly transform rat embryo fibroblasts with the ras oncogene (Reed, et al., 1990). In contrast, Bcl2-β has been shown to neither prolong cell survival nor suppress apoptosis (Nguyen, et al., 1994). While membrane attachment is not necessarily required for its protective effect (Borner, et al., 1994), Bcl2-β does not possess all of the characteristics of the longer form.

The Bax gene has also been shown to encode for alternatively spliced variants (Oltvai, et al.). Four such variants have been identified. These include the original Bax-α, which encodes a 21 kd protein, Bax-β, the transcript for which contains all of intron 5 and encodes for a 24 kd protein lacking the carboxyl terminus due to a termination codon within the coding region of intron 5; Bax-β, which is missing exon 2 resulting in a 4.5 kd protein that prematurely terminates in exon 3 due to a translational frame shift; and Bax-δ (Apte, et al., 1995), which is missing exon 3 but retains the same translational frame, the BH1 and BH2 domains and the putative transmembrane domain.

Experiments performed in support of the present invention have led to the discovery and characterization of a novel splice variant of Bax, termed Bax-ω. Results of the experiments indicate that Bax-ω has unexpected effects on cell death and apoptosis which may be exploited in a variety of applications, such as those detailed below.

IV. Cloning and Expression of Bax-ω

A. Molecular Cloning of Bax-ω

Bax-ω was isolated by screening a human brain hippocampal cDNA library (Clontech, Palo Alto, Calif.) using polymerase chain reaction (PCR; Mullis; Mullis, et al.) with Bax PCR primers (BaxF—SEQ ID NO: 1; BaxR—SEQ ID NO: 21) as described in Example 1. Amplified DNA fragments were cloned into "BLUESCRIPT SK+" (Stratagene, La Jolla, Calif.), and the plasmid DNA was used to transform competent XL1-Blue MRF' cells (Stratagene).

Sequence analysis of Bax-ω clones identified as described in Example 1 revealed three groups of clones representing three different bax splice variants. The cDNAs comprising the first group (Bax 1) were nearly identical to the Bax-α transcript described by Oltvai, et al., while those of the second group (Bax 2) were missing exon 2 (like Bax-γ in Oltvai, et al.), resulting in transcripts 151 amino acids shorter than the Bax-α transcripts. The third group contained a novel class of transcripts termed Bax-ω.

A consensus nucleotide sequence (SEQ ID NO:8) of the Bax-ω cDNAs, as well as the translated amino acid sequence (SEQ ID NO:9), are presented in FIG. 1 with the 49 bp region underlined. Also shown in FIG. 1 are the relative locations of PCR primers, indicated by italics and/or lines above the sequence, and the location of an exemplary Bax-ω epitope (SEQ ID NO:18).

Based on the analysis described below, the novel 49 bp sequence was found to consist of the 3'-end 49 nucleotides of Bax intron 5. The presence of the sequence in the transcript results in a shift in the reading frame of Bax-ω in exon 6 relative to the reading frame of Bax-α in exon 6. A consequence of this shift is a difference in the amino acid sequences of the two transcripts in a region containing the same nucleotide sequence, and consequently, a change in the predicted secondary structure of the protein.

The difference between Bax-α and Bax-ω in the exon 6 reading frames is illustrated in FIG. 2, which shows the nucleotide sequence of Bax-ω beginning with the first (5') nucleotide of the 49 bp sequence, and including a portion of the sequence of exon 6. The nucleotide sequence is shown in the top row of each data set in FIG. 2, with the amino acid translations in the three reading frames shown beneath the nucleotide sequence. The amino acid sequence obtained using the first reading frame is that of Bax-ω, and is shown immediately beneath the nucleotide sequence in italicized characters. The amino acid sequence obtained using the second reading frame includes the portion of the Bax-α amino acid sequence corresponding to exon 6 (underlined).

Schematic diagrams of the Bax-ω cDNA and protein are shown in FIG. 3C for comparison with Bax-α (FIG. 3A) and Bax-β (FIG. 3B) cDNAs and proteins. The Bax gene is thought to be comprised of six exons and five introns (Oltvai, et al.). Bax-α transcripts are spliced to contain exons 1–6, and give rise to a 21 kD polypeptide containing sequences corresponding to the 3' portion of exon 1, all of exons 2–5, and the 5' portion of exon 6 (FIG. 3A). Bax-β transcripts (FIG. 3B) contain intron 5 in addition to exons 1–6, and give rise to a polypeptide containing sequences corresponding to the 3' portion of exon 1, all of exons 2–5, and the 5' portion of intron 5. Translation of the Bax-β polypeptide is terminated by a stop codon in intron 5 (see FIG. 2, underlined amino acid sequence).

Bax-ω transcripts result in a 24 kD polypeptide containing sequences corresponding to the 3' portion of exon 1, all of exons 2–5, the last (3') 49 bp of intron 5, and a portion of exon 6 (FIG. 3C).

FIGS. 3A, 3B and 3C also illustrate that Bax-α, Bax-β and Bax-ω differ only at their 3' (i.e., C-terminal) ends. In particular, the first (N-terminal) 158 amino acids of the proteins, corresponding to sequences in exons 1–5, are the same. The proteins diverge starting with amino acid number 159. The amino acid sequences in this region of Bax-α, Bax-β and Bax-ω are shown in FIG. 4. Note that the sequence of Bax-α between amino acids 159 and 192 corresponds to that underlined in FIG. 2, while the sequence of Bax-ω between amino acids 159 and 216 corresponds to that italicized in FIG. 2.

Figure 5B:
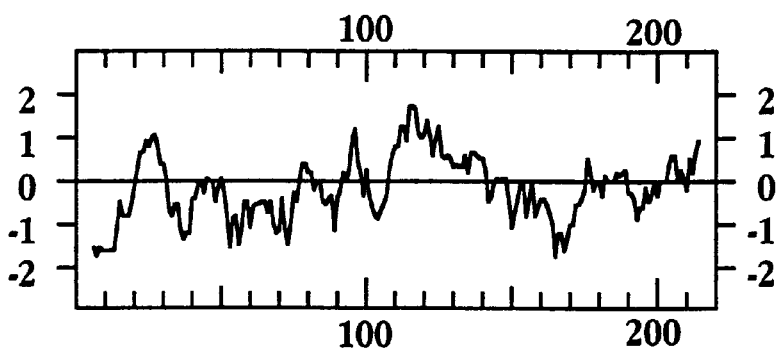
Figure 5C:
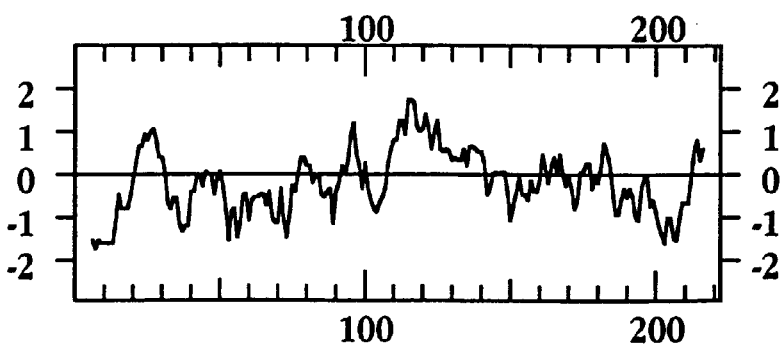

In particular, it will be appreciated that unlike Bax-α, Bax-ω does not possess a predicted transmembrane region or domain at the carboxyl terminus. Kyte-Doolittle hydrophobicity plots (Kyte and Doolittle) obtained using the predicted amino acid sequences of Bax-α, Bax-β and Bax-ω are shown in FIGS. 5A, 5B and 5C, respectively: note that while Bax-α has a hydrophobic domain at its carboxyl terminus, Bax-β and Bax-ω do not. Accordingly, recombinant proteins consisting of these sequences (i.e., SEQ ID NO:9) are soluble, and may be employed as "soluble" proteins in protein-protein binding assays described herein.

While Bax-ω does not contain a putative transmembrane domain at the carboxyl terminus, it does contain the BH1 and BH2 domains characteristic of proteins belonging to the Bcl2-related protein family. These domains enable Bax-ω to form heterodimers with other BLC2 family members.

The identity of the Bax-ω clones described above was confirmed by screening a human frontal cortex library with a Bax-ω probe, as described below in Example 1. This library was different from the one from which the original gene was cloned. Seven independent clones were obtained and sequenced. The sequence analysis showed that three of the clones contained nucleotides 71–800 of Bax-ω while the other four encoded Bax-α. These results strongly suggest that Bax-ω is a "real" transcript, and not a cloning artifact. RT-PCR analyses and protein expression data detailed below further support this interpretation.

B. Tissue Specificity of Bax-ω Expression

The pattern of Bax-ω expression was determined using RT-PCR as described in Example 2. The results indicate that Bax-ω is expressed in human brain, as well as in the tissues identified above. Example 2 also describes RT-PCR experiments to assess Bax-ω expression in a variety of rat tissues. The primers employed in the RT-PCR reactions were designed to amplify all of the know splice variants of Bax.

Figure 6A:
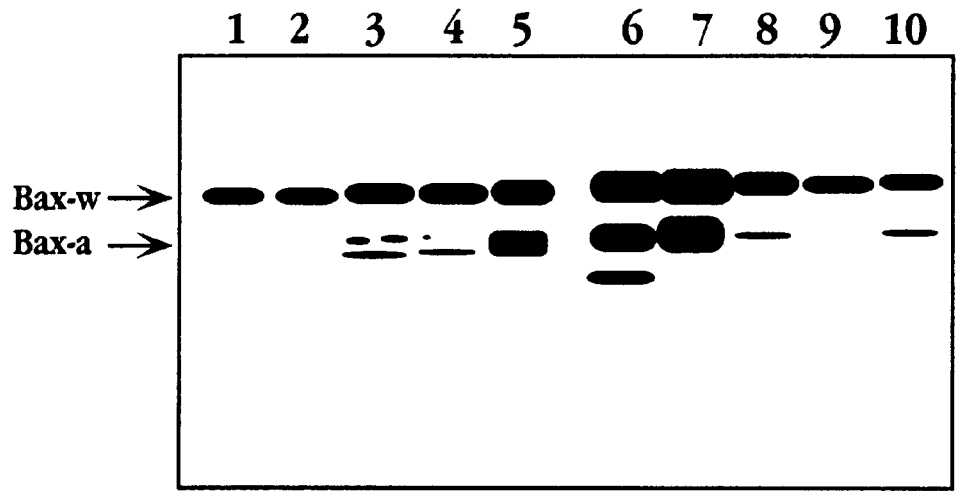
FIG. 6A shows the expression profile of bax-ω assessed using RT-PCR.
Figure 6B:
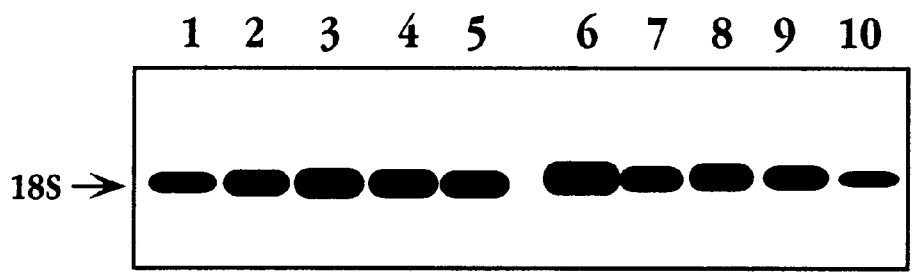
FIG. 6B is a quantitative control showing amplification of 18S rRNA from the same targets as were used in FIG. 6A.

The results are shown in FIG. 6A, with the identity of the tissue from which target cDNA was derived indicated in Example 2. At least two amplification products were detected in most of the tissues tested. The sizes of these amplification products correspond to the predicted sizes for the amplification products of Bax-α and Bax-ω. Subsequent digestion of each of the two bands with restriction endonucleases confirmed their identity as Bax-α and Bax-ω. FIG. 6B shows the results of an internal control amplification using glyceraldehyde 3 phosphate dehydrogenase.

Bax-ω was more prevalent than Bax-α mRNA in rate liver, lung, adrenal cortex, kidney, heart, skeletal muscle and brain, as well as human heart, liver and brain, including the thalamus, frontal cortex and hippocampus. These results suggest that Bax-ω is the predominant cytoplasmic form of Bax.

The predominance of Bax-ω over Bax-α could be due to preferential amplification of Bax-ω over Bax-α and/or to an increased amount of Bax-ω target cDNA over Bax-α target cDNA in samples. To address this question, different combinations of 6 primers corresponding to different 5' and 3' regions of all Bax forms were used to amplify cDNA from several different samples. Although some primers were less effective at amplifying the transcripts, Bax-ω was consistently the predominant message seen, suggesting that the tissues from which the samples were obtained contain more copies of Bax-ω mRNA than Bax-α mRNA.

Bax-ω expression may be further evaluated using other techniques, such as the in situ hybridization approach illustrated in Example 10. In Example 10, the expression of Bax-ω transcripts in sections of rat brain is assayed using labeled oligonucleotides corresponding to Bax-ω sequences. In particular, the expression pattern obtained using oligonucleotides directed against the exon 5/intron 5 junction of Bax-ω (SEQ ID NO:17) is compared to the expression of all members of the Bax family, obtained, for example, using oligonucleotides directed against sequences common to Bax-α, Bax-β, Bax-γ and Bax-ω, as well as sequences corresponding to Bcl-2.

Additional techniques for evaluating the tissue-specificity of expression include Northern blots, RNAse protection assays and the like (e.g., Ausubel, et al., 1988).

C. Production of Recombinant Polypeptides

Bax-ω polynucleotide sequences may be employed in the generation of chimeric genes containing DNA sequences from heterologous sources. For example, the polynucleotide sequences may be cloned into any of a variety of recombinant plasmids or vectors to generate Bax-ω recombinant proteins, facilitate subsequent manipulations and to provide means of delivering Bax-ω polypeptides to transfected cells. In particular, Bax-ω polynucleotide sequences may be cloned into any number of commercially available vectors to generate expression of the polypeptide in the appropriate host system. These systems include bacterial expression (e.g., pGEX; Smith and Johnson, 1988), baculovirus expression (Reilly, et al., 1982, Beames, et al., 1991; Clontech, Palo Alto Calif.), and expression in mammalian cells (Clontech, Palo Alto Calif.; Gibco-BRL, Gaithersburg Md.).

Such vectors, which are capable of expressing recombinant Bax-ω protein, typically contain control sequences, such as sequences containing promoter regions, enhancer elements, and the like, which are compatible with the selected host cell. These control sequences are operably linked to the insert sequence (i.e., Bax-ω polynucleotide sequence) such that the insert sequence can be expressed in the selected host cell. The expressed Bax-ω protein contains an amino acid sequence homologous or identical to SEQ ID NO:11 (Bax-ω insert amino acid sequence). The protein may, of course, include longer Bax-ω sequences, such as SEQ ID NO:13 or SEQ ID NO:8. A number of features can be engineered into the expression vectors, such as leader sequences which promote the secretion of the expressed sequences into culture medium.

Recombinant polypeptides may be expressed as fusion proteins or as native proteins. For example, the plasmid pGEX (Smith and Johnson) and its derivatives express the polypeptide sequences of a cloned insert fused in-frame with glutathione-S-transferase (GST). Recombinant pGEX plasmids may be transformed into appropriate strains of E. coli and fusion protein production can be induced by the addition of IPTG (isopropyl-thio galactopyranoside). Solubilized recombinant fusion protein can then the purified from cell lysates of the induced cultures using glutathione agarose affinity chromatography according to standard methods (Ausubel, et al.). An example of the production and purification of Bax-ω polypeptides using the GST fusion approach is illustrated in Example 3A, below.

Affinity chromatography may also be employed for isolating β-galactosidase fusion proteins (such as those produced by lambda gt11 clones). The fused protein is isolated by passing cell lysis material over a solid support having surface-bound anti-β-galactosidase antibody.

Isolated recombinant polypeptides produced as described above may be purified by standard protein purification procedures, including differential precipitation, molecular sieve chromatography, ion-exchange chromatography, isoelectric focusing, gel electrophoresis and affinity chromatography.

In addition to recombinant methods, Bax-ω proteins or polypeptides can be isolated from selected cells (e.g., brain cells) by affinity-based methods, such as by using appropriate antibodies (described below). Further, Bax-ω peptides may be chemically synthesized using methods known to those skilled in the art.

D. Biological Effects of Bax-ω Expression

It is generally believed that overexpression of Bax-α counteracts the cell death repressing activity of Bcl-2 and BclXL (Yin, et al.; Boise, et al.), and it has been proposed that the ratio of Bcl-2 to Bax determines survival or death following an apoptotic signal (Korsmeyer, et al., 1993). Site direct mutagenesis studies (Yin, et al.) have shown that mutations that disrupt the heterodimerization interaction of Bcl-2 with Bax but that still maintains the ability of Bcl-2 homodimerization completely abrogates the death repressor action of Bcl-2, suggesting that Bax alone or as a homodimer is responsible for death.

Experiments performed in support of the present invention and detailed below demonstrate that Bax-ω expression results in a suppression or repression of cell death. The experiments also suggest that this repression is mediated by an interaction between Bax-α Bax-ω.

1. Dimerization Results. The ability of Bax-α, Bax-ω and Bcl-2 to form homo- and hetero-dimers was studied using the yeast two hybrid protein-protein interaction system as described in Example 3, below.

The results of the assays, shown in Table 1, below, indicate that Bax-ω interacts with Bax-α as well as Bcl-2 interacts with Bax-α. Bax-ω did not however interact with either Bcl-2 or with itself, suggesting that, unlike Bcl-2 and Bax-α, Bax-ω does not homodimerize.

Figure 7:
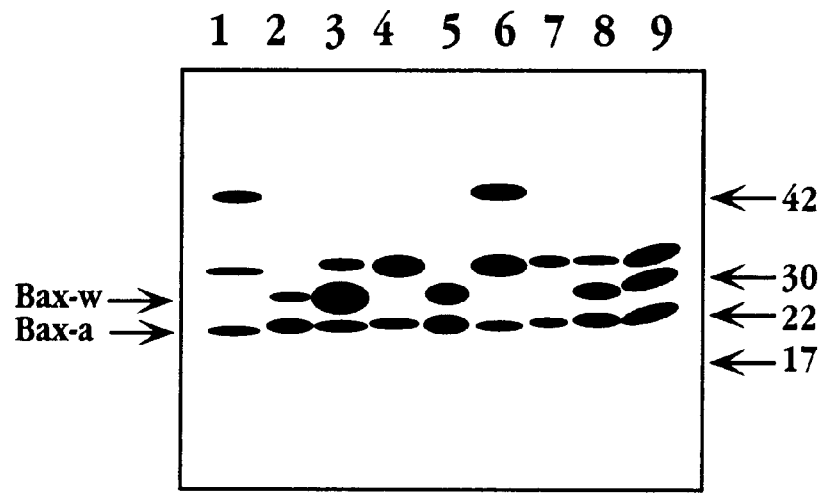
FIG. 7 shows a Western blot analysis of bax-ω expression in selected clones of Bax-ω-transfected L929 cells.

2. Stable Transfection of L929 Cells. An expression plasmid was constructed placing Bax-ω under the control of the CMV promoter in pcDNA3 (Invitrogen, San Diego, Calif.), as described in Example 4. The resultant pcDNA3-Bax-ω plasmid was stably transfected by electroporation into the mouse fibroblast cell line L929. Twenty four clonal cell lines were obtained and several were evaluated by Western analysis for the expression levels of Bax-ω protein using the anti-Baxα antibody, Bax P-19 (Santa Cruz Labs, Santa Cruz, Calif.) as well as anti-Baxω antiserum generated as described below. The results are shown in FIG. 7. Although the predicted molecular weight of Bax-ω is 24 kd, the translated product migrated at 28 kd, the same as that seen in an in vitro rabbit reticulocyte translation assay, suggesting that the protein is processed in a similar way in vivo as in vitro. As can be seen in FIG. 7, several of the transfected cell lines expressed Bax-ω protein. Note that neither parental L929 cells, vector-transfected L929 nor some of the ω-Bax transfected L929 cells expressed detectable levels of the protein using this antibody.

Figure 8:
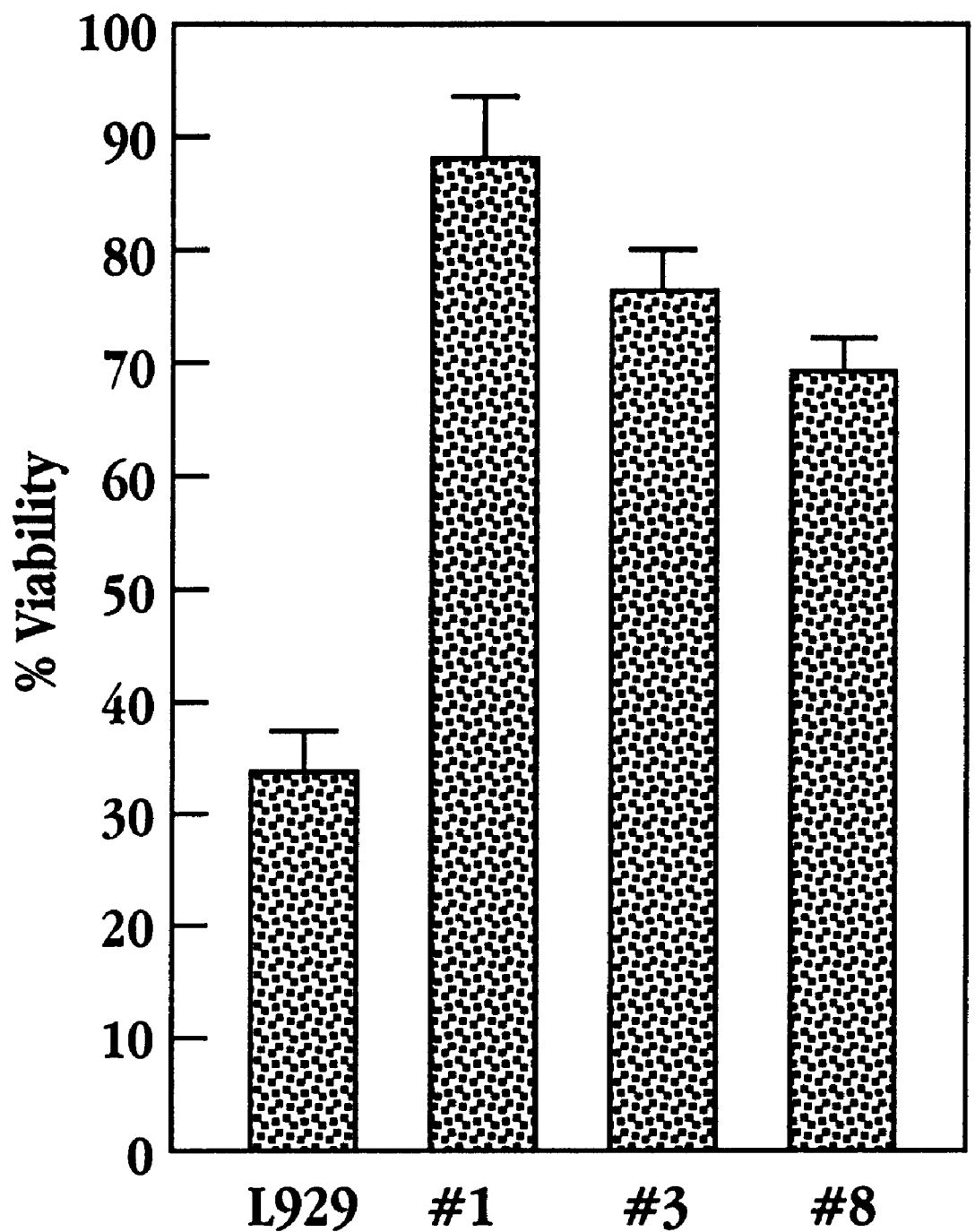
FIG. 8 shows the percent viability of vector-transfected and Bax-ω-transfected L929 cells in a TNF-induced apoptosis assay.

3. TNF-Induced Cell Death Assays. Tumor necrosis factor-induced cell death (Larrick and Wright, 1990; Talley, et al., 1995) was used to evaluate the effects of Bax-ω on apoptosis, as detailed in Example 5. Vector-transfected L929 or Bax-ω-transfected cells (as described above) were treated with TNF (40 ng/ml) and cycloheximide (10 μg/ml) for 12 hr. Cell death was measured using the technique of trypan blue exclusion. The results are shown in FIG. 8. Al of the three cell lines tested (pcDNA3Bax-ω#1, pcDNA3Bax-ω∩3 and pcDNA3Bax-ω∩8) showed increased viability relative to the vector-transfected control.

Figure 9:
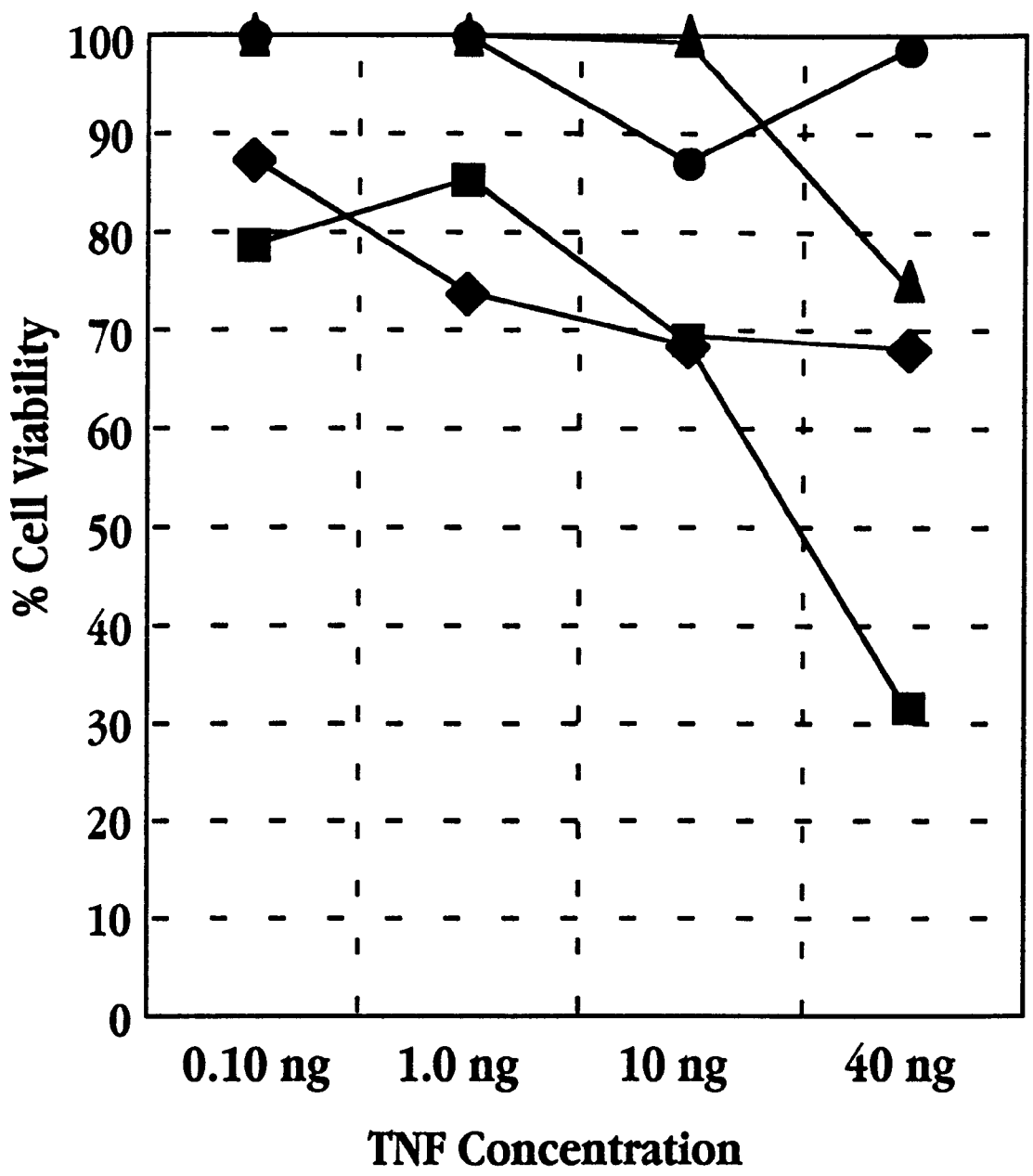
FIG. 9 shows the percent viability of vector-transfected and Bax-ω-transfected L929 cells as a function of TNF concentration in a TNF-induced apoptosis assay.

A dose response curve, shown in FIG. 9, was generated for the vector-transfected L929 cells and the three clonal cell lines described in FIG. 8. The concentration of cycloheximide remained the same for each condition with the concentration of TNF varying from 100 pg/ml to 40 ng/ml. The difference between the vector only-transfected L929 cells and the Bax-ω-transfected cells is very apparent at the higher doses of TNF.

A time course was performed to determine the duration of the protective effects of Bax-ω following treatment with 40 ng/ml. The results, shown in FIG. 10, indicate that Bax-ω is protective up to 12 hr following treatment. After 20 hr, the majority of cells have died, probably as a result of cycloheximide that prevents the ongoing translation of protective proteins.

In summary, the TNF-induced apoptosis data indicate that expression of Bax-ω protein protects cells from TNF-induced cell death via a mechanism that may involve the interaction of Bax-ω with Bax-α.

V. Diseases Involving Abnormal Cell Proliferation

A number of diseases involve abnormal cell proliferation. Cancer is the most obvious of these. Types of cancer include lung, colon-rectum, breast, prostate, urinary tract, uterus, lymphoma, oral, pancreas, leukemia, melanoma, stomach, ovary and glioma. Cancer typically originates from a single stem cell which proliferates to form a clone of malignant cells, termed a "tumor". Cells comprising or derived from such a tumor are termed "tumor cells".

A number of other diseases involve abnormal nonmalignant proliferation of cells. They include, among others, atherosclerosis pulmonary fibrosis, primary pulmonary hypertension, neurofibromatosis, acoustic neuroma, tuberous sclerosis, psoriasis, keloid, fibrocystic breast, polycystic ovary, polycystic kidney, scleroderma, rheumatoid arthritis, ankylosing spondylitis, myelodysplasia, some anemias, cirrhosia, esophageal stricture, sclerosing cholangitis and retroperitoneal fibrosis. Many of the above conditions involve an abnormally high level of cell proliferation. Cells having such an abnormally high level of proliferation are referred to herein as "rapidly proliferating" cells.

VI. Applications of Bax-ω Polynucleotides and Polypeptides

A. Use of Bax-ω Polynucleotides

1. Screening Applications. Bax-ω polynucleotides of the present invention may be used as probes for detecting Bax-ω mRNA in selected tissues, or for measuring levels of Bax-ω mRNA under selected pathological conditions (e.g., Parkinson's or Alzheimer's diseases, ischemia-related diseases, and the like).

Bax-ω nucleic acid sequences may be used as diagnostic agents for the quantitation and detection of Bax-ω sequences present in an mRNA-containing sample. The level of Bax-ω mRNA contained in the sample may be correlated with the apoptotic state of the cells reflected in the sample. For example, a brain tumor biopsy sample may contain relatively high levels of Bax-ω mRNA while a sample from a portion of the CNS undergoing degeneration may contain relatively low levels of Bax-ω message. Such diagnostic measurements may also be used to identify circumstances when a treatment method of the present invention may be particularly effective. For example, high levels of Bax-ω message in a tumor may indicate that administering Bax-ω antisense compositions or anti-Bax-ω antibodies to the tumor and/or decreasing expression of Bax-ω in the tumor may inhibit the growth of the tumor. Similarly, low levels of Bax-ω expression in neuronal tissue undergoing degeneration may indicate that increasing the level of Bax-ω production and/or functional expression in the tissue may have a neuroprotective effect in the tissue.

In one diagnostic configuration, the sample is reacted under PCR or RT-PCR conditions using primers where one upstream primer is specific for Bax-ω insert sequence (e.g., Jnct; SEQ ID NO:15), and the other upstream primer corresponds to a region of Bax cDNA contained in all the isoforms (e.g., Bax 462 F; SEQ ID NO:4). Bax RI (SEQ ID NO:2) could be employed as the reverse primer for both reactions. The amplification products from such an amplification reaction can be size-fractionated on a gel, and the product corresponding to Bax-ω (as opposed to Bax-α, Bax-β and Bax-γ) can be readily identified (e.g., as in Example 2).

Alternatively, probes (such as an oligonucleotide having a sequence complementary to SEQ ID NO:10) can be derived from the Bax-ω sequences of the present invention. These probes can then be labeled with reporter moieties and used as hybridization probes against nucleic acids present in a sample obtained from a test individual. The probes can be labeled using a variety of reporter molecules and detected accordingly: for example, radioactive isotopic labeling and chemiluminescent detection reporter systems (Tropix, Bedford, Mass.).

The labeled probes may be hybridized to samples being tested using standard hybridization procedures. Typically, polynucleotides isolated from a sample are immobilized or "blotted" on nylon or nitrocellulose membranes (available, e.g., from Schleicher & Schuell, Keene, N.H.). Variations of such blots include Northern blots, dot blots and slot blots. The membranes containing the immobilized polynucleotides are then washed in a pre-hybridization solution and are incubated at a controlled temperature in a hybridization solution containing the probe. Following hybridization, the membranes are washed under conditions effective to result in the desired degree of hybridization specificity. Such hybridization and wash conditions and procedures are well known in the art (e.g., Ausubel, et al.; Sambrook, et al., 1989).

For example, Unit 6.3 of Ausubel, et al., provides two protocols for hybridization using DNA fragments greater than about 50 bp as probes—hybridization in formamide and hybridization in aqueous solution. While it is understood that the lower the salt concentration, the higher the stringency, both protocols alter the stringency of hybridization primarily by the wash temperature.

The initial (low stringency) wash is typically performed at room temperature and the high-stringency wash is determined empirically, with the relative homology between the probe and target sequence as a determining parameter. If the homology is 100%, a high temperature (65–75° C.) can be used. As the homology drops, lower washing temperatures are used. In general, high-stringency washing is initiated at 37–40° C. and the temperature is raised by 3–5° C. intervals until background is low enough not to be a major factor in the detection (e.g., autoradiography). Probes less than about 100 bp are washed at lower temperatures, even if the homology is 100%.

Unit 7.4 of Ausubel, et al. provides two protocols for hybridization using synthetic oligonucleotides 14 or more bp in length as probes—hybridization in sodium chloride/sodium citrate (SSC) and hybridization in tetramethylammonium chloride (TMAC). The melting temperature of oligonucleotides of different lengths in SSC and TMAc is given in FIG. 6.4.1 of Ausubel, et al.

In the SSC protocol, temperatures are provided for hybridization and wash conditions for oligonucleotides, 14, 17, 20 and 23 basepairs in length. The signal-to-noise ratio is optimized by washing the hybridized filters at an empirically determined temperature. Initial hybridization and stringent washing conditions can be determined by formulas (Lathe, 1985) and improved upon by trial-and-error adjustments. Generally, probes greater than about 50 bp long that have more than about 80% homology are specific and hybridize to the sequence of interest.

In the TMAC protocol, suing both hybridization and wash temperatures in the range of 5–10° C. below the melting temperature (Tm) for an oligonucleotide of particular length gives optimal results.

The hybridization probe may either contain a directly-detectable reporter moiety or label (e.g., a radiolabeled probe), or it may contain a tag or label that is specifically detected by a secondary reporter after completion of the hybridization reaction. For example, oligonucleotide probes may be fashioned to contain nucleotides derivatized with, for example, biotin or digoxigenin. These molecules may be detected after the hybridization reaction using streptavidin or anti-digoxygenin antibodies, respectively, linked to a secondary reporter, such as a fluorescent molecule or alkaline phosphatase. Methods for performing these operations are well known (e.g., Ausubel, et al.) and the reagents are widely available and may be conveniently obtained in the form of kits with detailed instructions (e.g., from Boehringer Mannheim, Indianapolis, Ind.).

Detection of specifically-hybridized probes through detection of the reporter moiety is performed according to standard methods (Ausubel, et al.) and/or following the protocols supplied by the manufacturer of the reporter system being used. The amount of specifically-hybridized probe, as determined by measuring relative amount of reporter, is proportional to the amount of Bax-ω polynucleotide immobilized on the solid substrate (e.g., nylon or nitrocellulose membrane).

Further, the Bax-ω sequences described herein may be used to isolate additional members of the Bax-ω family, both in human and in other organisms. Probes directed to Bax-ω (e.g., directed to the sequence represented as SEQ ID NO:10) may be employed in screens of cDNA libraries to isolate such related transcripts using standard methods and protocols (e.g., Ausubel, et al.; Sambrook, et al.). For example, the sequences disclosed herein, particularly the exon 5/intron 5 junction (SEQ ID NO:17) or the 49 nucleotide Bax-ω insert sequence (SEQ ID NO:10), may be used to screen a cDNA library from a selected tissue (e.g., human hippocampus) to isolate DNA fragments encoding Bax-ω as described herein.

Positive clones (i.e., clones containing polynucleotide sequences that selectively hybridize with the probe) are identified by detecting the reporter moiety on the probe (e.g., autoradiography to detect a radiolabeled probe), isolated, and used to generate purified nucleic acids containing the selectively-hybridizing sequences using standard methods (plasmid preps, phage purification, etc.). The sequences may then be restriction mapped and/or sequenced to determine the identity of the inserts.

Libraries may be conveniently purchased from commercial sources (for example, Clontech (Palo Alto, Calif.), or may be made by one skilled in the art using known methods and protocols (e.g., Ausubel, et al.; Sambrook, et al.). Methods for the screening of libraries are described herein and are known to those skilled in the art (e.g., Ausubel, et al.; Sambrook, et al.). Further, suitable protocols for screening may also typically be obtained from the suppliers of commercial cDNA libraries.

Alternatively, Bax-ω polynucleotides may be amplified using reverse transcriptase (RT) polymerase chain reaction (PCR; Mullis; Mullis, et al.) employing a suitable mRNA source. Example 1, detailed below, describes the PCR amplification of Bax-ω polynucleotides from human hippocampal cDNA. The PCR primers were designed to amplify the full length Bax cDNA, based on the human Bax sequence of Oltvai, et al. DNA fragments amplified using PCR may be purified and cloned into a suitable vector for further characterization, such as restriction mapping and sequencing. In Example 1, the amplification products were cloned into the plasmid "BLUESCRIPT SK+" (Stratagene, La Jolla, Calif.).

2. Therapeutic Applications—Antisense. Therapeutic application of polynucleotides and related compositions derived from Bax-ω sequences include methods of altering apoptosis in cells. According to the teachings herein, apoptosis in cells may be altered by altering the production or functional expression of bax-ω in those cells. One approach to inhibiting the production of Bax-ω is through the use of polymer anti-sense compositions directed against Bax-ω. In particular, antisense compositions effective to specifically hybridize with the Bax-ω insert sequence (SEQ ID NO:17) are contemplated for applications where it is desired to maintain the normal expression of Bax-α, but to inhibit expression of full-length Bax-ω.

Exemplary antisense compositions are polynucleotides (e.g., oligonucleotides), preferably phosphorothioate (PS) polynucleotides, whose sequence is the reverse complement of SEQ ID NO:17 or portion thereof. A particularly suitable antisense composition is directed against the sequence represented as SEQ ID NO:15 (the "splice junction" primer, Jnct) or portion thereof (e.g., a PS polynucleotide having a sequence that is the reverse complement of SEQ ID NO:15). An exemplary antisense sequence, which is the reverse complement of SEQ ID NO:15, is presented herein as SEQ ID NO:16. Phosphothiorate oligonucleotides are especially suitable for use with the present invention, because they typically (i) are stable in vivo, (ii) can enter and be retained by the target cell. In part due to these characteristics, PS oligonucleotides have performed with considerable success in animal models of leukemia and in treating HIV, influenza and herpes viral infections (reviewed in Stein, et al., 1993).

The success of PS oligonucleotides in therapeutic applications is attributed in part to the fact that replacing one oxygen with a sulfur in each phosphate of the DNA backbone renders the oligonucleotide resistant to serum and intracellular nucleases (Heidenreich, et al., 1995). Accordingly, PS oligonucleotides are relatively stable in vivo when injected either subcutaneously or intravenously. Upon entering the blood stream, PS oligonucleotides are rapidly internalized by a variety of cell types, either by adsorptive endocytosis or fluid-phase pinocytosis. In some instances, the oligonucleotides have even been shown to localize to the nucleus and mitochondria.

Antisense compositions such as described above may be used in a treatment method to promote apoptosis in a cell (e.g., a tumor or other abnormally-proliferating cell). In the method, a cell is treated with an amount of a polymer antisense composition (such as described above) effective to significantly inhibit translation of Bax-ω mRNA in that cell.

Bax-ω polynucleotide compositions such as are described above may also be employed in a method of altering the ratio of other Bax transcripts (such as Bax-α) to Bax-ω in a cell expressing a pre-spliced Bax-ω transcript. This method includes administering to the cell a composition which affects the splicing of one or both Bax transcripts. Examples of such compositions include ones which interact with a splicing factor. For instance, the composition may be an oligonucleotide homologous to a splice site in the Bax-ω transcript (e.g., an oligonucleotide having the sequence represented as SEQ ID NO:17). Such an oligonucleotide may act as a competitive inhibitor of the splicing factor, reducing the relative number of correctly-spliced Bax-ω transcripts in cells containing the oligonucleotide.

3. Therapeutic Applications—Gene Therapy. Chimeric gene constructs of the present invention (e.g., expression vectors) containing Bax-ω polynucleotide sequences may be used in gene therapy applications to achieve expression of Bax-ω polynucleotide sequences in selected target tissues. Gene therapy applications typically involve identifying target host cells or tissues in need of the therapy, designing vector constructs capable of expressing a desired gene product in the identified cells, and delivering the constructs to the cells in a manner that results in efficient transduction of the target cells.

The tissues targeted by gene therapy are typically those that are affected by the disease that the vector construct is designed to treat. For example, in the case of cancer, the targeted tissues are malignant tumors.

Any of a number of different vectors may be employed in gene therapy applications. Such vectors typically contain polynucleotide elements which facilitate the transfer and expression of the vectors in the host cells. These elements differ depending on the vector system being employed and are known to those of skill in the art.

Similarly, any of a variety of methods known to those skilled in the art may be used to introduce chimeric genes of the present invention into such target tissue cells. The vectors may be introduced either ex vivo (where the cells to be transfected are first removed from the subject to be treated) or in vivo, and may result in transient or stable expression on the gene product. Methods of introducing the vectors include viral-based approaches and nonviral approaches, such as lipofection, ligand-DNA conjugates and direct injection of naked DNA (see, e.g., reviews by Anderson, 1992; Miller, 1992; or Mulligan, 1993).

In the case of viral-mediated gene transfer, host cells are transfected with chimeric genes of the present invention by infection with mature virions containing hybrid vectors (the chimeric genes along with selected viral sequences). The virions used to transfect host cells are preferably replication-defective, such that the virus is not able to replicate in the host cells.

The virions may be produced by co-infection of cultured host cells with a helper virus. Following coinfection, the virions are isolated (e.g., by cesium chloride centrifugation) and any remaining helper virus is inactivated (e.g., by heating). The resulting mature virions contain a chimeric gene of the present invention and may be used to infect host cells in the absence of helper virus. Alternatively, high titers of replication-defective recombinant virus, free of helper virus, may be produced in packaging cell lines containing those components for which the virus is defective (Miller, 1990).

Several types of viruses, including retroviruses, adeno-associated virus (AAV), herpes virus, vaccinia virus, and several RNA viruses may be amenable for use as vectors with chimeric gene constructs of the present invention. Each type of virus has specific advantages and disadvantages, which are appreciated by those of skill in the art. For example, retroviral and AAV vectors are more suitable for stable transfection than are adenovirus, vaccinia virus or polio virus vectors. Methods for manipulating viral vectors are also known in the art (e.g., Grunhaus and Horowitz, 1992; Hertz and Gerard, 1993; and Rosenfeld, et al., 1992).

Retroviruses, like adeno-associated viruses, stably integrate their DNA into the chromosomal DNA of the target cell. Unlike adeno-associated viruses, however, retroviruses typically require replication of the target cells in order for proviral integration to occur. Accordingly, successful gene transfer with retroviral vectors depends on the ability to at least transiently induce proliferation of the target cells.

Retroviral vectors are attractive in part due to the efficiency of transfection—some vectors can stably transduce close to 100% of target cells. The use of retroviral vectors for in vivo gene therapy has been limited, in part, by the requirement of appropriate viral receptors on the target cell. Because the identities of most retroviral receptors are unknown, it has not been possible to determine the distribution of receptors in different cell types. Accordingly, the targeting of specific cell types by retroviral vectors has in many cases proven problematic.

This difficulty may be circumvented by modifying the envelope protein of the retrovirus to contain a ligand for a known endogenous (not necessarily viral) receptor expressed on the target cells. An application of this technique is described in detail by Kasahara (1994). Preferably, the virus also contains an unmodified envelope protein to facilitate cell entry.

Adeno-associated viruses are capable of efficiently infecting nondividing cells and expressing large amounts of gene product. Furthermore, the virus particle is relatively stable and amenable to purification and concentration. Replication-defective adenoviruses lacking portions of the E1 region of the viral genome may be propagated by growth in cells engineered to express the E1 genes (Jones and Shenk, 1979; Berkner, 1988; Graham and Prevea, 1991). Most of the currently-used adenovirus vectors carry deletions in the E1A–E1B and E3 regions of the viral genome. A number of preclinical studies using adenoviral vectors have demonstrated that the vectors are efficient at transforming significant fractions of cells in vivo, and that vector-mediated gene expression can persist for significant periods of time (Rosenfeld, et al.; Quantin, et al., 1992; Stratford-Perricaudet, et al., 1992a; Rosenfeld, et al.; Stratford-Perricaudet, et al., 1992b; Jaffe, et al., 1992).

Herpes virus vectors (Breakefield and DeLuca, 1992; Freese, et al., 1990) are particularly well suited for the delivery and expression of foreign DNA in cells of the central nervous system (CNS), since they can efficiently infect mature, postmitotic neurons. Methods for manipulating the vectors and transfecting CNS cells are well known (see, e.g., Kennedy and Steiner, 1993; Yung, 1994). A number of studies describe methods for transplanting genetically modified cells into different regions of the brain (Malin, et al., 1989, 1992; Rossi and Sarver, 1992; Sullenger, et al., 1991; Chatterjee, et al., 1992; Hope, et al., 1992). Studies utilizing direct injection of vectors into CNS tissue have also been performed (e.g., Zhang, et al., 1992).

Plasmids or vectors bearing chimeric genes of the present invention may be purified and injected directly into a target tissue, using "naked DNA injection". Further, liposomes may be employed to deliver genes to target tissues using methods known in the art. The liposomes may be constructed to contain a targeting moiety or ligand, such as an antigen, an antibody, or a virus on their surface to facilitate delivery to the appropriate tissue. The liposomes may also be surface-coated, e.g., by incorporation of phospholipid-polyethyleneglycol conjugates, to extend blood circulation time and allow for greater targeting via the bloodstream. Liposomes of this type are well known.

Receptor-mediated endocytic pathways for the uptake of DNA may permit the targeted delivery of genes to specific cell types in vivo. Receptor-mediated methods of gene transfer involve the generation of complexes between plasmid DNA and specific polypeptide ligands (Wu, 1991) that can be recognized by receptors on the cell surface. One of the problems with receptor-mediated uptake for gene delivery is that the endocytic vesicles formed during this process may be transported to the lysosome, where the contents of the endosome are degraded. Methods have been developed to facilitate escape of the DNA from the endosome during the course of its transport. For example, either whole adenovirus (Wagner, et al., 1992a; Christiano, et al., 1993) or fusogenic peptides of the influenza HA gene product (Wagner, et al. 1992b) may be used to induce efficient disruption of DNA-containing endosomes.

In cases such as those outlined above, where a vector may be targeted to selectively transfect a specific population of cells, it will be understood that in addition to local administration (such as may be achieved by injection into the target tissue), the vector may be administered systemically (e.g., intravenously) in a biologically-compatible solution or pharmaceutically acceptable delivery vehicle. Vector constructs administered in this way may selectively infect the target tissue or may be designed to be selectively expressed in a target tissue (e.g., by way of a tissue-specific promoter).

Example 4 details the construction of a Bax-ω expression vector (pcDNA3-bax-ω) which exemplifies the utility of the present invention for gene therapy applications. The vector, which contains an insert encoding Bax-ω, was used to transform mouse fibroblast L929 cells. The transformed cells had significantly lower levels of cell death in a TNF-induced apoptosis assay (Example 5).

B. Use of Bax-ω Polypeptides

1. Screening Applications. Bax-ω polypeptides (e.g., isolated as described above) may be used in a number of applications. For example, the polypeptides may be used in a method of identifying compounds capable of affecting the binding of Bax-ω to a partner of Bax-ω (PB-ω), e.g., Bax-α. The method includes contacting the partner with Bax-ω in the presence and absence of a test compound, measuring the effect of the test compound on the extent of binding between the partner and Bax-ω, and identifying the test compound as effective if its measured effect on the extent of binding is above a threshold level (e.g., a several-fold difference in binding level between control and experimental samples). The effect on binding may be (i) an inhibition of binding, or (ii) a potentiation of binding.

Any of a number of different methods may be used to screen for compounds effective to disrupt the interaction of Bax-ω and its partner. For example, a biochemical assays may be employed, whereby one of the two interacting proteins (e.g., PB-ω) is expressed as a GST-fusion protein, immobilized on beads, and is reacted with the second of the two interacting proteins (i.e., Bax-ω), which is free in solution, in the presence and absence of a test compound. This method is presented in detail in Example 3, below.

To identify a compound capable of affecting binding between Bax-ω and PB-ω, a test compound is included in the solution (containing the "free" soluble protein; e.g., Bax-ω) that is contacted with the immobilized protein (e.g., PB-ω). The amount of bound Bax-ω is detected and compared to the amount bound under similar conditions in the absence of the test compound (control). If the compound has a significant effect on the binding of the Bax-ω to its partner (i.e., if the compound significantly increases or significantly decreases the binding), and the effect exceeds a threshold value (which is set to a desired level by the practitioner of the invention; e.g., several-fold increase or several-fold decrease in binding), the compound is identified as effective to affect or alter the binding of Bax-ω to its partner.

The amount of soluble protein bound to its immobilized "partner" protein may be assayed in a number of different ways, including a Western-blot or dot-blot approach, a multiwell plate enzyme linked immunosorbent assay (ELISA) approach, two-hybrid β-Gal assay and the like. Detection methods useful in such assays include antibody-based methods (i.e., an antibody directed against the "free" protein), direct detection of a reporter moiety incorporated into the "free" protein (such as a fluorescent label), and proximity energy transfer methods (such as a radioactive "free" protein resulting in fluorescence or scintillation of molecules incorporated into the immobilized protein or the solid support).

In particular, as discussed in the scintillation proximity assay in Example 3D, multiwell plates (e.g., 96-well plates) that contain a scintillating material in the wells (available from, e.g., Wallac, Gaithersburg, Md.) may coated with the immobilized protein and used in conjunction with radioactively-labeled free protein. Free protein that binds the immobilized protein is constrained within a few nanometers of the well surface, resulting in light emission from the scintillation material in the wells. The signal can be quantitated using a plate reader or counter, such as the "MICRO-BETA PLUS" plate counter (Wallac), to generate standard binding plots.

For example, as is discussed in Example 3C, a partially-purified (e.g., by the GST methods) partner of Bax-ω (e.g., Bax-α polypeptide) may be attached to the bottoms of wells in a multiwell plate (e.g., 96-well plate) by introducing a solution containing the polypeptide into the plate and allowing the polypeptide to bind to the plastic. The excess peptide-containing solution is then washed out, and a blocking solution (containing, for example, bovine serum albumin (BSA)) is introduced to block non-specific binding sites. The plate is then washed several more times and a solution containing Bax-ω and, in the case of experimental (vs. control) wells, a test compound added.

Different wells may contain different test compounds, different concentrations of the same test compound, different concentrations of Bax-ω or its partner, and the like. Further, it will be understood that various modifications to this detection scheme may be made. For example, the wells may be precoated with substance(s) that enhance attachment of the protein to be immobilized and/or decrease the level of non-specific binding. For example, the wells may be derivatized to contain glutathione and may be pre-coated with BSA, to promote attachment of the immobilized protein in a known orientation with the binding site(s) exposed.

It will be understood that various modifications of the above-described assay are included within the scope of the present invention. For example, the roles of the proteins can be switched—that is, Bax-ω may be immobilized to the solid support and a solution containing a soluble partner of Bax-ω (e.g., Bax-α) may be contacted with the Bax-ω. Additionally, the immobilized protein or the free protein may be exposed to a test compound prior to the binding assay, and the effects of this pre-exposure may be assessed relative to controls. Alternatively, the test compound may be added subsequent to the mixing of the two interacting proteins.

The yeast two-hybrid protein interaction assay may be employed to identify a partner of Bax-ω, and subsequently to identify compounds that affect the binding of that partner to Bax-ω. The assay is based on the finding that most eukaryotic transcription activators are modular (e.g., Brent, et al., 1985), i.e., that the activators typically contain activation domains that activate transcription, and DNA binding domains that localize the activator to the appropriate region of a DNA molecule.

In a two hybrid system, a first fusion protein contains one of a pair of interacting proteins fused to a DNA binding domain, and a second fusion protein contains the other of a pair of interacting proteins fused to a transcription activation domain. The two fusion proteins are independently expressed in the same cell, and interaction between the "interacting protein" portions of the fusions reconstitute the function of the transcription activation factor, which is detected by activation of transcription of a reporter gene.

At least two different cell-based two hybrid protein-protein interaction assay systems have been used to assess binding interactions and/or to identify interacting proteins. Both employ a pair of fusion hybrid proteins, where one of the pair contains a first of two "interacting" proteins fused to a transcription activation domain of a transcription activating factor, and the other of the pair contains a second of two "interacting" proteins fused to a DNA binding domain of a transcription activating factor.

The yeast GAL4 two hybrid system (Fields and Song, 1989; Chien, et. al., 1991; Durfee, et al., 1993; Bartel, et al., 1993) was developed to detect protein-protein interaction based on the reconstitution of function of GAL4, a transcriptional activator from yeast, by activation of a GAL1-lacZ reporter gene. Like several other transcription activating factors, the GAL4 protein contains two distinct domains, a DNA binding domain and a transcription activation domain. Each domain can be independently expressed as a portion of a fusion protein composed of the domain, and a second, "bait" interacting protein. The two fusion proteins are then independently expressed together in a cell. When the two GAL4 domains are brought together by a binding interaction between the two "interacting" proteins, transcription of a reporter gene under the transcriptional control of GAL4 is initiated. The reporter gene typically has a promoter containing GAL4 protein binding sites (GAL upstream activating sequences, $UAS_G$).

A second two hybrid system, described in detail in Ausubel, et al. utilizes a native $E.$ $coli$ LexA repressor protein which binds tightly to appropriate operators. A plasmid is used to express one of a pair of interacting proteins (the "bait" protein) as a fusion to LexA.

The plasmid expressing the LexA-fused bait protein is used to transform a reporter strain of yeast, such as EGY48. In this strain, binding sites for LexA are located upstream of two reporter genes. In the first reporter system, the upstream activation sequences of the chromosomal LEU2 gene— required in the biosynthetic pathway for leucine (Leu)—are replaced in EGY48 with lexA operators, permitting selection for viability when cells are plated on medium lacking Leu. In the second reporter system, EGY48 harbors a plasmid, pSH18–34, that contains a lexA operator-lacZ fusion gene, permitting discrimination based on color when the yeast is grown on medium containing Xgal (Ausubel, et al.).

LexA and GAL4 each have different properties that should be considered when selecting a system. LexA is derived from a heterologous organism, has no known effect on the growth of yeast, possesses no residual transcriptional activity, can be used in GAL4⁺ yeast, and can be used with a Gal-inducible promoter. Because GAL4 is an important yeast transcriptional activator, experiments are performed in gal4 yeast strains to avoid background from endogenous GAL4 activating the reporter system. Both two hybrid systems have been successfully used for isolating genes encoding proteins that bind a target protein and as simple protein binding assays (e.g., Yang, et al., 1992; Gyuris, et al., 1993), and both can be applied to the identification a partner of Bax-ω as well as to the identification of compounds capable of affecting binding of Bax-ω to its partner, as described below.

As stated above, the yeast two-hybrid assays may be employed to isolate protein partners of Bax-ω (i.e., proteins that can interact with Bax-ω). A convenient DNA source for the isolation of a Bax-ω "partner" (PB-ω) is a DNA library, such as a brain cDNA library. To screen a library with the LexA system, the library uses the inducible yeast GAL1 promoter to express proteins as fusions to an acidic domain ("acid blob") that functions as a portable transcriptional activation motif ("act"), and to other useful moieties. Expression of library-encoded proteins is induced by plating transformants on medium containing galactose (Gal), so yeast cells containing library proteins that do not interact specifically with the bait protein fail to grow in the absence of Leu. Yeast cells containing library proteins that interact with the bait protein form colonies within 2 to 5 days, and the colonies turn blue when the cells are streaked on medium containing Xgal. The plasmids are isolated and characterized by a series of tests to confirm specificity of the interaction with the initial bait protein. Those found to be specific are ready for further analysis (e.g., sequencing).

Experiments performed in support of the present invention and detailed in Example 3, below, demonstrate the interaction of Bax-ω with partners of Bax-ω using a yeast two hybrid system. The full length Bax-ω cDNA was cloned into yeast two-hybrid vectors and was tested for interaction with human Bcl-2, Bax-α and Bax-ω by both HIS selection and X-gal filter assays as described in Example 3. The results are shown in Table 1. Bax-ω interacted with Bax-α as well as the positive control of Bcl-2/Bax-α interaction. Bax-ω did not however interact with either Bcl-2 or with itself, suggesting that, unlike Bcl-2 and Bax-α, Bax-ω does not homodimerize.

A two hybrid system such as is described above may be used to identify compounds effective to disrupt the binding of Bax-ω and a partner of Bax-ω (PBω) as follows. A polynucleotide encoding PBω is fused to the GAL4 DNA binding domain (G4BD) in a yeast expression vector (e.g., pG4BD-PBω). The vector is used to generate yeast cells harboring pG4BD-PBω and a GAL4-activated reporter gene (e.g., LacZ). These cells are then transformed with a vector carrying a fusion between the transcription activating domain of yeast GAL4 (G4AD) and Bax-ω (e.g., pG4AD-Bax-ω). Transformants are screened (e.g., using a β-galactosidase (β-gal) assay on plates containing the chromogenic substrate X-gal) for expression of the reporter. Reporter-expressing cells are selected, cloned, and used to screen test compounds. Compounds which increase or decrease reporter expression relative to a user-defined threshold (e.g., several-fold increase or decrease) are identified as affecting binding of PBω and Bax-ω, and may be further evaluated. e.g., as described below, for effects on apoptosis in vitro and in vivo.

2. Anti-Bax-ω Antibodies. Bax-ω polypeptides of the present invention, particularly polypeptides comprising Bax-ω antigens, may be used in the generation of antibodies, e.g., as described in the Materials and Methods below. The polypeptides may be used in unmodified form, or they may be coupled to appropriate carrier molecules, such as bovine serum albumin (BSA) or Keyhole Limpet Hemocyanin (KLH) (available from, for example, Pierce, Rockford, Ill.).

Experiments performed in support of the present invention (see Materials and Methods) were used to identify an exemplary polypeptide antigen selectively immunoreactive with Bax-ω, where an immunoreactive portion of the antigen is homologous to a polypeptide encoded by the sequence represented as SEQ ID NO:18.

To prepare antibodies, a host animal, such as a rabbit, is typically immunized with the purified polypeptide, polypeptide coupled to carrier or fusion protein) generated using, for example glutathione-S-transferase as described above). The host serum or plasma is collected following an appropriate time interval, and the serum is tested for antibodies specific against the polypeptide.

Antibodies generated against Bax-ω are preferably produced against an epitope contained in the sequence represented herein as SEQ ID NO:13, such as the epitope represented as SEQ ID NO:18. Antibodies reactive with an epitope contained in SEQ ID NO:13 are not expected to cross-react with other known Bax polypeptides, such as Bax-α, Bax-β or Bax-γ.

The gamma globulin fraction or the IgG antibodies of immunized animals can be obtained, for example, by use of saturated ammonium sulfate precipitation or DEAE Sephadex chromatography, affinity chromatography, or other techniques known to those skilled in the art for producing polyclonal antibodies.

Alternatively, purified antigenic polypeptide, such a polypeptide containing the sequence represented herein as SEQ ID NO:13 or portion thereof (e.g., SEQ ID NO:18), or fused antigen protein may be used for producing monoclonal antibodies. In this case, the spleen or lymphocytes from an immunized animal are removed and immortalized or used to prepare hybridomas by methods known to those skilled in the art (e.g., Harlow, et al. 1988). Antibodies secreted by the immortalized cells are screened (e.g., using enzyme linked immunosorbent assay (ELISA) or a Western blot) to determine the clones that secrete antibodies of the desired specificity (e.g., Ausubel, et al.). The antibodies may also be affinity-purified, using methods known in the art (e.g., Harlow, et al.) prior to use.

Antibodies of FAb fragments thereof generated as described above may be used in a variety of ways. In particular, they could be used to detect or quantitate the level of Bax-ω polypeptides in any of the methods of the present invention where such detection is contemplated, e.g., in methods employing Western-based or ELISA-based detection approaches. Further, the antibodies can be used in screens of expression libraries, where the expression library is screened with a Bax-ω polypeptide and clones expressing polypeptides that bind to Bax-ω are identified using an antibody directed against Bax-ω. Alternatively or in addition, expression libraries may be screened directly with anti-Bax-ω antibodies to identify additional Bax-ω polypeptide and polynucleotide sequences. Such expression screening approaches are known in the art (e.g., Unit 6.7 of Ausubel, et al.).

The antibodies may also be used to co-immunoprecipitate proteins which interact with Bax-ω polypeptides. Here, a lysate from cells expressing Bax-ω is incubated with an antibody selectively immunoreactive with Bax-ω (such as described above) to produce a complex containing the antibody, Bax-ω, and any polypeptide that may be bound to Bax-ω. The complex is immunoprecipitated using standard methods and the polypeptide bound to Bax-ω is identifying by, for example, microsequencing a portion of the bound polypeptide.

Anti-Bax-ω antibodies may also be employed directly as therapeutic agents. Anti-Bax-ω antibodies produced as described herein may be tested for effects on apoptosis using, for example, one of the apoptosis assays described herein, to determine whether they have a statistically-significant effect on apoptosis. Antibodies identified as having such a functional effect may then be administered to cells or tissues in need of treatment. Such antibodies typically inhibit the function of the protein against which they are directed. Antibodies identified as having such an inhibitory effect on Bax-ω are therefore useful for promoting apoptosis, e.g., in tumor cells.

3. Bax-ω Polypeptide Therapeutic Applications. According to methods of the present invention, Bax-ω polypeptides may be administered therapeutically to inhibit apoptosis in cells (i.e., promote survival of the cells). Example 5 herein demonstrates the ability of expressed Bax-ω polypeptides to protect mammalian cells against apoptosis. The polypeptides may be administered using, for example, intracerebroventricular (ICV) administration, to protect against cell death caused by stroke. Alternatively, the polypeptides may be injected directly into tissues in need of treatment. To facilitate uptake of the polypeptides by cells, the polypeptides may be, for example, coupled to molecules which have uptake mechanisms in the targeted tissues (e.g., coupling to transferrin for uptake in the CNS).

Bax-ω polypeptides are also useful in methods of altering the activity of a Bcl-2-like polypeptide in a cell. Bax-ω polypeptide is administered to such a cell in an amount effective to significantly alter the activity of the Bcl-2-like polypeptide in the cell. Exemplary Bcl-2-like polypeptides amenable to this method include Bcl-XL, splice variants of Bcl-XL, Bax-α, splice variants of Bax-α, Bad, splice variants of Bad, splice variants of Bak, Bag and splice variants of Bag. According to the experiments detailed herein (Example 3, Table 1), Bax-ω is effective to form heterodimers with Bax-α, thus effectively altering the apoptosis-promoting activity of Bax-α.

Bax-ω polypeptides may also be useful for identifying lead compounds for drug development. For example, the structure of the BH2 domain of Bax-ω, which differs from the BH2 domain of other Bax transcripts, can be determined by, for example, NMR or X-ray crystallography, and used to design modified peptides, or other small molecules or lead compounds, which can be tested for specific properties (e.g. stimulation of or inhibition of apoptosis).

C. Models of Apoptosis

1. Co-Transfected Cells. Cells that normally undergo apoptosis may be co-transfected with Bax-ω and a partner of Bax-ω (PBω), e.g., Bax-α, to screen for therapeutic compounds (e.g., oligonucleotides, peptides or small molecules) that act to reduce the rate of, inhibit or prevent apoptosis, in order to identify compounds that may have cytoprotective properties. Alternatively, such cells may be screened for compounds that act to increase the rate of or promote apoptosis, in order to identify compounds that may be useful in anti-tumor therapies. Similarly, cells transfected with Bax-ω alone may be used to screen for therapeutic compounds that affect apoptosis.

2. PC6-3 NGF-Withdrawal Assay. The effects of a variety of compositions identified herein as altering apoptosis via an interaction with or disruption of Bax-ω polypeptides or polynucleotides may be evaluated using a suitable model for apoptosis. One such model is the PC6-3 assay (Example 6).

Results of previous experiments demonstrate that NGF withdrawal induces transcription-dependent programmed cell death in PC6-3 cells (Pittman, et al.; Shi, et al., 1992). Bax-ω antisense oligonucleotides may be applied to a culture of PC6-3 cells as NGF is withdrawn, and the effects on apoptosis measured using, for example, a DNA fragmentation assay (e.g., as described below and in Example 7).

3. DNA Fragmentation Assay. The DNA fragmentation assay is based on the observation that DNA which has undergone extensive internucleosomal fragmentation fails to sediment with large genomic DNA when subjected to centrifugation. Accordingly, fragmented DNA released from the nuclei of apoptotic cells can be separated from intact chromatin by a simple centrifugation step. A number of methods are available for measuring fragmented DNA. One such method is the quantitative "sandwich-enzyme-immunoassay" principle using two mouse monoclonal antibodies directed against DNA and BrdU (5-bromo-2-deoxyuridine). The reagents for this assay may be obtained either separately or in kit from Boehringer-Mannheim (Indianapolis, Ind.).

In the assay, microtiter wells are coated with the anti-DNA antibody. Samples containing BrdU-labeled DNA fragments are incubated in the coated wells, allowing the fragmented BrdU-labeled DNA present in the samples to bind to the immobilized anti-DNA antibody. The antibody-DNA complex is denatured and fixed by microwave irradiation, and incubated with an anti-BrdU peroxidase conjugate. Unbound conjugate is washed off, and the amount of peroxidase bound to the complex is detected photometrically with the peroxidase substrate, tetramethylbenzidine (TMB).

The DNA fragmentation assay is particularly suitable as a measure of apoptosis because it can detect the fragmented DNA (which is indicative of apoptosis) long before cells actually die. Advantages of this assay over other methods include its speed, sensitivity, and lack of use if radioactivity.

Other methods may also be used to assay apoptosis. For example, the In Situ Cell Death Detection Kit, AP, available from Boehringer Mannheim, is particularly well-suited for assaying apoptosis in high throughput screening applications. The assay employed in the kit allows the detection of apoptosis at the single cell level by light microscopy. DNA breaks due to apoptosis are detected by labeling the free 3'-OH termini with modified nucleotides (e.g., biotin-dUTP, DIG-dUTP, fluorescein-dUTP and the like) in an enzymatic reaction employing terminal deoxynucleotidyl transferase (TdT). This method is also referred to as TUNEL (TdT-mediated dUTP-X nick end labeling). An exemplary modified nucleotide is fluorescein-dUTP, which can be detected using an anti-fluorescein antibody conjugated with the reporter enzyme alkaline phosphatase (AP).

4. Animal Models of Ischemia. Therapeutic compositions of the present invention may also be tested in animal models of specific types of injury or disease which may be amenable to treatment using such compositions, in particular, animal models of cerebral ischemia. These models may be used to characterize, for example, the effects of therapeutic compositions described herein against known cell "suicide" genes on the progression of brain injury associated with ischemia.

Two animal models of cerebral ischemia which may be particularly suitable for use with methods and compositions of the present invention are the 4-vessel occlusion (4-VO) model of temporary global cerebral ischemia (Pulsinelli and Brierley, 1979) and the MCAO model of temporary focal cerebral ischemia (Buchan, et al., 1992). These models may be used to further characterize compositions of the present invention, and/or compositions identified by methods of the present invention for neuroprotective efficacy. Both models are described in detail in Example 8, below.

The 4-VO procedure produces severe bilateral forebrain ischemia of the kind associated with cardiac arrest. The anatomical distribution of necrotic changes is dependent on the duration of the ischemic insult and reproduces the well-established phenomenon of regional susceptibility to ischemic injury, i.e., a pattern of relative vulnerability, in decreasing order, involving the hippocampus, neocortex, and striatum (Pulsinelli, et al., 1982). The 4-VO procedure typically gives rise to neuronal pannecrosis within selectively vulnerable brain regions, however because the ischemic insult involves widespread brain areas, sporadic neuronal injuries occur throughout the forebrain.

The MCAO procedure, which has been well-characterized (Ginsberg and Busto, 1989), models ischemic brain injuries associated with stroke. As with other models of focal cerebral ischemia, MCAO (with or without reperfusion) produces localized neuronal injury at discrete cortical sites. An advantage of this model is that it produces a graded ischemia radiating outward from a dense central core where cerebral blood flow is maximally decreased. This offers an opportunity to assess the relative importance of regional variations in cerebral blood flow on the occurrence of necrosis and apoptosis.

VII. Other Methods Enabled by Bax-ω Compositions

An additional method of identifying compounds that are effective to alter apoptosis in a cell comprises the steps of contacting the cell with a test compound, measuring the effect of the test compound on Bax-ω activity of the level of expression of Bax-ω by the cell, and identifying the compound as effective if it increases or reduces Bax-ω activity or the level of expression of Bax-ω in the cell.

The cells may be, for example, cultured PC-12 cells that normally express quantifiable levels of the Bax-ω protein. A sample of cells ("test" sample) is incubated in a culture medium in the presence of an aliquot of test compound (e.g., suspended in an appropriate solvent, such as water or ethanol) and a "control" sample is incubated in culture medium containing an aliquot of the solvent alone. The incubation period may range from several hours to several days. The samples are then assayed to determine levels of Bax-ω expression. Compounds which result in a statistically significant increase or reduction of Bax-ω expression in treated cells relative to untreated cells are identified as effective to alter apoptosis.

The expression of Bax-ω may be assayed using, for example, any of the detection methods described above for the detection of Bax-ω polynucleotides or polypeptides. For example, quantitative PT-PCR may be employed to measure the level of Bax-ω mRNA expression in the two samples of cells. Alternatively, hybridization probes corresponding, for example, to SEQ ID NO:10, may be employed in Northern blot or RNAse protection assays. Kits for performing RNAse protection assays are available from commercial sources (e.g., Ambion, Inc., Austin, Tex.).

Bax-ω expression may also be assayed by measuring Bax-ω polypeptides in the cell samples. For example, a Western blot or slot blot approach may be employed with antibodies against Bax-ω (generated as described above using standard methods, e.g., as taught by Harlow, et al.).

VIII. Suitable Screening Compounds

A variety of different compounds may be screened using methods of the present invention. They include peptides, macromolecules, small molecules, chemical and/or biological mixtures, and fungal, bacterial, or algal extracts. Such compounds, or molecules, may be either biological, synthetic organic, or even inorganic compounds, and may be obtained from a number of sources, including pharmaceutical companies (e.g., Parke Davis, Ann Arbor, Mich.) and specialty suppliers of libraries (e.g., combinatorial libraries) of compounds (e.g., Brandon SPECS, Merrimack, N.H.).

Methods of the present invention are well suited for screening libraries of compounds in multi-well plates (e.g., 96-well plates), with a different test compound in each well. In particular, the methods may be employed with combinatorial libraries. A variety of combinatorial libraries of random-sequence oligonucleotides, polypeptides, or synthetic oligomers have been proposed (Kramer, et al., 1993; Houghten, 1985, 1994, Houghten, et al., 1986, 1991, 1992; Ohlmayer, et al., 1993; Dooley, et al., 1993a–1993b; Eichler, et al., 1993; Pinilla, et al., 1992, 1993; Ecker, et al., 1993; and Barbas, et al., 1992). A number of small-molecule libraries have also been developed (e.g., Bunin, et al., 1994; Bunin and Ellman, 1992; Virgilio and Ellman, 1994).

Combinatorial libraries of oligomers may formed by a variety of solution-phase or solid-phase methods in which mixtures of different subunits are added stepwise to growing oligomers or parent compound, until a desired oligomer size is reached (typically hexapeptide or heptapeptide). A library of increasing complexity can be formed in this manner, for example, by pooling multiple choices of reagents with each additional subunit step (Houghten, et al., 1991).

Alternatively, the library may be formed by solid-phase synthetic methods in which beads containing different-sequence oligomers that form the library are alternately mixed and separated, with one of a selected number of subunits being added to each group of separated beads at each step (Furka, et al., 1991; Lam, et al., 1991, 1993; Zuckermann, et al.; Sebestyen, et al., 1993)

The identity of library compounds with desired effects in the methods of the present invention can be determined by conventional means, such as iterative synthesis methods in which sublibraries containing known residues in one subunit position only are identified as containing active compounds.

The following examples illustrate but in no way are intended to limit the present invention.

MATERIALS AND METHODS

Unless otherwise indicated, restriction enzymes and DNA modifying enzymes were obtained from New England Biolabs (Beverly, Mass.) or Boehringer Mannheim (Indianapolis, Ind.). Other chemicals, including glutathione-agarose and thrombin, were purchased from Sigma (St. Louis, Mo.) or United States Biochemical (Cleveland, Ohio). Unless otherwise indicated, manipulations of bacteria, nucleic acids, proteins and antibodies were performed using standard methods and protocols (e.g., Sambrook, et al.; Ausubel, et al.; Harlow, et al.).

A. Buffers

1. Phosphate-buffered saline (PBS)
10+ stock solution, 1 liter:
80 g NaCl
2 g KCl
11.5 g Na$_2$HPO4—7H$_2$O
2 g KH$_2$PO$_4$
Working solution, pH 7.3:
137 mM NaCl
2.7 mM KCl
4.3 mM Na$_2$HPO$_4$—7H$_2$O
1.4 mM KH$_2$PO$_4$
    2. Stratagene "PCR OPTIMAL BUFFER #10"
1.5 mM MgCl$_2$
75 mM KCl
10 mM Tris (pH 9.2)
    3. 2× BES-buffered solution (BBS)
50 mM N,N-bis(2-hydroxyethyl)-2-aminoethanesulfonic acid (BES; CALBIOCHEM, La Jolla, Calif.)
280 mM NaCl
1.5 mM Na$_2$HPO$_4$, pH 6.95
800 ml H2O
Adjust to pH 6.95 with 1 N NaOH, room temperature
Add H$_2$O to 1 liter
Filter sterilize through a 0.45-μm nitrocellulose Nalgene filter (Nalgene, Rochester, N.Y.)
    4. SSC (sodium chloride/sodium citrate), 20×
3 M NaCl (175 g/liter)
0.3 M Na3citrate-2H2O (88 g/liter)
Adjust pH to 7.0 with 1 M HCl
    5. Cleavage Buffer
50 mM Tris-HCl (pH 8.0)
150 mM NaCl
2.5 mM CaCl$_2$
0.1% β-mercaptoethanol
10 μg/ml thrombin (~3000 U/mg)
    6. Incubation Buffer
20 mM HEPES, pH 7.4
150 mM potassium acetate
0.05% "TWEEN 20"
    7. Binding Buffer
20 mM HEPES (pH 7.4)
150 mM Potassium acetate
2.0 mM EDTA
0.05% "TWEEN-20"

B. Generation of antiBax-ωAntibodies

Anti-Bax-ω antisera were prepared in rabbits with peptide Bax-ω antigen #1 (SEQ ID NO:18) using standard methods (Harlow, et al.). Briefly, the peptide SEQ ID NO:18 was conjugated to keyhole limpet hemocyanin (KLH; Pierce, Rockford, Ill.) using manufacturer's instructions and the conjugate purified using manufacturer's gel filtration column. Approximately 250 μg of the conjugate was suspended in 1 ml PBS and injected subcutaneously (sc) into rabbits. A second injection was administered 3 weeks after the initial injection. The initial injection contained complete Freund's adjuvant, while subsequent injections contained incomplete Freund's adjuvant. Serum samples were collected from the rabbits every two weeks, starting one week after the second injection, to a total of three collections. The serum was affinity purified with Bax-ω using standard methods and used as described below.

EXAMPLE 1

Cloning Human Brain-Derived Bax cDNAs

A. PCR Amplification

Human Bax-ω cDNAs were isolated by screening a human brain hippocampal cDNA library (Clontech, Palo Alto, Calif.) using polymerase chain reaction (PCR; Mullis; Mullis, et al.) with Bax PCR primers (BaxF—SEQ ID NO:1; BaxR—SEQ ID NO:21). The primers were designed based on human Bax cDNA sequence (Oltvai, et al.) to amplify the entire Bax cDNA, including both the start and the stop codons.

One hundred nanograms of hippocampal cDNA was amplified in a 50 μl reaction mixture of Stratagene "PCR OPTIMAL BUFFER #10" containing 200 μM deoxynucleotide triphosphates (dNTPs), 1 μM of each primer, and 2.5 U Taq DNA polymerase. The reaction mixture was amplified as follows: The mixture was heated to 94° C. for 5 min, 60° C. for 2 min and 72° C. for 1.5 min, and was then exposed to 38 cycles of 94° C. for 1 min 20 sec, 60° C. for 2 min and 1.5 min at 72° C. Immediately following the last cycle, the mixture was heated to 94° C. for 1.5 min, 60° C. for 2 min and 72° C. for 10 min.

B. Cloning and Sequencing of PCR Products

DNA fragments amplified using the PCR conditions described above were end-filled with Klenow enzyme (Boehringer Mannheim, Indianapolis, Ind.) at 37° C. for 20 min in the presence of 5 nM dNTPs, and resolved on a 1% low-melt agarose gel ("SEAPLAQUE GTG", FMC BioProducts, Rockland, Me.). A piece containing DNA fragments having the predicted length of Bax cDNA (~600 bp) was excised from the gel digested with β-Agarase I (New England Biolabs, Beverly, Mass.). The DNA was purified using phenol/chloroform, precipitated with ethanol and blunt-ligated into the SmaI site of "BLUESCRIPT SK+" (Stratagene, La Jolla, Calif.).

The plasmid DNA was used to transform competent XL1-Blue MRF' cells (Stratagene) using a 45 second pulse to 42° C. Approximately 20 positive clones were selected for restriction mapping to determine the size of the inserts. Seven clones contained inserts of the size expected for Bax transcripts. Each of these was sequenced using an Applied Biosystems (Foster City, Calif.) sequencing apparatus following the manufacturer's protocol.

The sequence analysis revealed three groups of clones representing three different Bax splice variants. The cDNAs comprising the first group (Bax 1) were nearly identical to the Bax-α transcript described by Oltvai, et al., while those of the second group (Bax 2) were missing exon 2 (like Bax-γ in Oltvai, et al.), resulting in transcripts 151 amino acids shorter than the Bax 1 transcripts. The cDNAs comprising the third group (Bax 3) contained a novel 49 base pair sequence near their 3' end, which was followed by a nucleotide sequence from Bax exon 6. The Bax 3 cDNAs were termed Bax-omega (Bax-ω).

The 3' end of the Bax-ω gene was obtained using 3'-RACE (rapid amplification of cDNA ends) technology (Frohman, 1990; Frohman, et al., 1988). 3' RACE was performed according to the manufacturer's instructions (Gibco/BRL Research Products/LIFE TECHNOLOGIES, Inc. Gaithersburg, Md.) using the 4'-primer Bax 487 F (SEQ ID NO:3) and 3' primers having sequences represented as SEQ ID NO:19 and SEQ ID NO:20. Amplification of the cDNA was for 25 cycles as follows: melting at 94° C. for 1 min, annealing at 65° C. for 1 min and extension at 72° C. for 40 sec. The amplified DNA was subcloned into pCR3 using the TA-cloning kit (Invitrogen) and sequenced.

Both the consensus nucleotide sequence (SEQ ID NO:8) of the Bax-ω cDNAs, as well as the translated amino acid sequence (SEQ ID NO:9), are presented in FIG. 1 with the novel 49 bp region underlined.

It will be appreciated that the Bax-ω amino acid sequence represented by SEQ ID NO:9 (encoded by the nucleotide sequence represented by SEQ ID NO:8) apparently lacks a transmembrane domain. Accordingly, recombinant proteins consisting of these sequences (i.e., SEQ ID NO:9) are soluble, and may be employed as "soluble" proteins in protein-protein binding assays (described in Example 3, below).

C. Cloning and Sequencing of Bax Intron 5

To identify the Bax-ω alternative splicing site, intron 5 of the Bax gene was cloned from human genomic DNA (400 ng) using PCR. The upstream primer (Bax 462 F, SEQ ID NO:4) corresponded to a region of exon 5, and the downstream primer (Bax R, SEQ ID NO:21) corresponded to a region of exon 6 (see FIG. 2D).

Intron 5 sequences were amplified from human genomic DNA in 50 μl Stratagene "PCR OPTIMAL BUFFER #10" containing 1 μM of each primer, 200 μM dNTPs and 2.5 U Taq polymerase for 25 cycles (94° C. denature for 1 min, 65° C. annealing for 1 min, and 72° C. extension for 45 sec). Amplified DNA fragments were separated and purified on a 1% low-melting agarose gel ("SEAPLAQUE GTG"; FMC BioProducts, Rockland, Me.), and were cloned using the Invitrogen (San Diego, Calif.) "TA" cloning vector kit (vector pCR3) according to the manufacturer's instructions.

Two positive clones were identified and were sequenced using an Applied Biosystems automatic sequencer. Both clones contained the 49 nucleotide omega insert polynucleotide sequence.

D. Screening a cDNA Library

A human frontal cortex-LambaZAP cDNA library (Stratagene, La Jolla, Calif.; 1×10⁶ clones) was screened with a probe corresponding to the first 452 nucleotides of α-Bax radiolabeled by random priming (Boehringer Mannheim). The screening used standard hybridization protocols (Ausubel, et al.) followed by washing in 0.1× SSC, 0.1% sodium dodecyl sulfate (SDS) at 55° C. Seven independent positive clones were isolated and sequenced. Three of these contained 730 bp inserts that corresponded to positions 71–800 of ω-Bax. Four others contained partial sequences of α-Bax

EXAMPLE 2

In Vivo Expression of Bax-ω

A. Detection of Bax-ω transcripts by PCR

The expression of Bax-ω in various human tissues, as well as in various subregions of the brain, was assessed using reverse transcription PCR (RT-PCR).

1. Human RNA. Total RNA was extracted from several different regions of human brain, as well as other human tissues using the RNA-STAR kit (TEL-TEST 'B', Inc. Houston, Tex.). The extracted RNA samples were treated by incubating with 10 U RNase-free DNase (Stratagene, La Jolla, Calif.) at 37° C. for 1 hour followed by ethanol precipitation. Two nanograms of each RNA sample were reverse-transcribed into cDNA following the manufacturer's protocol for random-primed cDNA synthesis (BRL, Bethesda, Md.; 2 units (U) murine leukemia reverse transcriptase (MLV-RT; BRL) per 50 μl reaction. cDNA was produced by incubating the mixture at 37° C. for 25 min, followed by 5 cycles at 50° C., 20 sec and 37° C., 5 min. The cDNA samples were diluted 10-fold with distilled water and used for PCR amplification.

A set of Bax-ω specific primers were designed based on the 49 bp omega insert polynucleotide sequence and were used for PCR analysis of cDNA. The relative locations of the primers on a Bax-ω transcript are shown in FIG. 1. Upstream primers Bax 462 F (SEQ ID NO:4) and Bax 487 F (SEQ ID NO:3), and downstream primers Bax 590R (SEQ ID NO:5) and Bax R (SEQ ID NO:21) were used to amplify the cDNAs described above.

The cDNAs were amplified in 2.5 μl reaction mixtures in the presence of 50 μM dATP, 50 μM dGTP, 50 μM dTTP, 50 μCi ³²P-dCTP 1 nM each primer, and 0.125 U Tfl DNA polymerase (Epicentre Technologies, Madison) using hot-start PCR. The reaction mixtures were heated to 95° C. for 2 min. and cycled 30 times using the following settings: 94° C. for 40 sec, 65° C. for 1 min and 72° C. for 5 min.

In some of the PCR reactions described above, 18-S rRNA was amplified with primers 18S-F (SEQ ID NO:6) and 18S-R (SEQ ID NO:7) in the same tubes as the Bax-ω reactions for use as an internal control. The 18-S rRNA primers were added to the reaction mixture during the annealing step of the 8th cycle of the PCR amplification. Following PCR, the amplified DNAs were electrophoresed on a 5% polyacrylamide-urea gel and the gels imaged directly using a Phosphorimage Scanner (Phosphorimager, Molecular Dynamics).

The results are shown in FIG. 6A. Lane 1—thalamus; lane 2—cortex; lane 3—cerebellum; lane 4—hindbrain; lane 5—hippocampus; lane 6—liver; lane 7—kidney; lane 8—heart; lane 9—pancreas (female); lane 10—pancreas (male). Bax-ω nucleic acid sequences were detected in all human samples tested. FIG. 6B (quantitative control) shows amplification products obtained using primers corresponding to 18-S rRNA and same targets as were used in FIG. 6A (in the respective lanes).

2. Rat RNA. Similar PCR experiments were performed using rat tissue. Tissues from various organs were dissected from a sacrificed rat and rapidly frozen in liquid nitrogen. Total RNA was isolated by the method of Chomcyznski and Sacchi (1987), and first strand cDNA was synthesized using reverse transcriptase and primer Bax R (SEQ ID NO:21) at 42° C. for 30 min using standard methods (Sambrook, et al.). Following first strand synthesis, the reaction was supplemented with 1 μM primer Bax 462 F (SEQ ID NO:4), 200 μM dNTPs (dCTP was replaced with 10 μCi radiolabeled dCTP obtained from Amersham) and 10 U "DEEP VENT" DNA polymerase (New England Biolabs). The reaction mix was heated to 95° C. for 5 min and amplified for 30 cycles with the following conditions: denaturing at 95° C. for 1 min, annealing at 52° C. for 1 min and extension at 72° C. for 40 seconds. The amplification products were electrophoresed on a 5% polyacrylamide/urea gel and the gel was analyzed using a Phosphorimager Scanner (Molecular Dynamics, Sunnyvale, Calif.). Densitometric analysis of the bands was performed using the Phosphorimager analysis software.

Representations of exemplary gel images are shown in FIGS. 6A and 6B. The tissues are as follows: lane 1—thalamus; lane 2—cortex; lane 3—cerebellum; lane 4—hindbrain; lane 5—hippocampus; lane 6—liver; lane 7—kidney; lane 8—heart; lane 9—pancreas (female); lane 10—pancreas (male). FIG. 6A shows amplification products obtained using Bax primers. FIG. 6B shows the same RNA amplified under the same conditions using primers that amplify 18S rRNA (quantitative control).

Results of the experiments described above show that Bax-ω transcripts are readily detected in rat liver, lung, adrenal cortex, kidney, heart, skeletal muscle and brain, as well as human heart, liver and brain, including the thalamus, frontal cortex and hippocampus, indicating that Bax-ω is expressed in a variety of different tissue types.

EXAMPLE 3

Bcl-2/Bax-α/Bax-ω Protein-Protein Binding Assays

A. Yeast Two Hybrid Assays

The ability of Bax-α, Bax-ω and Bcl-2 to form homo- and hetero-dimers was studied using the yeast two hybrid protein-protein interaction system. A set of plasmid constructs encoding fusions of Bax-α, Bax-ω and Bcl-2 polypeptides with GAL4 binding domain or activation domain was generated using the pAS1-CYH (containing the GAL4 DNA binding domain) and/or GAD424 (containing the GAL4 transactivation domain) plasmids using standard PCR-based cloning techniques (e.g., Ausubel, et al.,; Sambrook, et al.).

A Bax-α DNA fragment (nucleotides 1 to 525) encoding a Bax-α polypeptide lacking the C-terminus transmembrane domain (the last 18 amino acid residues) was subcloned into pAS1-CYH, generating plasmid Baxα-pAS1. A Bcl-2 DNA fragment (nucleotides 1–648) encoding a Bcl-2 polypeptide lacking the C-terminus transmembrane domain (the last 21 amino acid residues) was subcloned into GAD424, generating plasmid Bcl2-GAD424.

Plasmid Bax-ω-pAS1, encoding a fusion of Bax-ω with GAL4 DNA binding domain was generated by ligating a BamH1-Sal1 fragment from plasmid Bax-ω-pBS (pBS-Bax-ω, #13; Bax-ω nucleotide residues 71–800) into BamH1-Sal1-digested Bax-ω-pAS1. This replaced the C-terminus of Bax-α in the plasmid with the C-terminus of Bax-ω from within the middle of exon 1.

Plasmid Bax-ω-GAL424, encoding a fusion of Bax-ω with the GAL4 transactivation domain, was generated by ligating an EcoRV/Sma1 fragment, containing full-length Bax-ω, from plasmid pBS-Bax-ω, #13 into Sma1-cut GAD424.

The reporter yeast strain, HF7C (Clontech), was transformed by the LiOAc method (Schiestl and Geist, 1989) with the appropriate pairs of fusion expression plasmids, plated on SD-Leu-Trp plates to select for the plasmid markers and assayed for activation of the HIS3 reporter gene by patching to SD-Leu-Trp-His plates and incubated at 30° C. for three day. Growth indicated the presence of a protein-protein interaction and no growth indicated the absence of an interaction.

For an additional assay, the reporter yeast strain, SFY526 (Clontech), was also transformed with pairs of the appropriate fusion expression plasmids, plated on SD-Leu-Trp and assayed for the activation of the β-galactosidase reporter gene by the filter assay with X-GAL as the substrate.

The results of the assays are shown in Table 1, below. Growth on His(−) plates and blue signals (representing β-galactosidase activity) are indicated by a (+). Absence of growth on His(−) plates and white signals (no β-galactosidase activity) are indicated by a (−). No positive signals were observed when cells were transformed with the fusion plasmids alone.

TABLE 1

| GAL4-DNA Binding Domain Hybrid | GAL4 Trans-Activation Domain Hybrid | β-Galactosidase Activity | Growth in the Absence of Histidine |
|---|---|---|---|
| Bax-α | Bcl-2 | + | + |
| Bax-α | Bax-ω | + | + |
| Bax-ω | Bcl-2 | − | − |
| Bax-ω | Bax-ω | − | − |

These data indicate that Bax-ω interacted with Bax-α as well as the positive control (Bcl-2/Bax-α). Bax-ω did not however interact with either Bcl-2 or with itself, suggesting that, unlike Bcl-2 and Bax-α, Bax-ω does not homodimerize.

B. GST Fusion Proteins

Glutathione-S-transferase (GST) fusion proteins of Bax-α and Bax-ω are prepared by cloning the coding sequences of the proteins into the pGEX-derived (Smith and Johnson) vector, pGEX-KG (Guan and Dixon, 1991). Sequences encoding Bax-α are disclosed, for example, in Oltvai, et al., 1993.

The plasmid pGEX-KG was derived from the pGEX-2T plasmid (Pharmacia Biotech, Piscataway, N.J.) by incorporation of an EcoRI fragment encoding a nine amino-acid glycine-rich linker (Guan and Dixon). The pGEX-2T plasmid was designed for inducible, high level intracellular expression of genes or gene fragments as fusions with *Schistosoma japonicum* glutathione S-transferase (GST; Smith and Johnson). It contains a tac promoter for chemically-inducible expression, the GST gene, a thrombin protease recognition site, a multiple cloning site, an ampicillin resistance gene, a pBR322 ori, and an internal lac Iq gene.

Sequences encoding Bax-ω and Bax-α are amplified from the plasmids in which they were originally isolated using PCR primers containing EcoRI and HindIII restriction sites. The amplified Bax-ω and Bax-α PCR products are cloned into the EcoRI/HindIII sites of pGEX-KG, resulting in pGST-Bax-ω and pGST-Bax-α, respectively.

The resultant vectors (pGST-Bax-ω and pGST-Bax-α) are used to transform XL-1 Blue *E. coli* cells (Stratagene, La Jolla, Calif.). Bacterial clones containing the protein sequences are selected and grown at 37° C., with vigorous agitation, for approximately 4 hours in 1-liter of liquid culture. One ml of 100 mM isopropyl-1-thio-β-D-galactoside (IPTG) is added to induce protein expression, and the culture is incubated for approximately another two hours.

The cells are pelleted and resuspended in 10 ml ice-cold phosphate-buffered saline, lysed until translucent, centrifuged briefly to pellet cellular debris, and the supernatant transferred to a fresh tube.

Five ml of a 50% (v/v) slurry of pre-swelled glutathione-agarose beads are added to the supernatant and mixed gently for approximately 1 hour at room temperature to allow fusion protein in the supernatant to bind to the beads. The beads are then washed three times to remove any unbound protein. Each wash consists of adding 10 ml PBS, mixing, and centrifuging in a table-top centrifuge for ~5 minutes at maximum speed (2000×g) to collect the beads.

The fusion protein may remain attached to the beads or it may be eluted using the thrombin cleavage protocol (Ausubel, et al.). In the cleavage protocol, 10–20 ml of the bead slurry are combined with 10 ml Cleavage Buffer and incubated at 25° C. for about 1 hour. Phenylmethylsulfonyl fluoride (0.6 mM final concentration) is then added to the protein elution, and the sample is concentrated to 0.5 ml using a "CENTRIPREP" concentrator (Amicon Inc., Beverly, Mass.). The protein is further purified by gel filtration.

Protein concentrations are estimated by Coomassie blue staining of protein bands after sodium dodecyl sulphate polyacrylamide gel electrophoresis (SDS-PAGE) using bovine serum albumin as a standard.

C. Western-Based Protein-Protein Binding Assay

In a GST fusion protein-protein binding assay, one of the pair of interacting proteins (e.g., Bax-α) is left immobilized on the agarose beads, while the other (e.g., a soluble form of Bax-ω; "free" or "soluble" protein) is cleaved from the beads as described above. The immobilized and free proteins are then incubated with one another in the presence and absence of a test compounds being assayed for its ability to interfere with the binding of the two protein. Typical binding incubations consist of approximately 0.3–2 $\mu$M GST-fusion proteins bound to glutathione agarose beads and approximately 1–4 $\mu$M soluble recombinant proteins in a total volume of ~50 $\mu$l of Incubation Buffer (with and without test compound). After a one hour incubation at 4° C. with gentle agitation, the beads are washed once with 200 $\mu$l Incubation Buffer containing 1 mg/ml gelatin and twice with 200 $\mu$l Incubation Buffer containing 5% glycerol. Proteins on the beads are solubilized in 8 $\mu$l electrophoresis sample buffer, electrophoresed on 12.5% resolving SDS-polyacrylamide (denaturing) gels, transferred to nitrocellulose paper (0.2 $\mu$M; Schleicher and Schuell, Keene, N.H.), and probed with suitable antibodies directed against the soluble protein using standard methods (Ausubel, et al.; Harlow, et al.).

D. Multiwell Plate Based Protein-Protein Binding Assay

Protein-protein interactions may also be assayed in a 96-well plate format. A number of detection schemes may be employed, including radioisotope-based, luminescence-based and fluorescence-based detection, as well as combinations of the above.

In one approach (scintillation proximity assay), based on scintillation proximity technology, recombinant fusion protein suspended in 50 mM Tris (pH 8.0; 4° C.) is incubated in multiwell plates (e.g., 96-well plates) containing a scintillant covalently incorporated into the plastic (e.g., "SCIN-TISTRIP" Wallac, Gaithersburg, Md.) overnight to immobilize the protein onto the wells of the plate. The plates are washed briefly in PBS (4° C.), followed by a wash with PBS containing 0.01% bovine serum albumin (BSA) for one hour at 4° C., and washed again with PBS. The "soluble" protein, or "ligand", is radiolabeled and incubated with the immobilized fusion protein in Binding Buffer for 1 hour. The wells are washed briefly to remove unbound ligand.

Bound ligand is detected by virtue of its proximity to the plate surface, which contains the scintillant. The signal is quantitated using a plate reader or counter, such as the "MICROBETA PLUS" plate counter (Wallac), to generate standard binding plots, which are useful in determining the optimal concentrations of proteins used in the assay. The assay is then conducted with and without test compounds to assess the effect of the test compounds on protein-protein binding.

Ligand is radiolabeled by translating the protein in vitro in the presence of $^{35}$S methionine using nuclease treated reticulocyte lysate (Promega Corp., Madison, Wis.). The ligand may also be radiolabeled by standard $^{125}$I iodination according to standard methods.

EXAMPLE 4

L929 Cells Transformed with Bax-ω

A. Transfection

The coding region of Bax-ω was sub-cloned into the vector pcDNA3 (Invitrogen, San Diego, Calif.), generating pcDNA3-Bax-ω. The pcDNA3 vector contains promoter sequences from the immediate early gene of cytomegalovirus (CMV) for high-level constitute transcription, polyadenylation signal and transcription termination sequences from bovine growth hormone to enhance RNA stability, and genes for both ampicillin and neomycin resistance. The vector also replicates episomally, which may be advantageous in use with the present invention, since episomal replication typically yields higher expression levels for the first six months following transfection as compared with integrated DNA. The vector is useful in both transient and stable expression studies.

Vector pcDNA3-Bax-ω was generated as follows. The "PBLUESCRIPT" construct containing the original Bax-ω clone (pBS-Bax-ω, #13) was digested with EcoRI to release the insert. The insert was digested with PstI and the two fragments generated were electrophoresed on an agarose gel and purified. The "PBLUESCRIPT" vector containing the Bax-ω clone isolated in the frontal cortex library screen (pBS-Bax-ω, frontal cortex), was also digested with EcoRI, the insert purified and then digested with PstI. The two fragments generated were electrophoresed on an agarose gel. The 5' EcoRI/PstI fragment from pBS-Bax-ω, #13 was ligated to the 3' PstI/EcoRI fragment from pBS-Bax-ω, frontal cortex, and then ligated to dephosphorylated EcoRI digested pcDNA3 vector, generating pcDNA3-Bax-ω (Bax-ω pcDNA3).

Mouse fibroblast L929 cells were transfected with pcDNA-3-Bax-ωplasmid DNA using electroporation as follows. L929 cells were grown in complete medium (DMEM supplemented with 10% fetal calf serum (HyClone Labs)) in an environment of 5% $CO_2$ at 37° C. One day prior to transfection, exponentially-growing cells were seeded at 5×10$^5$ cells per 10-cm tissue culture plate in 10 ml complete medium. The cells were then electroporated in PBS with 20 $\mu$g of ω-Bax pcDNA3 (at 250 volts, 250 $\mu$F) and grown for two days in complete medium. Stable transformants were selected using G-418. Drug-resistant clones were transferred to 24-well dishes and grown to confluence with drug selection.

A. Western Blot Analysis

Twenty four clonal cell lines (clones #1–#24) were obtained by the transfection methods described above. Several of these were evaluated by Western blot analysis for the expression levels of Bax-ω protein using the Bax-α antibody Bax (P-19) (Santa Cruz Labs), which cross-reacts with Bax-ω, as well as the anti-Bax-ω antiserum made as described above.

Protein samples were prepared from L929 cells (transfected with vector alone or with Bax-ω) as follows. The cells were grown to subconfluent levels, removed from a 10 cm tissue culture plate with Versene (200 mg/l EDTA tetrasodium in PBS; Gibco/BRL) and centrifuged for 5 minutes at 1500 rpm. The cell pellets were resuspended in 500 $\mu$l of ice cold RIPA containing aprotinin, PMSF (phenylmethylsulfonyl fluoride) and leupeptin, and were incubated at 4° C. for 1 hour. The protein lysates were centrifuged at 2500 rpm for 10 minutes at 4° C. and the resultant supernatant were subjected to the Bradford method of protein analysis (Bradford, 1976).

Following the Bradford analysis, equal amounts of protein were denatured by boiling for 10 minutes in RIPA containing 100 mM DTT and the proteins were electrophoresed on a 12% polyacrylamide/SDS gel. The gel was electroblotted on PVDF, blocked in TBS containing 0.5% non-fat dry milk (milk hybridization solution) for 30 minutes, and incubated with the primary antibody, P19 (Santa Cruz Labs, Santa Cruz, Calif.) for 1 hour in milk hybridization solution. The blot was then washed, and incubated with the secondary goat anti-rabbit antibody coupled to POD in milk hybridization solution for 1 hour, washed and visualized on XAR-5 film using chemiluminescence (ECL; Amersham Corporation, Arlington Heights, Ill.) followed by autoradiography.

A representation of an exemplary image, generated using P19, is shown in FIG. 7. Lane 1-vector-transfected L929; and 2-clone #1; lane 3-clone #3; lane 4-clone #2; lane 5-clone #4; lane 6-clone #5; lane 7-cone #7; lane 8-clone #8; lane 9-clone #11. These data show that the translated product migrated at 28 kd in SDS/polyacrylamide gel electrophoresis. The migration is the same as that seen in an in vitro rabbit reticulocyte translation assay, suggesting that the protein is processed in a similar way in vivo as in vitro, and that this processing increases the apparent mass of the protein from the predicted 24 kd to the observed 28 kd.

Blots probed with the anti-Bax-ω serum (1:1000) raised against antigen #1 contained the 28 kD Bax-ω and the 42 and 60 kD non-specific bands, but not the 22 kD Bax-α bands.

EXAMPLE 5

Bax-ω Expression Decreases TNF-Induced Cell Death

The Bax-ω-transfected L929 cells were used to determine the effects of Bax-ω on cell death. Exponentially growing L929 cells were seeded at 5–10×10$^5$ cells per 10 cm tissue culture plate (Falcon Labware, Oxnard, Calif.) in 10 ml of complete medium the day prior to the induction of cell death. Cell death was initiated by replacing the complete medium with Opti-MEM (Gibco, Ground Island, N.Y.) containing 40 ng/ml of tumor necrosis factor (TNF) and 10 μg/ml cycloheximide. After various times, the cells were scraped from the plates, centrifuged at 1500 rpm for 5 minutes and resuspended in Dulbecco's PBS containing 0.2% trypan blue. The cells were incubated in the trypan blue solution for 5 minutes, transferred to a hemacytometer and the number of viable (phase bright) and nonviable (blue) cells were recorded. Five fields were counted for each sample. Greater than 95% cell death was observed following a 20 hour treatment.

The results of an exemplary set of experiments, using vector-transfected L929 and three Bax-ω over-expressing clonal cell lines exposed to the TNF/cycloheximide solution for 12 hr, are shown in FIG. 8. The % viability represents the number of live cells divided by the total number of cells. Each data point represents the average of triplicate samples. Error bars are the standard deviation (s.d.) for three experiments.

Statistical analysis using the Peritz' F Test showed a significant difference between the various treatment groups (p>0.03)—all of the three cell lines tested (pcDNA3Bax-ω#1, pcDNA3Bax-ω#3 and pcDNA3Bax-ω#8) showed increased viability relative to the vector-transfected control. These data indicate that an increase in the levels of Bax-ω can reduce the amount of cell death in response to a apoptotis-initiation signal.

A dose response curve, shown in FIG. 9, was generated for the vector-transfected L929 cells and the three clonal cell lines described in FIG. 8. The concentration of cycloheximide remained the same for each condition with the concentration of TNF varying from 100 pg/ml to 40 ng/ml. Each data point represents the average of triplicate samples. ■ is vector-transfected L929 cells (control); ● is Bax-ω-transfected clone #1; ▲ is Bax-ω-transfected clone #3; and ♦ is Bax-ω-transfected clone #8.

The difference between the vector only-transfected L929 cells and the Bax-ω-transfected cells is readily apparent at the higher does of TNF, confirming that an increase in Bax-ω can reduce apoptosis.

A time course study was done to determine the duration of Bax-ω's protective effects following treatment with 40 ng/ml TNF. Vector transfected L929 cells and three Bax-ω over-expressing clonal cell lines were exposed to 40 ng/ml of TNF with 10 μg/ml of cycloheximide for 4.5, 6.5, 12 and 20 hr in Opti-MEM (Gibco/BRL). Following incubation, the cells were removed from the plates, stained with trypan blue and counted.

Figure 10:
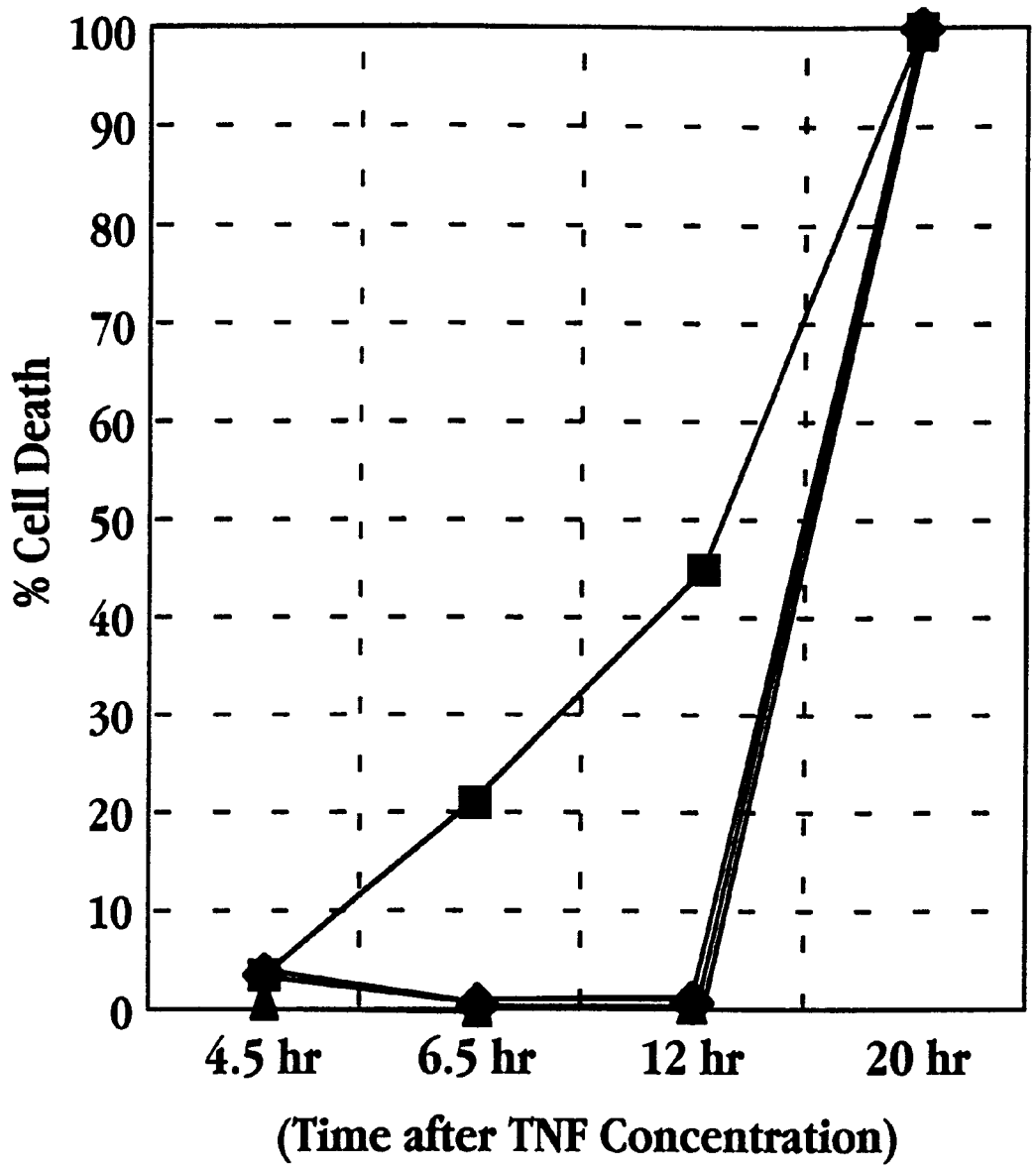
FIG. 10 shows the percent cell death of vector-transfected and Bax-ω-transfected L929 cells as a function of time after treatment in a TNF-induced apoptosis assay.

The results are shown in FIG. 10. The % cell death represents the number of dead cells divided by the total number of cells. Each data point represents the average of triplicate samples. ■ is vector-transfected L929 cells (control); ● is Bax-ω-transfected clone #1; ▲ is Bax-ω-transfected clone #3; and ♦ is Bax-ω-transfected clone #8. Statistical analysis using the Peritz'F Test showed a significant difference between the various treatment groups (p>0.05).

The results demonstrate the Bax-ω is protective for at least 12 hr following TNF treatment. Most of the cells died by 20 hr following TNF treatment, likely as a result of cycloheximide that prevents the ongoing translation of protective proteins. These data suggest that the half life of Bax-ω protein is less than 20 hr.

The data described above indicate that expression of Bax-ω protein protects cells from TNF-induced cell death, and that is protection may involve the interaction of Bax-ω with Bax-α.

EXAMPLE 6

PC6-3 Model of Apoptosis—Acceleration of Apoptosis by Bax-ω Antisense Oligonucleotides A. Oligonucleotide Design and Synthesis Phosphorothioate (PS) oligonucleotides or PS/phosphodiester (PD) oligos, typically 18 to 24 mers, are synthesized on an automated synthesizer (Biosearch 8750; Millipore) using H-phosphonate chemistry on controlled-pore glass, followed by oxidation with 0.2 M sulfur in carbon disulfide/pyridine/triethylamine (9:9:1, vol/vol). The oligonucleotides are then purified by low-pressure ion exchange chromatography (DEAE-cellulose, DE-52; Whatman) followed by reverse-phase chromatography ($C_{18}$) and dialysis. Sense and nonsense (same nucleotides in random order) oligonucleotides are used as controls.

B. Cell Culture

1. Naive Cells

Naive cells are incubated at 37° C. under 6% $CO_2$ on 100 mm tissue culture dishes and fed with RPMI medium (Gibco/BRL) supplemented with 10% equine and 5% fetal bovine sera, 100 units/ml penicillin and 0.1 mg/ml streptomycin, once every other day. Every five to seven days, the naive cells are split at a 1:6 dilution. To split the cells, the cultures are treated with trypsin/EDTA for 5 min and the cells are resuspended. Experiments are conducted on cells that had been passaged five times or less. After 5–6 passages, the cell lines are discarded and new lines are started from working stocks kept at −80° C. in 7% DMSO/ 93% fetal bovine serum. Original lines are stored in liquid nitrogen.

2. Neuronal Differentiation

PC6-3 cells (Pittman, et al.) are grown on tissue culture plates coated with collagen. Five ml of 50 µg/ml rat-tail collagen (diluted in sterile water) are absorbed to a 100 mm dish for 2 hr. Immediately prior to sub-culture, the collagen is removed and the cell suspension is added directly onto the plate (with no wash). The cells are split 1:10 into RPMI medium supplemented with 10% equine and 5% fetal bovine sera, 100 units/ml penicillin, 0.1 mg/ml streptomycin and 100 mg/ml NGF (2.5S, Collaborative Biomedical, Bedford, Mass.) lyophilized and resuspended in 0.2 M sodium acetate). The cells are fed with this medium every other day until day 7 to 9.

The RPMI/NGF medium is then replaced with DMEM/F-12 medium (Gibco/BRL), and the cells are aspirated into wells of a 6-well tissue culture plate that had been coated with 1 ml of a solution containing 150 µg/ml collagen. The cells are differentiated in a 1:1 mix of DMEM (high glucose; Gibco/BRL) and Ham's F-12 (Gibco/BRL) containing 100 U/ml penicillin/streptomycin, 100 ng/ml NGF, 5 µg/ml insulin, 10 µg/ml transferrin, 30 nM selenium, 20 nM progesterone, 100 µM putrescine and 100 µg/ml BSA.

C. Apoptosis Induction

On day 12, apoptosis is induced by replacing the DMEM/F12/NGF medium with the same medium containing, instead of NGF, 60 µg/ml anti-NGF IgG purified from rabbit polyclonal sera. Upon medium replacement (removal of NGF), the cells typically die over a reproducible time course (Pittman, et al.). At 8 hr, about 10% of the cells are dead. By 16 hr, the percentage of dead cells reaches about 35%, and by 24 hr it is up to about 80%. The number of cells committed to die (measured by adding back NGF) reaches a maximum at 14 to 18 hr.

EXAMPLE 7

DNA Fragmentation Assay for Detection of Apoptosis

PC6-3 cells are treated with oligonucleotides at concentrations of 1–100 µM for various times prior to NGF withdrawal, and throughout a 24 hr period of apoptosis. Oligonucleotides are added either directly or via liposome complexes to the media. The uptake and distribution following different delivery methods is monitored with fluorescein-labeled oligonucleotides (Clontech, Palo Alto, Calif.). The effects of treatment are monitored by the DNA fragmentation assay described below.

The DNA fragmentation assay is based on the observation that DNA which has undergone extensive internucleosomal fragmentation fails to sediment with large genomic DNA when subjected to centrifugation. Accordingly, fragmented DNA released from the nuclei of apoptotic cells can be separated from intact chromatin by a simple centrifugation step.

A number of methods are available for measuring fragmented DNA. One such method is the quantitative "sandwich-enzyme-immunoassay (ELISA)" principle using two mouse monoclonal antibodies directed against DNA and BrdU (5-bromo-2-deoxyuridine). The reagents for this assay may be obtained either separately or in kit form from Boehringer-Mannheim (Indianapolis, Ind.).

Microtiter wells are coated with the anti-DNA antibody. Samples containing BrdU-labeled DNA fragments are incubated in the coated wells, allowing the fragmented BrdU-labeled DNA present in the samples to bind to the immobilized anti-DNA antibody. The antibody-DNA complex is denatured and fixed by microwave irradiation, and incubated with an anti-BrdU peroxidase conjugate. Unbound conjugate is washed off, and the amount of peroxidase bound to the complex is detected photometrically with the peroxidase substrate, tetramethylbenzidine (TMB).

A. Labeling Cellular DNA with BrdU

Exponentially growing PC6-3 cells are incubated with 10 µM BrdU overnight at 37° C. in a humidified atmosphere. During the incubation, BrdU is actively incorporated into the DNA of proliferating target cells. After labeling, the cells are centrifuged at 250 g for 10 min and resuspended in culture medium. The cell concentration is adjusted to $1 \times 10^5$ cells/ml, and 100 µl of the cell suspension are transferred to each well of a 96-well flat bottom microtiter plate. Replicate wells of the plate contain 100 µl of either anti-NGF antibody in culture medium or culture medium alone. Following the transfer, the final volume in each well is 200 µl. The cells are incubated for a series of increasing time periods prior to measuring DNA fragmentation by ELISA.

After incubation for the appropriate time period, cells are centrifuged at 250 g for 10 min and 100 µl of supernatant are removed from each well for testing in the ELISA assay (SN sample). The cells in the well are lysed by adding 100 µl of Boehringer-Mannheim incubation buffer and incubating for 30 min at 37° C. The solution is centrifuged at 250 g for 10 min. and 100 µl of supernatant are removed for ELISA (LYS sample).

B. Anti-BrdU ELISA

One hundred µl of Coating Solution containing anti-DNA antibody is pipetted into each well of a microtiter plate and incubated for 1 hr at room temperature. The Coating Solution is then removed by suction and replaced for 30 min by a blocking solution containing "TWEEN-20". The wells are washed thoroughly to remove all traces of both antibody containing and blocking solutions. The SN and LYS samples are transferred directly without dilution into the pre-coated wells and incubated for 90 min at room temperature. The wells are washed, and the DNA-antibody complexes are fixed by microwave irradiation (~650 Watts) for 5 min. After cooling for 10 min at −20° C., anti-BrdU peroxidase conjugate solution is added and incubated for an additional 90 min at room temperature. The wells are then washed and the immunocomplexed anti-BrdU peroxidase is detected by TMB substrate. The reaction is carried out for 10 min at room temperature in the dark.

EXAMPLE 8

In Vivo Apoptosis Assays

A. Transient Global Ischemia

Male Fisher-344 rats are anesthetized with sodium pentobarbital and Silastic loops are placed loosely around each common carotid artery and exteriorized through double-lumen tubing. The vertebral arteries are permanently occluded by electrocoagulation at the first vertical vertebra. Two days after survey, global ischemia is produced by tightening the carotid clasps and securing them with bulldog clamps.

After 15 minutes the clamps are released to allow reperfusion. The animals are placed on a cooled metal plate for 2–4 hours to lower body temperature to 30–32° C., and then returned to their home cages. Those animals that do not lose the righting response after this procedure are eliminated from the study.

At fixed time points post-reperfusion, animals are sacrificed with $CO_2$, the rains are quickly removed and immersed in 10% (vol/vol) buffered formalin for 2–4 hours. Following the formalin fixation, the brains are paraffin-embedded for sectioning. A series of four to six 5 μm coronal sections is collected at intervals of approximately 300 μm. At least two sections of each series are to be stained with hematoxylin and eosin to visualize dead cells. Other sections are prepared using DNA end-labeling techniques ("APOPTAG", Oncor, Gaithersburg, Md.) to visualize DNA damage associated with apoptosis.

B. Focal Cerebral Ischemia

Spontaneously hypertensive male rats are anesthetized with halothane (2%) and the right common carotid artery (CCA) is isolated through a ventral midline incision and ligated. A 1 cm incision perpendicular to and bisecting a line between the lateral canthus of the right eye and the external auditory canal is made to allow partial excision of the underlying temporalis muscle. A burr hole 1 mm in diameter is drilled 2–3 mm rostral to the point of infusion of the zygomatic arch with the temporal bone.

The dura over the middle cerebral artery (MCA) is cut and retracted and a microaneurysm clip placed on the MCA at a site proximal to the point where it crosses the inferior cerebral vein in the rhinal fissure. Animals are subjected to 90 minutes of ischemia (permanent CCA and transient MCA) during which time the anesthesia is disconnected and the animals allowed to regain consciousness.

At the end of the ischemic episode, the animals are briefly reanesthetized, the MCA clip removed, and the incision sutured closed. The animals are allowed to regain consciousness for a reperfusion period of 18 hours. Physiological conditions including regional cerebral blood flows to both the core and the edge of the ischemic territory in the right neocortex are recorded at the start and finish of ischemia and at the time of sacrifice (Laserflow, Vasamedics, St. Paul, Minn.).

Beginning 18 hours postreperfusion, groups of animals are sacrificed by $CO_2$ asphyxiation. The brains are quickly removed and frozen in isopentane cooled on dry ice. A series of four to six coronal sections (20 μm thick) are cut at 300 μm intervals, dried on coverslips, and fixed for histological examination. As described above, at least two sections of each series are stained with crystal violet to visualize dead cells, and two are prepared using DNA end-labeling techniques ("APOPTAG", Oncor, Gaithersburg, Md.) to visualize DNA damage associated with apoptosis. Stained sections are examined by light microscopy and the infarcted area of each section is traced using a computer-assisted video image processing system.

EXAMPLE 9

ICV Administration of Therapeutic Compounds

The effects of intracerebroventricular (ICV) injections of therapeutic compositions (e.g., Bax-ω peptide compositions) on neuronal apoptosis in vivo is determined using rodent models of transient global and focal cerebral ischemia. After anesthetizing Fisher 344 rats with pentobarbital (60 mg/kg, ip), the vertebral arteries are permanently occluded and carotid claps are implanted to permit the induction of transient global forebrain ischemia.

Indwelling cannulae are placed at stereotaxic coordinates, A: 0.5, L: 1.5, H: 3.5, to enable ICV infusions of test/control articles. Cannulae are cemented to the skull with dental acrylic. Each rat is implanted with an osmotic minipump filled to deliver either test article (therapeutic substance) or sterile saline continuously at a rate of 1 μl/hr for 5 days. The pump is implanted subcutaneously below the scapula and connected to the ICV cannula via narrow gauge polyethylene tubing tunneled beneath the skin. After allowing two days for recovery, animals are subjected to 15 minutes of global cerebral ischemia followed by 2–4 hours of hypothermia (as above) and returned to the home cage facility.

Groups of animals are sacrificed by $CO_2$ asphyxiation 3, 5, 7 and 10 days post-occlusion. The brains are promptly removed, fixed in 10% buffered formalin, sectioned, mounted, and stained for detection of neuronal DNA fragmentation ("APOPTAG", Oncor, Gaithersburg, Md.) and neuronal necrosis.

EXAMPLE 10

In Situ Hybridization

Rats are sacrificed by $CO_2$ asphyxiation and the brains are removed quickly and frozen at −80° C. Coronal frozen sections (15–20 μm) at the level of the dorsal hippocampus are cut on a cryostate at −25° C., collected on 3-aminopropylethoxysilane-coated slides, and stored at −70° C. until use.

Oligonucleotides (40–60 mers) specific to Bax-ω, and Bax-α sequences are 3' end labeled with terminal deoxynucleotidaltransferase (Boehringer Mannheim) and $[\alpha\text{-}[^{35}S]$ thio]dATP (>1000 Ci/mmol, Amersham; 1 Ci=37 GBq) to a specific activity of $1.5 \times 10^9$ cpm/mg.

Sections are prehybridized for 1 hr at room temperature in a solution containing 4X standard saline citrate (SSC) and 1X Denhardt's solution. The slides are rinsed for 10 min in 4X SSC, acetylated for 10 min with acetic anhydride (0.5 ml per 200 ml of 0.1 M triethanolamine), and dehydrated. Hybridization is carried out overnight at 45° C.–50° C. in a hybridization buffer solution containing 50% (vol/vol) deionized formamide, 10% (wt/vol) dextran sulfate, 4S SSC, 1X Denhardt's solution, 5% (vol/vol) sodium N-lauroylsarcosine, 20 mM dithiothreitol, 20 mM sodium phosphate, 500 μg/ml denatured salmon sperm and 250 μg/ml yeast tRNA. For each slide, 35 ml of hybridization buffer containing $3 \times 10^5$ cpm of the denatured labeled oligonucleotide is used. Slides are then washed in 1X SSC/20 mM dithiothreitol at 55° C. twice for 30 min before dehydration and apposition to Hyperfilm-βmax (Amersham) for 10 days.

While the invention has been described with reference to specific methods and embodiments, it is appreciated that various modifications and changes may be made without departing from the invention.

It is claimed:

1. A substantially isolated polynucleotide, comprising at least 14 consecutive nucleotides, which will selectively hybridize to a DNA fragment having the sequence represented by the reverse complement of SEQ ID NO:10.

2. The polynucleotide of claim 1, where the polynucleotide is DNA.

3. The polynucleotide of claim 1, wherein the polynucleotide encodes the region of Bax-ω protein represented by SEQ ID NO:11 or portion thereof, said portion comprising at least five consecutive amino acids.

4. The polynucleotide of claim 3, wherein the polynucleotide contains the sequence represented as SEQ ID NO:10 or portion thereof, where said portion comprises at least 15 consecutive nucleotides.

5. The polynucleotide of claim 3, wherein the polynucleotide encodes the region of the Bax-ω protein represented by SEQ ID NO:13.

6. The polynucleotide of claim 5, wherein the polynucleotide contains the sequence represented as SEQ ID NO:12.

7. The polynucleotide of claim 3, wherein the polynucleotide encodes the entire Bax-ω protein.

8. The polynucleotide of claim 7, wherein the polynucleotide contains the sequence represented as SEQ ID NO:8.

9. A recombinant expression vector containing a polynucleotide, comprising at least 14 consecutive nucleotides, which will selectively hybridize to a DNA fragment having the sequence represented by the reverse complement of SEQ ID NO:10, wherein the polynucleotide encodes the region of Bax-ω protein represented by SEQ ID NO:11 or a portion thereof, said portion comprising at least five consecutive amino acids, said vector further containing a promoter operably linked to said polynucleotide, wherein the polynucleotide is positioned in the vector such that the region of Bax-ω protein represented by SEQ ID NO:11 or a portion thereof is expressed under control of said promoter in a desired host cell.

10. The vector of claim 9, where the vector is pcDNA3-Baxω.

* * * * *

SEQUENCE LISTING (1) GENERAL INFORMATION:

(iii) NUMBER OF SEQUENCES: 27

(2) INFORMATION FOR SEQ ID NO:1:

(i) SEQUENCE CHARACTERISTICS:
       (A) LENGTH: 27 base pairs
       (B) TYPE: nucleic acid
       (C) STRANDEDNESS: single
       (D) TOPOLOGY: linear (ii) MOLECULE TYPE: DNA (iii) HYPOTHETICAL: NO (iv) ANTI-SENSE: NO (vi) ORIGINAL SOURCE:
        (C) INDIVIDUAL ISOLATE: PCR primer Bax F (xi) SEQUENCE DESCRIPTION: SEQ ID NO:1:

GGAATTCGCG GTGATGGACG GGTCCGG                                              27

(2) INFORMATION FOR SEQ ID NO:2:

(i) SEQUENCE CHARACTERISTICS:
       (A) LENGTH: 27 base pairs
       (B) TYPE: nucleic acid
       (C) STRANDEDNESS: single
       (D) TOPOLOGY: linear (ii) MOLECULE TYPE: DNA (iii) HYPOTHETICAL: NO (iv) ANTI-SENSE: NO (vi) ORIGINAL SOURCE:
        (C) INDIVIDUAL ISOLATE: PCR primer Bax RI (Bax R primer with
            5' Eco RI site)

(xi) SEQUENCE DESCRIPTION: SEQ ID NO:2:

GGAATTCTCA GCCCATCTTC TTCCAGA                                              27

(2) INFORMATION FOR SEQ ID NO:3:

(i) SEQUENCE CHARACTERISTICS:
       (A) LENGTH: 26 base pairs
       (B) TYPE: nucleic acid
       (C) STRANDEDNESS: single
       (D) TOPOLOGY: linear (ii) MOLECULE TYPE: DNA (iii) HYPOTHETICAL: NO (iv) ANTI-SENSE: NO (vi) ORIGINAL SOURCE:
        (C) INDIVIDUAL ISOLATE: PCR primer Bax 487 F (xi) SEQUENCE DESCRIPTION: SEQ ID NO:3:

CTGGCCGAGT CACTGAAGCG ACTGAT                                               26

(2) INFORMATION FOR SEQ ID NO:4:

(i) SEQUENCE CHARACTERISTICS:
       (A) LENGTH: 24 base pairs (B) TYPE: nucleic acid
            (C) STRANDEDNESS: single
            (D) TOPOLOGY: linear (ii) MOLECULE TYPE: DNA (iii) HYPOTHETICAL: NO (iv) ANTI-SENSE: NO (vi) ORIGINAL SOURCE:
            (C) INDIVIDUAL ISOLATE: PCR primer Bax 462 F (xi) SEQUENCE DESCRIPTION: SEQ ID NO:4:

GAGCGGCTGT TGGGCTGGAT CCAA                                              24

(2) INFORMATION FOR SEQ ID NO:5:

(i) SEQUENCE CHARACTERISTICS:
            (A) LENGTH: 25 base pairs
            (B) TYPE: nucleic acid
            (C) STRANDEDNESS: single
            (D) TOPOLOGY: linear (ii) MOLECULE TYPE: DNA (iii) HYPOTHETICAL: NO (iv) ANTI-SENSE: NO (vi) ORIGINAL SOURCE:
            (C) INDIVIDUAL ISOLATE: PCR primer Bax 590 R (xi) SEQUENCE DESCRIPTION: SEQ ID NO:5:

GTCTGCCACG TGGGCGTCCC AAAGT                                             25

(2) INFORMATION FOR SEQ ID NO:6:

(i) SEQUENCE CHARACTERISTICS:
            (A) LENGTH: 26 base pairs
            (B) TYPE: nucleic acid
            (C) STRANDEDNESS: single
            (D) TOPOLOGY: linear (ii) MOLECULE TYPE: DNA (iii) HYPOTHETICAL: NO (iv) ANTI-SENSE: NO (vi) ORIGINAL SOURCE:
            (C) INDIVIDUAL ISOLATE: PCR primer 18S-F (xi) SEQUENCE DESCRIPTION: SEQ ID NO:6:

ATCCTGCCAG TAGCATATGC TTGTCT                                            26

(2) INFORMATION FOR SEQ ID NO:7:

(i) SEQUENCE CHARACTERISTICS:
            (A) LENGTH: 25 base pairs
            (B) TYPE: nucleic acid
            (C) STRANDEDNESS: single
            (D) TOPOLOGY: linear (ii) MOLECULE TYPE: DNA (iii) HYPOTHETICAL: NO (iv) ANTI-SENSE: NO (vi) ORIGINAL SOURCE:
            (C) INDIVIDUAL ISOLATE: PCR primer 18S-R (xi) SEQUENCE DESCRIPTION: SEQ ID NO:7:

TTATCCAAGT AGGAGAGGAG CGAGC                                                25

(2) INFORMATION FOR SEQ ID NO:8:

(i) SEQUENCE CHARACTERISTICS:
        (A) LENGTH: 822 base pairs
        (B) TYPE: nucleic acid
        (C) STRANDEDNESS: single
        (D) TOPOLOGY: linear (ii) MOLECULE TYPE: cDNA to mRNA (iii) HYPOTHETICAL: NO (iv) ANTI-SENSE: NO (vi) ORIGINAL SOURCE:
        (C) INDIVIDUAL ISOLATE: Bax- cDNA (ix) FEATURE:
        (A) NAME/KEY: CDS
        (B) LOCATION: 1..663

(xi) SEQUENCE DESCRIPTION: SEQ ID NO:8:

```
ATG GAC GGG TCC GGG GAG CAG CCC AGA GGC GGG GGG CCC ACC AGC TCT     48
Met Asp Gly Ser Gly Glu Gln Pro Arg Gly Gly Gly Pro Thr Ser Ser
 1               5                  10                  15

GAG CAG ATC ATG AAG ACA GGG GCC CTT TTG CTT CAG GGT TTC ATC CAG     96
Glu Gln Ile Met Lys Thr Gly Ala Leu Leu Leu Gln Gly Phe Ile Gln
             20                  25                  30

GAT CGA GCA GGG CGA ATG GGG GGG GAG GCA CCC GAG CTG GCC CTG GAC    144
Asp Arg Ala Gly Arg Met Gly Gly Glu Ala Pro Glu Leu Ala Leu Asp
         35                  40                  45

CCG GTG CCT CAG GAT GCG TCC ACC AAG AAG CTG AGC GAG TGT CTC AAG    192
Pro Val Pro Gln Asp Ala Ser Thr Lys Lys Leu Ser Glu Cys Leu Lys
     50                  55                  60

CGC ATC GGG GAC GAA CTG GAC AGT AAC ATG GAG CTG CAG AGG ATG ATT    240
Arg Ile Gly Asp Glu Leu Asp Ser Asn Met Glu Leu Gln Arg Met Ile
 65                  70                  75                  80

GCC GCC GTG GAC ACA GAC TCC CCC CGA GAG GTC TTT TTC CGA GTG GCA    288
Ala Ala Val Asp Thr Asp Ser Pro Arg Glu Val Phe Phe Arg Val Ala
                 85                  90                  95

GCT GAC ATG TTT TCT GAC GGC AAC TTC AAC TGG GGC CGG GTT GTC GCC    336
Ala Asp Met Phe Ser Asp Gly Asn Phe Asn Trp Gly Arg Val Val Ala
            100                 105                 110

CTT TTC TAC TTT GCC AGC AAA CTG GTG CTC AAG GCC CTG TGC ACC AAG    384
Leu Phe Tyr Phe Ala Ser Lys Leu Val Leu Lys Ala Leu Cys Thr Lys
        115                 120                 125

GTG CCG GAA CTG ATC AGA ACC ATC ATG GGC TGG ACA TTG GAC TTC CTC    432
Val Pro Glu Leu Ile Arg Thr Ile Met Gly Trp Thr Leu Asp Phe Leu
    130                 135                 140

CGG GAG CGG CTG TTG GGC TGG ATC CAA GAC CAG GGT GGT TGG GGG CTG    480
Arg Glu Arg Leu Leu Gly Trp Ile Gln Asp Gln Gly Gly Trp Gly Leu
145                 150                 155                 160

CCC CTG GCC GAG TCA CTG AAG CGA CTG ATG TCC CTG CCT CCA GGA CGG    528
Pro Leu Ala Glu Ser Leu Lys Arg Leu Met Ser Leu Pro Pro Gly Arg
                165                 170                 175

CCT CCT CTC CTA CTT TGG GAC GCC CAC GTG GCA GAC CGT GAC CAT CTT    576
Pro Pro Leu Leu Leu Trp Asp Ala His Val Ala Asp Arg Asp His Leu
            180                 185                 190

TGT GGC GGG AGT GCT CAC CGC CTC ACT CAC CAT CTG GAA GAA GAT GGG    624
Cys Gly Gly Ser Ala His Arg Leu Thr His His Leu Glu Glu Asp Gly
        195                 200                 205
```

```
CTG AGG CCC CCA GCT GCC TTG GAC TGT GTT TTT CCT CCA TAAATTATGG    673
Leu Arg Pro Pro Ala Ala Leu Asp Cys Val Phe Pro Pro
    210             215                 220

CATTTTTCTG GGAGGGGTGG GGATTGGGGG ACGTGGGCAT TTTTCTTACT TTTGTAATTA    733

ATGGGGGGTG TGGGGAAGAG TGGTCTTGAG GGGGTAATAA ACCTCCTTCG GGACACAAAA    793

AAAAAAAATG TCGACATCGA TCAGATCTG                                     822

(2) INFORMATION FOR SEQ ID NO:9:

(i) SEQUENCE CHARACTERISTICS:
        (A) LENGTH: 221 amino acids
        (B) TYPE: amino acid
        (D) TOPOLOGY: linear (ii) MOLECULE TYPE: protein (xi) SEQUENCE DESCRIPTION: SEQ ID NO:9:

Met Asp Gly Ser Gly Glu Gln Pro Arg Gly Gly Pro Thr Ser Ser
 1               5                  10                  15

Glu Gln Ile Met Lys Thr Gly Ala Leu Leu Leu Gln Gly Phe Ile Gln
             20                  25                  30

Asp Arg Ala Gly Arg Met Gly Gly Glu Ala Pro Glu Leu Ala Leu Asp
         35                  40                  45

Pro Val Pro Gln Asp Ala Ser Thr Lys Lys Leu Ser Glu Cys Leu Lys
     50                  55                  60

Arg Ile Gly Asp Glu Leu Asp Ser Asn Met Glu Leu Gln Arg Met Ile
 65                  70                  75                  80

Ala Ala Val Asp Thr Asp Ser Pro Arg Glu Val Phe Phe Arg Val Ala
                 85                  90                  95

Ala Asp Met Phe Ser Asp Gly Asn Phe Asn Trp Gly Arg Val Val Ala
            100                 105                 110

Leu Phe Tyr Phe Ala Ser Lys Leu Val Leu Lys Ala Leu Cys Thr Lys
            115                 120                 125

Val Pro Glu Leu Ile Arg Thr Ile Met Gly Trp Thr Leu Asp Phe Leu
    130                 135                 140

Arg Glu Arg Leu Leu Gly Trp Ile Gln Asp Gln Gly Gly Trp Gly Leu
145                 150                 155                 160

Pro Leu Ala Glu Ser Leu Lys Arg Leu Met Ser Leu Pro Pro Gly Arg
                165                 170                 175

Pro Pro Leu Leu Leu Trp Asp Ala His Val Ala Asp Arg Asp His Leu
            180                 185                 190

Cys Gly Gly Ser Ala His Arg Leu Thr His His Leu Glu Glu Asp Gly
            195                 200                 205

Leu Arg Pro Pro Ala Ala Leu Asp Cys Val Phe Pro Pro
    210                 215                 220

(2) INFORMATION FOR SEQ ID NO:10:

(i) SEQUENCE CHARACTERISTICS:
        (A) LENGTH: 49 base pairs
        (B) TYPE: nucleic acid
        (C) STRANDEDNESS: single
        (D) TOPOLOGY: linear (ii) MOLECULE TYPE: cDNA to mRNA (iii) HYPOTHETICAL: NO (iv) ANTI-SENSE: NO
```

(vi) ORIGINAL SOURCE:
      (C) INDIVIDUAL ISOLATE: 49 bp Bax omega insert (ix) FEATURE:
      (A) NAME/KEY: CDS
      (B) LOCATION: 1..49

(xi) SEQUENCE DESCRIPTION: SEQ ID NO:10:

| GGG | CTG | CCC | CTG | GCC | GAG | TCA | CTG | AAG | CGA | CTG | ATG | TCC | CTG | CCT | CCA | G | 49 |
|-----|-----|-----|-----|-----|-----|-----|-----|-----|-----|-----|-----|-----|-----|-----|-----|---|----|
| Gly | Leu | Pro | Leu | Ala | Glu | Ser | Leu | Lys | Arg | Leu | Met | Ser | Leu | Pro | Pro | | |
| 1 | | | | 5 | | | | | 10 | | | | | 15 | | | |

(2) INFORMATION FOR SEQ ID NO:11:

(i) SEQUENCE CHARACTERISTICS:
      (A) LENGTH: 16 amino acids
      (B) TYPE: amino acid
      (D) TOPOLOGY: linear (ii) MOLECULE TYPE: protein (xi) SEQUENCE DESCRIPTION: SEQ ID NO:11:

Gly Leu Pro Leu Ala Glu Ser Leu Lys Arg Leu Met Ser Leu Pro Pro
 1               5                  10                  15

(2) INFORMATION FOR SEQ ID NO:12:

(i) SEQUENCE CHARACTERISTICS:
      (A) LENGTH: 189 base pairs
      (B) TYPE: nucleic acid
      (C) STRANDEDNESS: double
      (D) TOPOLOGY: linear (ii) MOLECULE TYPE: cDNA to mRNA (iii) HYPOTHETICAL: NO (iv) ANTI-SENSE: NO (vi) ORIGINAL SOURCE:
      (C) INDIVIDUAL ISOLATE: cDNA portion of Bax omega from intron
          5 splice site to 3'end (ix) FEATURE:
      (A) NAME/KEY: CDS
      (B) LOCATION: 1..189

(xi) SEQUENCE DESCRIPTION: SEQ ID NO:12:

| GGG | CTG | CCC | CTG | GCC | GAG | TCA | CTG | AAG | CGA | CTG | ATG | TCC | CTG | CCT | CCA | 48 |
|-----|-----|-----|-----|-----|-----|-----|-----|-----|-----|-----|-----|-----|-----|-----|-----|----|
| Gly | Leu | Pro | Leu | Ala | Glu | Ser | Leu | Lys | Arg | Leu | Met | Ser | Leu | Pro | Pro | |
| 1 | | | | 5 | | | | | 10 | | | | | 15 | | |

| GGA | CGG | CCT | CCT | CTC | CTA | CTT | TGG | GAC | GCC | CAC | GTG | GCA | GAC | CGT | GAC | 96 |
|-----|-----|-----|-----|-----|-----|-----|-----|-----|-----|-----|-----|-----|-----|-----|-----|----|
| Gly | Arg | Pro | Pro | Leu | Leu | Leu | Trp | Asp | Ala | His | Val | Ala | Asp | Arg | Asp | |
| | | | 20 | | | | | 25 | | | | | 30 | | | |

| CAT | CTT | TGT | GGC | GGG | AGT | GCT | CAC | CGC | CTC | ACT | CAC | CAT | CTG | GAA | GAA | 144 |
|-----|-----|-----|-----|-----|-----|-----|-----|-----|-----|-----|-----|-----|-----|-----|-----|-----|
| His | Leu | Cys | Gly | Gly | Ser | Ala | His | Arg | Leu | Thr | His | His | Leu | Glu | Glu | |
| | | | 35 | | | | | 40 | | | | | 45 | | | |

| GAT | GGG | CTG | AGG | CCC | CCA | GCT | GCC | TTG | GAC | TGT | GTT | TTT | CCT | CCA | | 189 |
|-----|-----|-----|-----|-----|-----|-----|-----|-----|-----|-----|-----|-----|-----|-----|---|-----|
| Asp | Gly | Leu | Arg | Pro | Pro | Ala | Ala | Leu | Asp | Cys | Val | Phe | Pro | Pro | | |
| | 50 | | | | | 55 | | | | | 60 | | | | | |

(2) INFORMATION FOR SEQ ID NO:13:

(i) SEQUENCE CHARACTERISTICS:
      (A) LENGTH: 63 amino acids
      (B) TYPE: amino acid
      (D) TOPOLOGY: linear (ii) MOLECULE TYPE: protein (xi) SEQUENCE DESCRIPTION: SEQ ID NO:13:

Gly Leu Pro Leu Ala Glu Ser Leu Lys Arg Leu Met Ser Leu Pro Pro
 1               5                  10                  15

Gly Arg Pro Pro Leu Leu Leu Trp Asp Ala His Val Ala Asp Arg Asp
                20                  25                  30

His Leu Cys Gly Gly Ser Ala His Arg Leu Thr His His Leu Glu Glu
            35                  40                  45

Asp Gly Leu Arg Pro Pro Ala Ala Leu Asp Cys Val Phe Pro Pro
    50                  55                  60

(2) INFORMATION FOR SEQ ID NO:14:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: DNA (iii) HYPOTHETICAL: NO (iv) ANTI-SENSE: NO (vi) ORIGINAL SOURCE:
        (C) INDIVIDUAL ISOLATE: AP Primer (xi) SEQUENCE DESCRIPTION: SEQ ID NO:14:

CAGATCTGAT CGATGTCGAC ATTTTTTTTT TTT                                33

(2) INFORMATION FOR SEQ ID NO:15:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (iii) HYPOTHETICAL: NO (iv) ANTI-SENSE: NO (vi) ORIGINAL SOURCE:
        (C) INDIVIDUAL ISOLATE: PCR primer Jnct (xi) SEQUENCE DESCRIPTION: SEQ ID NO:15:

CAAGACCAGG GTGGTTGGGG GC                                            22

(2) INFORMATION FOR SEQ ID NO:16:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (iii) HYPOTHETICAL: NO (iv) ANTI-SENSE: YES (vi) ORIGINAL SOURCE:
        (C) INDIVIDUAL ISOLATE: antisense oligo directed against
            exon5/intron5 junction (xi) SEQUENCE DESCRIPTION: SEQ ID NO:16:

GCCCCCAACC ACCCTGGTCT TG                                                  22

(2) INFORMATION FOR SEQ ID NO:17:

(i) SEQUENCE CHARACTERISTICS:
        (A) LENGTH: 42 base pairs
        (B) TYPE: nucleic acid
        (C) STRANDEDNESS: double
        (D) TOPOLOGY: linear (ii) MOLECULE TYPE: DNA (iii) HYPOTHETICAL: NO (iv) ANTI-SENSE: NO (vi) ORIGINAL SOURCE:
        (C) INDIVIDUAL ISOLATE: exon 5/intron 5 junction (xi) SEQUENCE DESCRIPTION: SEQ ID NO:17:

CAAGACCAGG GTGGTTGGGG GCTGCCCCTG GCCGAGTCAC TG                             42

(2) INFORMATION FOR SEQ ID NO:18:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (vi) ORIGINAL SOURCE:
        (C) INDIVIDUAL ISOLATE: Bax omega epitope #1 (antigen #1)

(xi) SEQUENCE DESCRIPTION: SEQ ID NO:18:

His His Leu Glu Glu Asp Gly Leu Arg Pro Pro Ala Ala Leu Asp
1               5                   10                  15

(2) INFORMATION FOR SEQ ID NO:19:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: DNA (iii) HYPOTHETICAL: NO (iv) ANTI-SENSE: NO (vi) ORIGINAL SOURCE:
        (C) INDIVIDUAL ISOLATE: 3' RACE PCR primer 1

(xi) SEQUENCE DESCRIPTION: SEQ ID NO:19:

CGCAGATCTG ATCGATGTCG GCATTTTTTT TTTTTT                                   36

(2) INFORMATION FOR SEQ ID NO:20:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (iii) HYPOTHETICAL: NO (iv) ANTI-SENSE: NO (vi) ORIGINAL SOURCE:
              (C) INDIVIDUAL ISOLATE: 3' RACE PCR primer 2

(xi) SEQUENCE DESCRIPTION: SEQ ID NO:20:

GTCGCAGATC TGATCGATGT CGACAT                                                26

(2) INFORMATION FOR SEQ ID NO:21:

(i) SEQUENCE CHARACTERISTICS:
              (A) LENGTH: 21 base pairs
              (B) TYPE: nucleic acid
              (C) STRANDEDNESS: single
              (D) TOPOLOGY: linear (ii) MOLECULE TYPE: DNA (iii) HYPOTHETICAL: NO (iv) ANTI-SENSE: NO (vi) ORIGINAL SOURCE:
              (C) INDIVIDUAL ISOLATE: PCR primer Bax R (xi) SEQUENCE DESCRIPTION: SEQ ID NO:21:

CTCAGCCCAT CTTCTTCCAG A                                                     21

(2) INFORMATION FOR SEQ ID NO:22:

(i) SEQUENCE CHARACTERISTICS:
              (A) LENGTH: 60 amino acids
              (B) TYPE: amino acid
              (C) STRANDEDNESS: single
              (D) TOPOLOGY: linear (ii) MOLECULE TYPE: protein (iii) HYPOTHETICAL: NO (iv) ANTI-SENSE: NO (vi) ORIGINAL SOURCE:
              (C) INDIVIDUAL ISOLATE: translation of second open reading
                  frame in Fig. 2

(xi) SEQUENCE DESCRIPTION: SEQ ID NO:22:

Gly Cys Pro Trp Pro Ser His Ser Asp Cys Pro Cys Leu Gln Asp Gly
1               5                  10                  15

Leu Leu Ser Tyr Phe Gly Thr Pro Thr Trp Gln Thr Val Thr Ile Phe
            20                  25                  30

Val Ala Gly Val Leu Thr Ala Ser Leu Thr Ile Trp Lys Lys Met Gly
        35                  40                  45

Gly Pro Gln Leu Pro Trp Thr Val Phe Phe Leu His
    50                  55                  60

(2) INFORMATION FOR SEQ ID NO:23:

(i) SEQUENCE CHARACTERISTICS:
              (A) LENGTH: 34 amino acids
              (B) TYPE: amino acid
              (C) STRANDEDNESS: single
              (D) TOPOLOGY: linear (ii) MOLECULE TYPE: protein -continued (iii) HYPOTHETICAL: NO (iv) ANTI-SENSE: NO (vi) ORIGINAL SOURCE:
              (C) INDIVIDUAL ISOLATE: underlined portion of SEQ ID NO:22
                  in Fig. 2

(xi) SEQUENCE DESCRIPTION: SEQ ID NO:23:

Asp Gly Leu Leu Ser Tyr Phe Gly Thr Pro Thr Trp Gln Thr Val Thr
1               5                   10                  15

Ile Phe Val Ala Gly Val Leu Thr Ala Ser Leu Thr Ile Trp Lys Lys
            20                  25                  30

Met Gly (2) INFORMATION FOR SEQ ID NO:24:

(i) SEQUENCE CHARACTERISTICS:
              (A) LENGTH: 62 amino acids
              (B) TYPE: amino acid
              (C) STRANDEDNESS: single
              (D) TOPOLOGY: linear (ii) MOLECULE TYPE: protein (iii) HYPOTHETICAL: NO (iv) ANTI-SENSE: NO (vi) ORIGINAL SOURCE:
              (C) INDIVIDUAL ISOLATE: translation of third open reading
                  frame in Fig. 2

(xi) SEQUENCE DESCRIPTION: SEQ ID NO:24:

Ala Ala Pro Gly Arg Val Thr Glu Ala Thr Asp Val Pro Ala Ser Arg
1               5                   10                  15

Thr Ala Ser Ser Pro Thr Leu Gly Arg Pro Arg Gly Arg Pro Pro Ser
            20                  25                  30

Leu Trp Arg Glu Cys Ser Pro Pro His Ser Pro Ser Gly Arg Arg Trp
        35                  40                  45

Ala Glu Ala Pro Ser Cys Leu Gly Leu Cys Phe Ser Ser Ile
    50                  55                  60

(2) INFORMATION FOR SEQ ID NO:25:

(i) SEQUENCE CHARACTERISTICS:
              (A) LENGTH: 42 amino acids
              (B) TYPE: amino acid
              (C) STRANDEDNESS: single
              (D) TOPOLOGY: linear (ii) MOLECULE TYPE: protein (iii) HYPOTHETICAL: NO (iv) ANTI-SENSE: NO (vi) ORIGINAL SOURCE:
              (C) INDIVIDUAL ISOLATE: C-terminal portion of Bax-alpha
                  shown in Fig. 4

(xi) SEQUENCE DESCRIPTION: SEQ ID NO:25:

Trp Ile Gln Asp Gln Gly Gly Trp Asp Gly Leu Leu Ser Tyr Phe Gly
1               5                   10                  15

Thr Pro Thr Trp Gln Thr Val Thr Ile Phe Val Ala Gly Val Leu Thr
            20                  25                  30

Ala Ser Leu Thr Ile Trp Lys Lys Met Gly

-continued

```
            35                  40
```

(2) INFORMATION FOR SEQ ID NO:26:

(i) SEQUENCE CHARACTERISTICS:
        (A) LENGTH: 68 amino acids
        (B) TYPE: amino acid
        (C) STRANDEDNESS: single
        (D) TOPOLOGY: linear (ii) MOLECULE TYPE: protein (iii) HYPOTHETICAL: NO (iv) ANTI-SENSE: NO (vi) ORIGINAL SOURCE:
        (C) INDIVIDUAL ISOLATE: C-terminal portion of Bax-beta in
            Fig. 4

(xi) SEQUENCE DESCRIPTION: SEQ ID NO:26:

```
Trp Ile Gln Asp Gln Gly Gly Trp Val Arg Leu Leu Lys Pro Pro His
1               5                   10                  15

Pro His His Arg Ala Leu Thr Thr Ala Pro Ala Pro Pro Ser Leu Pro
            20                  25                  30

Pro Ala Thr Pro Leu Gly Pro Trp Ala Phe Trp Ser Arg Ser Gln Trp
            35                  40                  45

Cys Pro Leu Pro Ile Phe Arg Ser Ser Asp Val Val Tyr Asn Ala Phe
50                  55                  60

Ser Leu Arg Val
65
```

(2) INFORMATION FOR SEQ ID NO:27:

(i) SEQUENCE CHARACTERISTICS:
        (A) LENGTH: 71 amino acids
        (B) TYPE: amino acid
        (C) STRANDEDNESS: single
        (D) TOPOLOGY: linear (ii) MOLECULE TYPE: protein (iii) HYPOTHETICAL: NO (iv) ANTI-SENSE: NO (vi) ORIGINAL SOURCE:
        (C) INDIVIDUAL ISOLATE: C-terminal portion of Bax-omega
            shown in Fig. 4

(xi) SEQUENCE DESCRIPTION: SEQ ID NO:27:

```
Trp Ile Gln Asp Gln Gly Gly Trp Gly Leu Pro Leu Ala Glu Ser Leu
1               5                   10                  15

Lys Arg Leu Met Ser Leu Pro Pro Gly Arg Pro Pro Leu Leu Leu Trp
            20                  25                  30

Asp Ala His Val Ala Asp Arg Asp His Leu Cys Gly Gly Ser Ala His
            35                  40                  45

Arg Leu Thr His His Leu Glu Glu Asp Gly Leu Arg Pro Pro Ala Ala
    50                  55                  60

Leu Asp Cys Val Phe Pro Pro
65                  70
```